(12) United States Patent
Hermans et al.

(10) Patent No.: US 9,850,315 B2
(45) Date of Patent: Dec. 26, 2017

(54) ANTIGEN-BINDING PROTEIN DIRECTED AGAINST EPITOPE IN THE CH1 DOMAIN OF HUMAN IGG ANTIBODIES

(75) Inventors: Wilhelmus Josephus Johanna Hermans, Oud-Gastel (NL); Sven Blokland, Delft (NL); Maria Anna van Kesteren, Leiden (NL); Johanna Magaretha Horrevoets, Delft (NL); Franciscus Johan Marinus Detmers, Nijmegen (NL)

(73) Assignee: BAC IP B.V., Naarden (NL)

( * ) Notice: Subject to any disclaimer, the term of this patent is extended or adjusted under 35 U.S.C. 154(b) by 296 days.

(21) Appl. No.: 13/982,970

(22) PCT Filed: Jan. 31, 2012

(86) PCT No.: PCT/NL2012/050051
§ 371 (c)(1),
(2), (4) Date: Sep. 3, 2013

(87) PCT Pub. No.: WO2012/105833
PCT Pub. Date: Aug. 9, 2012

(65) Prior Publication Data
US 2013/0337478 A1     Dec. 19, 2013

Related U.S. Application Data

(60) Provisional application No. 61/438,408, filed on Feb. 1, 2011.

(30) Foreign Application Priority Data

Feb. 1, 2011  (EP) ..................................... 11152952

(51) Int. Cl.
| | | |
|---|---|---|
| *C07K 16/42* | (2006.01) | |
| *C07K 1/22* | (2006.01) | |
| *C07K 16/06* | (2006.01) | |
| *C07C 19/00* | (2006.01) | |

(52) U.S. Cl.
CPC ............ *C07K 16/4241* (2013.01); *C07K 1/22* (2013.01); *C07K 16/065* (2013.01); *C07K 16/42* (2013.01); *C07K 16/4283* (2013.01); *C07K 2317/22* (2013.01); *C07K 2317/33* (2013.01); *C07K 2317/34* (2013.01); *C07K 2317/522* (2013.01); *C07K 2317/569* (2013.01)

(58) Field of Classification Search
None
See application file for complete search history.

(56) References Cited

U.S. PATENT DOCUMENTS

| | | | | |
|---|---|---|---|---|
| 2005/0037421 A1* | 2/2005 | Honda | ................... | C07K 16/00 435/7.1 |
| 2008/0280346 A1* | 11/2008 | de Lorenzo Prieto | ................... | C07K 14/245 435/252.3 |
| 2010/0168393 A1* | 7/2010 | Clube | ................... | C07K 16/005 530/387.3 |
| 2010/0261620 A1* | 10/2010 | Almagro | ............... | C07K 16/244 506/26 |
| 2010/0311119 A1* | 12/2010 | Hermans | ............ | C07K 16/4283 435/69.1 |

FOREIGN PATENT DOCUMENTS

| | | | | |
|---|---|---|---|---|
| GB | WO 2007042809 A2 * | 4/2007 | ........... | C07K 16/005 |
| WO | 2006/059904 | 6/2006 | | |
| WO | WO-2007/042809 | 4/2007 | | |
| WO | 2009/011572 | 1/2009 | | |

OTHER PUBLICATIONS

Klimka et al., "Human anti-CD30 recombinant antibodies by duided phage antibody selection using cell panning" British Journal of Cancer (2000) 83: pp. 252-260.*
Brown et al. "Tolerance to Single, but not multiple, amino acid replacements in antibody VH CDR2" J. Immuno, 1996, 156: pp. 3285-3291.*
Vajdos et al. "Comprehensive functional maps of the antigen-binding site of an anti-ErbB2 antibody obtained with shotgun scanning mutagenesis" J. Mol. Biol. (2002) 320, pp. 415-428.*
Beiboer et al., "Guided selection of a pan carcinoma specific antibody reveals similar binding characteristics yet structural divergence between the original murine antibody and its human equivalent" J. Mol Biol. (2000) 296: pp. 833-849.*
EP11152952, "Search Report dated Jun. 22, 2011", Jun. 22, 2011, 11 Pages.
Klooster, R. et al., "Improved anti-IgG and HSA affinity ligands: Clinical application of VHH antibody technology", *Journal of Immunological Methods*, vol. 324, 2007, 1-12.
PCT/NL2012/050051, "Search Report dated May 3, 2012", May 3, 2012, 8 Pages.
Hermans, CaputreSelect Affinity Ligands, http://www.captureselect.nl/downloads/Peptalk2010.pdf, pp. 1-17, 2010.
Detmers, Novel Affinity Ligands Provide for Highly Selective Primary Capture, BioProcess International, pp. 50-54, 2010.
Hermans, Implementation of Notice Affinity Ligands for Biotherapeutic Purification, Downstream-Cap '05 abstracts, pp. 2005 9-11, 2005.

(Continued)

*Primary Examiner* — Daniel E Kolker
*Assistant Examiner* — James Rogers
(74) *Attorney, Agent, or Firm* — Daphne Reddy

(57) ABSTRACT

The present disclosure relates to a method for the purification of a human IgG-CH1 domain comprising molecule using an antigen-binding protein that is capable of binding to an epitope that is comprised in the CH1 domain of each of human IgG1, human IgG2, human IgG3 and human IgG4. The disclosure further relates to the antigen-binding proteins that can be used in the method of the disclosure. The frame-work regions of the antigen-binding proteins of the invention preferably correspond to those of antibodies that naturally are devoid of light chains as may e.g. be found in camelids. The disclosure further relates to nucleic acids that encode such antigen-binding proteins, to immunoadsorbent materials that comprise such proteins, and to the uses of such immunoadsorbent materials for the purification of IgG-CH1 domain containing molecules from a variety of species.

7 Claims, 23 Drawing Sheets

(56) References Cited

OTHER PUBLICATIONS

Haaft, Separations in Proteomics: Use of Camelid Antibody Fragments in the Depletion and Enrichment of Human Plasma Proteins for Proteomics Applications, http://www.captureselect.com/downloads/separations-in-proteomics.pdf, pp. 29-40, 2005.
Solder, Anti-Viral Antibodies in HIV (HTLV-III) Infection Possess Auto-Antibody Activity Against a CH1 Domain Determinant in Human IgG: Possible Immunological Consequences, Immunology Letters 23:1, pp. 9-19, 1989.
Dietrich, A monoclonal Anti-Idiotypic Antibody Against the Antigen-Combining Site and Anti-Factor VIII Autoantibodies Defines and Idiotope That is Recognized by Normal Human Polyspecific Immunoglobulins for Therapeutic Use (IVIg), Journal of Autoimmunity 3, pp. 547-557, 1990.
Derrick, The Third IgG-Binding Domain form Streptococcal Protein G—an Analysis by X-Ray Crystallography of the Structure Alone and in a Complex with Fab, Journal of Molecular Biology 243, pp. 906-918 1994.
Nguyen, Camel Heavy-Chain Antibodies: Diverse Germline VHH and Specific Mechanisms Enlarge the Antigen-Binding Repertoire, The EMBO Journal 19:5, pp. 921-930, 2000.
Anonymous, Product Sheet CaptureSelect IgG-Ch1 Affinity Matrix, http://www.captureselect.com/shopfiles/upload/files/Product_Sheet_CaptureSelect_IgG-CH1.pdf, pp. 1-4, 2011.
Yu, B et al., "Functional Regions of Immunoglobulin", *Biotechnology of Traditional Chinese Medicine, a textbook for traditional Chinese pharmacology and pharmacology majors in Higher Medical Institution, China Medical Science Press*, Dec. 2005, 402.

* cited by examiner

Fig. 1 (Cont.)

```
09CH1-7 k0-8  QVQLQESGGGLVQAGGSLRLSCAVSG    NTLS----RYAMG  WFRQTPGN--EREFVA    AIRW----
NNGATYYAESVE  GR------FTISRDNGKNT--VYLQMNNLQPEDTAVYYCAG          RFLGYASSNAYHEALYNY-----DY  WGQGTQVTVSS
10CH1-7 k1-0  QVQLQESGGGLVQAGGSLRLSCAVSG    NTLS----RYAMG  WFRQTPGK--EREFVA    AIRW----
NNGATYYADSVE  GR------FTISRDSGKNT--VYLQMNNLQPEDTAVYYCAG          RFLGYASSNAYHEALYNY-----DY  WGQGTQVTVSS
11CH1-7 k1-1  QVQLQESGGGLVQAGGSLRLSCAVSG    NTLS----RYAMG  WFRQTPGK--EREFVA    AIRW----
NNGATYYAESVE  GR------FTISRDSGKNT--VYLQMNNLQPEDTAVYYCAG          RFLGYASSNAYHEALYNY-----DY  WGQGTQVTVSS
12CH1-7 k1-2  QVQLQESGGGLVQAGGSLRLSCAVSG    NTLS----RYAMG  WFRQTPGK--EREFVA    AIRW----
NNGATYYADSVE  GR------FTISRDTGKNT--VYLQMNNLQPEDTAVYYCAG          RFLGYASSNAYHEALYNY-----DY  WGQGTQVTVSS
13CH1-7 k1-3  QVQLQESGGGLVQAGGSLRLSCAVSG    NTLS----RYAMG  WFRQTPGK--EREFVA    AIRW----
NNGATYYAESVE  GR------FTISRDTGKNT--VYLQMNNLQPEDTAVYYCAG          RFLGYASSNAYHEALYNY-----DY  WGQGTQVTVSS
14CH1-7 k1-4  QVQLQESGGGLVQAGGSLRLSCAVSG    NTLS----RYAMG  WFRQTPGK--EREFVA    AIRW----
NNGATYYADAVE  GR------FTISRDTGKNT--VYLQMNNLQPEDTAVYYCAG          RFLGYASSNAYHEALYNY-----DY  WGQGTQVTVSS
15CH1-7 k1-5  QVQLQESGGGLVQAGGSLRLSCAVSG    NTLS----RYAMG  WFRQTPGK--EREFVA    AIRW----
NNGATYYADSVE  GR------FTISRDNGKNT--VYLQMNNLQPEDTAVYYCAG          RFLGYASSNAYHEALYNY-----DY  WGQGTQVTVSS
16CH1-7 k1-6  QVQLQESGGGLVQAGGSLRLSCAVSG    NTLS----RYAMG  WFRQTPGK--EREFVA    AIRW----
NNGATYYADAVE  GR------FTISRDSGKNT--VYLQMNNLQPEDTAVYYCAG          RFLGYASSNAYHEALYNY-----DY  WGQGTQVTVSS
17CH1-7 k1-7  QVQLQESGGGLVQAGGSLRLSCAVSG    NTLS----RYAMG  WFRQTPGK--EREFVA    AIRW----
NNGATYYADAVE  GR------FTISRDNGKNT--VYLQMNNLQPEDTAVYYCAG          RFLGYASSNAYHEALYNY-----DY  WGQGTQVTVSS
18CH1-7 k1-8  QVQLQESGGGLVQAGGSLRLSCAVSG    NTLS----RYAMG  WFRQTPGK--EREFVA    AIRW----
NNGATYYAESVE  GR------FTISRDNGKNT--VYLQMNNLQPEDTAVYYCAG          RFLGYASSNAYHEALYNY-----DY  WGQGTQVTVSS
19CH1-7 k2-0  QVQLQESGGGLVQAGGSLRLSCAVSG    NTLS----RYAMG  WFRQTPGN--EREFVA    AIRW----
NNGATYYADSVK  GR------FTISRDSGKNT--VYLQMNNLQPEDTAVYYCAG          RFLGYASSNAYHEALYNY-----DY  WGQGTQVTVSS
20CH1-7 k2-1  QVQLQESGGGLVQAGGSLRLSCAVSG    NTLS----RYAMG  WFRQTPGN--EREFVA    AIRW----
NNGATYYAESVK  GR------FTISRDSGKNT--VYLQMNNLQPEDTAVYYCAG          RFLGYASSNAYHEALYNY-----DY  WGQGTQVTVSS
```

Fig. 1 (Cont.)

```
21CH1-7 k2-2    QVQLQESGGGLVQAGGSLRLSCAVSG      NTLS----RYAMG   WFRQTPGN--EREFVA      AIRW------
NNGATYYADSVK    GR------FTISRDTGKNT--VYLQMNNLQPEDTAVYYCAG              RFLGYASSNAYHEALYNY-----DY  WGQGTQVTVSS
22CH1-7 k2-3    QVQLQESGGGLVQAGGSLRLSCAVSG      NTLS----RYAMG   WFRQTPGN--EREFVA      AIRW------
NNGATYYAESVK    GR------FTISRDTGKNT--VYLQMNNLQPEDTAVYYCAG              RFLGYASSNAYHEALYNY-----DY  WGQGTQVTVSS
23CH1-7 k2-4    QVQLQESGGGLVQAGGSLRLSCAVSG      NTLS----RYAMG   WFRQTPGN--EREFVA      AIRW------
NNGATYYADAVK    GR------FTISRDTGKNT--VYLQMNNLQPEDTAVYYCAG              RFLGYASSNAYHEALYNY-----DY  WGQGTQVTVSS
24CH1-7 k2-5    QVQLQESGGGLVQAGGSLRLSCAVSG      NTLS----RYAMG   WFRQTPGN--EREFVA      AIRW------
NNGATYYADSVK    GR------FTISRDNGKNT--VYLQMNNLQPEDTAVYYCAG              RFLGYASSNAYHEALYNY-----DY  WGQGTQVTVSS
25CH1-7 k2-6    QVQLQESGGGLVQAGGSLRLSCAVSG      NTLS----RYAMG   WFRQTPGN--EREFVA      AIRW------
NNGATYYADAVK    GR------FTISRDTGKNT--VYLQMNNLQPEDTAVYYCAG              RFLGYASSNAYHEALYNY-----DY  WGQGTQVTVSS
26CH1-7 k2-7    QVQLQESGGGLVQAGGSLRLSCAVSG      NTLS----RYAMG   WFRQTPGN--EREFVA      AIRW------
NNGATYYADAVK    GR------FTISRDNGKNT--VYLQMNNLQPEDTAVYYCAG              RFLGYASSNAYHEALYNY-----DY  WGQGTQVTVSS
27CH1-7 k2-8    QVQLQESGGGLVQAGGSLRLSCAVSG      NTLS----RYAMG   WFRQTPGN--EREFVA      AIRW------
NNGATYYAESVK    GR------FTISRDTGKNT--VYLQMNNLQPEDTAVYYCAG              RFLGYASSNAYHEALYNY-----DY  WGQGTQVTVSS
28CH1-7 k3-0    QVQLQESGGGLVQAGGSLRLSCAVSG      NTLS----RYAMG   WFRQTPGN--EREFVA      AIRW------
NNGATYYADSVE    GR------FTISRDTGKNT--VYLQMNNLKPEDTAVYYCAG              RFLGYASSNAYHEALYNY-----DY  WGQGTQVTVSS
29CH1-7 k3-1    QVQLQESGGGLVQAGGSLRLSCAVSG      NTLS----RYAMG   WFRQTPGN--EREFVA      AIRW------
NNGATYYAESVE    GR------FTISRDSGKNT--VYLQMNNLKPEDTAVYYCAG              RFLGYASSNAYHEALYNY-----DY  WGQGTQVTVSS
30CH1-7 k3-2    QVQLQESGGGLVQAGGSLRLSCAVSG      NTLS----RYAMG   WFRQTPGN--EREFVA      AIRW------
NNGATYYADSVE    GR------FTISRDTGKNT--VYLQMNNLKPEDTAVYYCAG              RFLGYASSNAYHEALYNY-----DY  WGQGTQVTVSS
31CH1-7 k3-3    QVQLQESGGGLVQAGGSLRLSCAVSG      NTLS----RYAMG   WFRQTPGN--EREFVA      AIRW------
NNGATYYAESVE    GR------FTISRDTGKNT--VYLQMNNLKPEDTAVYYCAG              RFLGYASSNAYHEALYNY-----DY  WGQGTQVTVSS
32CH1-7 k3-4    QVQLQESGGGLVQAGGSLRLSCAVSG      NTLS----RYAMG   WFRQTPGN--EREFVA      AIRW------
NNGATYYADAVE    GR------FTISRDSGKNT--VYLQMNNLKPEDTAVYYCAG              RFLGYASSNAYHEALYNY-----DY  WGQGTQVTVSS
```

Fig. 1 (Cont.)

```
33CH1-7 k3-5   QVQLQESGGGLVQAGGSLRLSCAVSG    NTLS---RYAMG  WFRQTPGN--EREFVA  AIRW------
NNGATYYADSVE   GR------FTISRDNGKNT--VYLQMNNLKPEDTAVYYCAG         RFLGYASSNAYHEALYNY-----DY  WGQGTQVTVSS
34CH1-7 k3-6   QVQLQESGGGLVQAGGSLRLSCAVSG    NTLS---RYAMG  WFRQTPGN--EREFVA  AIRW------
NNGATYYADAVE   GR------FTISRDNGKNT--VYLQMNNLKPEDTAVYYCAG         RFLGYASSNAYHEALYNY-----DY  WGQGTQVTVSS
35CH1-7 k3-7   QVQLQESGGGLVQAGGSLRLSCAVSG    NTLS---RYAMG  WFRQTPGN--EREFVA  AIRW------
NNGATYYADAVE   GR------FTISRDTGKNT--VYLQMNNLKPEDTAVYYCAG         RFLGYASSNAYHEALYNY-----DY  WGQGTQVTVSS
36CH1-7 k3-8   QVQLQESGGGLVQAGGSLRLSCAVSG    NTLS---RYAMG  WFRQTPGN--EREFVA  AIRW------
NNGATYYAESVE   GR------FTISRDNGKNT--VYLQMNNLKPEDTAVYYCAG         RFLGYASSNAYHEALYNY-----DY  WGQGTQVTVSS
37CH1-7 k4-0   QVQLQESGGGLVQAGGSLRLSCAVSG    NTLS---RYAMG  WFRQTPGK--EREFVA  AIRW------
NNGATYYADSVK   GR------FTISRDNGKNT--VYLQMNNLQPEDTAVYYCAG         RFLGYASSNAYHEALYNY-----DY  WGQGTQVTVSS
38CH1-7 k4-1   QVQLQESGGGLVQAGGSLRLSCAVSG    NTLS---RYAMG  WFRQTPGK--EREFVA  AIRW------
NNGATYYAESVK   GR------FTISRDTGKNT--VYLQMNNLQPEDTAVYYCAG         RFLGYASSNAYHEALYNY-----DY  WGQGTQVTVSS
39CH1-7 k4-2   QVQLQESGGGLVQAGGSLRLSCAVSG    NTLS---RYAMG  WFRQTPGK--EREFVA  AIRW------
NNGATYYADSVK   GR------FTISRDTGKNT--VYLQMNNLQPEDTAVYYCAG         RFLGYASSNAYHEALYNY-----DY  WGQGTQVTVSS
40CH1-7 k4-3   QVQLQESGGGLVQAGGSLRLSCAVSG    NTLS---RYAMG  WFRQTPGK--EREFVA  AIRW------
NNGATYYAESVK   GR------FTISRDTGKNT--VYLQMNNLQPEDTAVYYCAG         RFLGYASSNAYHEALYNY-----DY  WGQGTQVTVSS
41CH1-7 k4-4   QVQLQESGGGLVQAGGSLRLSCAVSG    NTLS---RYAMG  WFRQTPGK--EREFVA  AIRW------
NNGATYYADSVK   GR------FTISRDTGKNT--VYLQMNNLQPEDTAVYYCAG         RFLGYASSNAYHEALYNY-----DY  WGQGTQVTVSS
42CH1-7 k4-5   QVQLQESGGGLVQAGGSLRLSCAVSG    NTLS---RYAMG  WFRQTPGK--EREFVA  AIRW------
NNGATYYADSVK   GR------FTISRDNGKNT--VYLQMNNLQPEDTAVYYCAG         RFLGYASSNAYHEALYNY-----DY  WGQGTQVTVSS
43CH1-7 k4-6   QVQLQESGGGLVQAGGSLRLSCAVSG    NTLS---RYAMG  WFRQTPGK--EREFVA  AIRW------
NNGATYYADAVK   GR------FTISRDNGKNT--VYLQMNNLQPEDTAVYYCAG         RFLGYASSNAYHEALYNY-----DY  WGQGTQVTVSS
44CH1-7 k4-7   QVQLQESGGGLVQAGGSLRLSCAVSG    NTLS---RYAMG  WFRQTPGK--EREFVA  AIRW------
NNGATYYADAVK   GR------FTISRDTGKNT--VYLQMNNLQPEDTAVYYCAG         RFLGYASSNAYHEALYNY-----DY  WGQGTQVTVSS
```

Fig. 1 (Cont.)

```
45CH1-7 k4-8    QVQLQESGGGLVQAGGSLRLSCAVSG      NTLS---RYAMG  WFRQTPGK--EREFVA  AIRW------
NNGATYYAESVK    GR------FTISRDNGKNT--VYLQMNNLQPEDTAVYYCAG            REFLGYASSNAYHEALYNY-----DY  WGQGTQVTVSS
46CH1-7 k5-0    QVQLQESGGGLVQAGGSLRLSCAVSG      NTLS---RYAMG  WFRQTPGK--EREFVA  AIRW------
NNGATYYADSVE    GR------FTISRDSGKNT--VYLQMNNLKPEDTAVYYCAG            REFLGYASSNAYHEALYNY-----DY  WGQGTQVTVSS
47CH1-7 k5-1    QVQLQESGGGLVQAGGSLRLSCAVSG      NTLS---RYAMG  WFRQTPGK--EREFVA  AIRW------
NNGATYYAESVE    GR------FTISRDSGKNT--VYLQMNNLKPEDTAVYYCAG            REFLGYASSNAYHEALYNY-----DY  WGQGTQVTVSS
48CH1-7 k5-2    QVQLQESGGGLVQAGGSLRLSCAVSG      NTLS---RYAMG  WFRQTPGK--EREFVA  AIRW------
NNGATYYADSVE    GR------FTISRDTGKNT--VYLQMNNLKPEDTAVYYCAG            REFLGYASSNAYHEALYNY-----DY  WGQGTQVTVSS
49CH1-7 k5-3    QVQLQESGGGLVQAGGSLRLSCAVSG      NTLS---RYAMG  WFRQTPGK--EREFVA  AIRW------
NNGATYYAESVE    GR------FTISRDTGKNT--VYLQMNNLKPEDTAVYYCAG            REFLGYASSNAYHEALYNY-----DY  WGQGTQVTVSS
50CH1-7 k5-4    QVQLQESGGGLVQAGGSLRLSCAVSG      NTLS---RYAMG  WFRQTPGK--EREFVA  AIRW------
NNGATYYADAVE    GR------FTISRDSGKNT--VYLQMNNLKPEDTAVYYCAG            REFLGYASSNAYHEALYNY-----DY  WGQGTQVTVSS
51CH1-7 k5-5    QVQLQESGGGLVQAGGSLRLSCAVSG      NTLS---RYAMG  WFRQTPGK--EREFVA  AIRW------
NNGATYYADSVE    GR------FTISRDSGKNT--VYLQMNNLKPEDTAVYYCAG            REFLGYASSNAYHEALYNY-----DY  WGQGTQVTVSS
52CH1-7 k5-6    QVQLQESGGGLVQAGGSLRLSCAVSG      NTLS---RYAMG  WFRQTPGK--EREFVA  AIRW------
NNGATYYADAVE    GR------FTISRDSGKNT--VYLQMNNLKPEDTAVYYCAG            REFLGYASSNAYHEALYNY-----DY  WGQGTQVTVSS
53CH1-7 k5-7    QVQLQESGGGLVQAGGSLRLSCAVSG      NTLS---RYAMG  WFRQTPGK--EREFVA  AIRW------
NNGATYYADSVE    GR------FTISRDSGKNT--VYLQMNNLKPEDTAVYYCAG            REFLGYASSNAYHEALYNY-----DY  WGQGTQVTVSS
54CH1-7 k5-8    QVQLQESGGGLVQAGGSLRLSCAVSG      NTLS---RYAMG  WFRQTPGK--EREFVA  AIRW------
NNGATYYADSVE    GR------FTISRDSGKNT--VYLQMNNLKPEDTAVYYCAG            REFLGYASSNAYHEALYNY-----DY  WGQGTQVTVSS
55CH1-7 k6-0    QVQLQESGGGLVQAGGSLRLSCAVSG      NTLS---RYAMG  WFRQTPGN--EREFVA  AIRW------
NNGATYYADSVK    GR------FTISRDSGKNT--VYLQMNNLKPEDTAVYYCAG            REFLGYASSNAYHEALYNY-----DY  WGQGTQVTVSS
56CH1-7 k6-1    QVQLQESGGGLVQAGGSLRLSCAVSG      NTLS---RYAMG  WFRQTPGN--EREFVA  AIRW------
NNGATYYAESVK    GR------FTISRDSGKNT--VYLQMNNLKPEDTAVYYCAG            REFLGYASSNAYHEALYNY-----DY  WGQGTQVTVSS
```

Fig. 1 (Cont.)

```
57CH1-7 k6-2     QVQLQESGGGLVQAGGSLRLSCAVSG     NTLS---RYAMG  WFRQTPGN--EREFVA  AIRW------
NNGATYYADSVK    GR------FTISRDTGKNT--VYLQMNNLKPEDTAVYYCAG                          -DY WGQGTQVTVSS
58CH1-7 k6-3     QVQLQESGGGLVQAGGSLRLSCAVSG     NTLS---RYAMG  WFRQTPGN--EREFVA  AIRW------
NNGATYYAESVK     GR------FTISRDTGKNT--VYLQMNNLKPEDTAVYYCAG                         -DY WGQGTQVTVSS
59CH1-7 k6-4     QVQLQESGGGLVQAGGSLRLSCAVSG     NTLS---RYAMG  WFRQTPGN--EREFVA  AIRW------
NNGATYYADAVK     GR------FTISRDSGKNT--VYLQMNNLKPEDTAVYYCAG                         -DY WGQGTQVTVSS
60CH1-7 k6-5     QVQLQESGGGLVQAGGSLRLSCAVSG     NTLS---RYAMG  WFRQTPGN--EREFVA  AIRW------
NNGATYYADSVK     GR------FTISRDNGKNT--VYLQMNNLKPEDTAVYYCAG                         -DY WGQGTQVTVSS
61CH1-7 k6-6     QVQLQESGGGLVQAGGSLRLSCAVSG     NTLS---RYAMG  WFRQTPGN--EREFVA  AIRW------
NNGATYYADAVK     GR------FTISRDSGKNT--VYLQMNNLKPEDTAVYYCAG                         -DY WGQGTQVTVSS
62CH1-7 k6-7     QVQLQESGGGLVQAGGSLRLSCAVSG     NTLS---RYAMG  WFRQTPGN--EREFVA  AIRW------
NNGATYYADSVK     GR------FTISRDTGKNT--VYLQMNNLKPEDTAVYYCAG                         -DY WGQGTQVTVSS
63CH1-7 k6-8     QVQLQESGGGLVQAGGSLRLSCAVSG     NTLS---RYAMG  WFRQTPGN--EREFVA  AIRW------
NNGATYYAESVK     GR------FTISRDSGKNT--VYLQMNNLKPEDTAVYYCAG                         -DY WGQGTQVTVSS
64CH1-7 k7-0     QVQLQESGGGLVQAGGSLRLSCAVSG     NTLS---RYAMG  WFRQTPGK--EREFVA  AIRW------
NNGATYYADSVK     GR------FTISRDTGKNT--VYLQMNNLKPEDTAVYYCAG                         -DY WGQGTQVTVSS
65CH1-7 k7-1     QVQLQESGGGLVQAGGSLRLSCAVSG     NTLS---RYAMG  WFRQTPGK--EREFVA  AIRW------
NNGATYYAESVK     GR------FTISRDSGKNT--VYLQMNNLKPEDTAVYYCAG                         -DY WGQGTQVTVSS
66CH1-7 k7-2     QVQLQESGGGLVQAGGSLRLSCAVSG     NTLS---RYAMG  WFRQTPGK--EREFVA  AIRW------
NNGATYYADSVK     GR------FTISRDTGKNT--VYLQMNNLKPEDTAVYYCAG                         -DY WGQGTQVTVSS
67CH1-7 k7-3     QVQLQESGGGLVQAGGSLRLSCAVSG     NTLS---RYAMG  WFRQTPGK--EREFVA  AIRW------
NNGATYYAESVK     GR------FTISRDSGKNT--VYLQMNNLKPEDTAVYYCAG                         -DY WGQGTQVTVSS
68CH1-7 k7-4     QVQLQESGGGLVQAGGSLRLSCAVSG     NTLS---RYAMG  WFRQTPGK--EREFVA  AIRW------
NNGATYYADAVK     GR------FTISRDSGKNT--VYLQMNNLKPEDTAVYYCAG                         -DY WGQGTQVTVSS
```

Fig. 1 (Cont.)

```
69CH1-7 k7-5    QVQLQESGGGLVQAGGSLRLSCAVSG      NTLS----RYAMG   WFRQTPGK--EREFVA    AIRW------
NNGATYYADSVK    GR------FTISRDNGKNT--VYLQMNNLKPEDTAVYYCAG              RFLGYASSNAYHEALYNY-----DY   WGQGTQVTVSS
70CH1-7 k7-6    QVQLQESGGGLVQAGGSLRLSCAVSG      NTLS----RYAMG   WFRQTPGK--EREFVA    AIRW------
NNGATYYADAVK    GR------FTISRDNGKNT--VYLQMNNLKPEDTAVYYCAG              RFLGYASSNAYHEALYNY-----DY   WGQGTQVTVSS
71CH1-7 k7-7    QVQLQESGGGLVQAGGSLRLSCAVSG      NTLS----RYAMG   WFRQTPGK--EREFVA    AIRW------
NNGATYYADAVK    GR------FTISRDTGKNT--VYLQMNNLKPEDTAVYYCAG              RFLGYASSNAYHEALYNY-----DY   WGQGTQVTVSS
72CH1-7 k7-8    QVQLQESGGGLVQAGGSLRLSCAVSG      NTLS----RYAMG   WFRQTPGK--EREFVA    AIRW------
NNGATYYAESVK    GR------FTISRDNGKNT--VYLQMNNLKPEDTAVYYCAG              RFLGYASSNAYHEALYNY-----DY   WGQGTQVTVSS
73CH1-7 k8-0    QVQLQESGGGLVQAGGSLRLSCAVSG      NTLS----RYAMG   WFRQTPGN--EREFVA    AIRW------
NNGATYYADSVK    GR------FTISRDSGRNT--VYLQMNNLKPEDTAVYYCAG              RFLGYASSNAYHEALYNY-----DY   WGQGTQVTVSS
74CH1-7 k8-1    QVQLQESGGGLVQAGGSLRLSCAVSG      NTLS----RYAMG   WFRQTPGN--EREFVA    AIRW------
NNGATYYAESVK    GR------FTISRDTGRNT--VYLQMNNLKPEDTAVYYCAG              RFLGYASSNAYHEALYNY-----DY   WGQGTQVTVSS
75CH1-7 k8-2    QVQLQESGGGLVQAGGSLRLSCAVSG      NTLS----RYAMG   WFRQTPGN--EREFVA    AIRW------
NNGATYYADSVK    GR------FTISRDTGRNT--VYLQMNNLKPEDTAVYYCAG              RFLGYASSNAYHEALYNY-----DY   WGQGTQVTVSS
76CH1-7 k8-3    QVQLQESGGGLVQAGGSLRLSCAVSG      NTLS----RYAMG   WFRQTPGN--EREFVA    AIRW------
NNGATYYAESVK    GR------FTISRDTGRNT--VYLQMNNLKPEDTAVYYCAG              RFLGYASSNAYHEALYNY-----DY   WGQGTQVTVSS
77CH1-7 k8-4    QVQLQESGGGLVQAGGSLRLSCAVSG      NTLS----RYAMG   WFRQTPGN--EREFVA    AIRW------
NNGATYYADSVK    GR------FTISRDNGRNT--VYLQMNNLKPEDTAVYYCAG              RFLGYASSNAYHEALYNY-----DY   WGQGTQVTVSS
78CH1-7 k8-5    QVQLQESGGGLVQAGGSLRLSCAVSG      NTLS----RYAMG   WFRQTPGN--EREFVA    AIRW------
NNGATYYADSVK    GR------FTISRDNGRNT--VYLQMNNLKPEDTAVYYCAG              RFLGYASSNAYHEALYNY-----DY   WGQGTQVTVSS
79CH1-7 k8-6    QVQLQESGGGLVQAGGSLRLSCAVSG      NTLS----RYAMG   WFRQTPGN--EREFVA    AIRW------
NNGATYYADAVK    GR------FTISRDNGRNT--VYLQMNNLKPEDTAVYYCAG              RFLGYASSNAYHEALYNY-----DY   WGQGTQVTVSS
80CH1-7 k8-7    QVQLQESGGGLVQAGGSLRLSCAVSG      NTLS----RYAMG   WFRQTPGN--EREFVA    AIRW------
NNGATYYADAVK    GR------FTISRDTGRNT--VYLQMNNLKPEDTAVYYCAG              RFLGYASSNAYHEALYNY-----DY   WGQGTQVTVSS
```

Fig. 1 (Cont.)

```
81CH1-7_k8-8  QVQLQESGGGLVQAGGSLRLSCAVSG          NTLS---RYAMG  WFRQTPGN--EREFVA  AIRW-----
              NNGATYYAESVK  GR------FTISRDNGRNT--VYLQMNNLKPEDTAVYYCAG        --DY  WGQGTQVTVSS
82 CH1-1      QVQLQESGGGLVQAGGSLRLSCAVSG          NTLS---RYAMG  WFRQAPGN--EREFVA  AIRW-----
              NNGNTYYADSVK  GR------FTISRDSAKNT--VFLQMNSLQPEDTAVYFCAA        --DY  WGQGTQVTVSS
83 CH1-2      QVQLQDSGGGLVQAGGSLRLSCAVSG          NTLS---RYAMG  RFLPYASSNAYHEALYNY--DY  WGQGTQVTVSS
              NNGNTYYADSVE  GR------FTISRDSAKNT--VYLQMNSLQPEDTAVYYCAA                AIRW-----
84 CH1-3      QVQLQDSGGGLVQAGGSLRLSCAVSG          NTLS---RYAMG  WFRQAPGN--EREFVA  AIRW-----
              NNGNTYYADSVE  GR------FTISRDSAKNT--VYLQMNSLQPEDTAVYYCAA        --DY  WGQGTQVTVSS
85 CH1-4      QVQLQESGGGLVQAGGSLRLSCAVSG          NTLS---RYAMG  RFLGYASSNAYHEALYNY--DY  WGQGTQVTVSS
              NNGATYYADSVE  GR------FTISRDSGKNT--VYLQMNSLQPEDTAVYYCAG                AIRW-----
86 CH1-5      QVQLQDSGGGSVQAGGSLRLSCAVSG          NTLS----QYAMG WFRQAPGN--EREFVA  AIRW-----
              NNGNTYYADSVE  GR------FTISRDSAKNT--VFLQMNSLQPDDTAVYFCAA        --DY  WGQGTQVTVSS
87 CH1-6      QVQLQESGGGSVQAGASLRLSCEVSG          NTLS---RYAMG  RFLPYASSNAYHESLYNY--DY  WGQGTQVTVSS
              TNGNTYYADSVE  GR------FTISRSAKKT--VYLQMNSLQAEDTAIYYCAA                 AIRW-----
88 CH1-8      QVQLQESGGGLVQAGGSLRLSCAVSG          NTLS---RYAMG  WFRQVPGH--KREFVA  AIRW-----
              NNGNTYYADSVE  GR------FTISRYSAKNL--VYLQMNSLQAEDTAIYYCAA        --DY  WGQGTQVTVSS
89 CH1-9      QVQLQESGGGLVQAGGSLRLSCAVSG          NTLS---RYAMG  RFLPYASSNAYHEALYNY--DY  WGQGTQVTVSS
              NNGATYYADSVK  GR------FTISRDSAKNT--VYLQMNSLQPEDTAVYYCAS                AIRW-----
90_13_A12     QVQLQDSGGGLVQAGGSLRLSCAVSG          NTLS---RYATG  WFRQAPGN--EREFVA  AIRW-----
              NNGNTYYADSVE  GR------FTIARDSARDT--VYLQMNNLQPEDTAVYYCAA        --DY  WGQGTQVTVSS
91_12_A9      QVQLQESGGGSVQAEGSLRLSCAVSG          NTLS---RYAMG  RFLPYASSNAYHEALYNY--DY  WGQGTQVTVSS
              NSGHTYYADSVE  GR------FTISRDSAKNT--VYLQMDMLQPEDTAVYYCAA                AIRW-----
92_07_E8      QVQLQDSGGGLVQAGGSLTLSCVVSG          NTLS---RYAMG  WFRQAPGN--EREFVA  AIRW-----
              ENGNTYYADSVE  GR------FTISRDSAKNT--VYLQMNSLQPEDTAVYYCAA  RFLPYASSNAYHETLYNY--DY  WGQGTQVTVSS
```

Fig. 1 (Cont.)

```
93_10_F1    QVQLQESGGGLVQAGGSLRLSCAVSG    NTLS----QYAMG  WFRQAPGN--EREFVA  AIRW-----
NNGNTYYADSVE GR------FTISRDSAKNT--VYLQMNSLQPEDTAVYYCAA        RFLPYASSNAYHETLYNY-----DY WGQGTQVTVSS
94_10_F9    QVQLQESGGGLVQAGGSLRLSCAVSG    NTLS----RYAMG  WFRQVLGN--EREFVA  AIRW-----
NNGNTYYADSVE GR------FTISRDSAKNT--VYLQMNSLQPEDTAVYYCAA        RFLPYASSNAYHESLYNY-----DY WGQGTQVTVSS
95_07_F7    QVQLQESGGGLVQAGGSLRLSCAVSG    NTLS----PYAMG  WFRQTPRN--EREFVA  PIRW-----
NNGNTYYADSVE GR------FTISRDSAKNT--VYLQMNSLQPEDTAVYYCAA        RFLPYASSNAYHEALYNY-----DY WGQGTQVTVSS
96_CH1-7k1-9  QVQLQESGGGLVQAGGSLRLSCAVSG    NTLS----RYAMG  WFRQTPGK--EREFVA  AIRW-----
NNGATYYADSVE GR------FTISRDNAKNT--VYLQMNLQPEDTAVYYCAG        RFLGYASSNAYHEALYNY-----DY WGQGTQVTVSS
97_CH1-7k1-10 QVQLQESGGGLVQAGGSLRLSCAVSG    NTLS----RYAMG  WFRQTPGK--EREFVA  AIRW-----
NNGATYYAESVE GR------FTISRDNAKNT--VYLQMNLQPEDTAVYYCAG        RFLGYASSNAYHEALYNY-----DY WGQGTQVTVSS
98_CH1-7k1-11 QVQLQESGGGLVQAGGSLRLSCAVSG    NTLS----RYAMG  WFRQTPGK--EREFVA  AIRW-----
NNGATYYAESVE GR------FTISRDNAKNT--VYLQMNLQPEDTAVYYCAG        RFLGYASSNAYHEALYNY-----DY WGQGTQVTVSS
99_CH1-7k1-12 QVQLQESGGGLVQAGGSLRLSCAVSG    NTLS----RYAMG  WFRQTPGK--EREFVA  AIRW-----
NNAATYYADSVE GR------FTISRDTGKNT--VYLQMNNLQPEDTAVYYCAG       RFLGYASSNAYHEALYNY-----DY WGQGTQVTVSS
100CH1-7k1-13 QVQLQESGGGLVQAGGSLRLSCAVSG    NTLS----RYAMG  WFRQTPGK--EREFVA  AIRW-----
NNAATYYAESVE GR------FTISRDTGKNT--VYLQMNNLQPEDTAVYYCAG       RFLGYASSNAYHEALYNY-----DY WGQGTQVTVSS
101CH1-7k1-14 QVQLQESGGGLVQAGGSLRLSCAVSG    NTLS----RYAMG  WFRQTPGK--EREFVA  AIRW-----
NNAATYYADSVE GR------FTISRDTGKNT--VYLQMNNLQPEDTAVYYCAG       RFLGYASSNAYHEALYNY-----DY WGQGTQVTVSS
102CH1-7k1-15 QVQLQESGGGLVQAGGSLRLSCAVSG    NTLS----RYAMG  WFRQTPGK--EREFVA  AIRW-----
NNAATYYAESVE GR------FTISRDSGKNT--VYLQMNNLQPEDTAVYYCAG       RFLGYASSNAYHEALYNY-----DY WGQGTQVTVSS
103CH1-7k1-16 QVQLQESGGGLVQAGGSLRLSCAVSG    NTLS----RYAMG  WFRQTPGK--EREFVA  AIRW-----
NNAATYYADAVE GR------FTISRDSGKNT--VYLQMNNLQPEDTAVYYCAG       RFLGYASSNAYHEALYNY-----DY WGQGTQVTVSS
104CH1-7k1-17 QVQLQESGGGLVQAGGSLRLSCAVSG    NTLS----RYAMG  WFRQTPGK--EREFVA  AIRW-----
NNAATYYADSVE GR------FTISRDNAKNT--VYLQMNNLQPEDTAVYYCAG       RFLGYASSNAYHEALYNY-----DY WGQGTQVTVSS
```

Fig. 1 (Cont.)

```
105CH1-7k1-18  QVQLQESGGGLVQAGGSLRLSCAVSG    NTLS---RYAMG  WFRQTPGK--EREFVA  AIRW------
NNAATYYADAVE   GR------FTISRDNAKNT--VYLQMNNLQPEDTAVYYCAG          RFLGYASSNAYHEALYNY-----DY  WGQGTQVTVSS
106CH1-7k1-19  QVQLQESGGGLVQAGGSLRLSCAVSG    NTLS---RYAMG  WFRQTPGK--EREFVA  AIRW------
NNAATYYADAVE   GR------FTISRDTGKNT--VYLQMNNLQPEDTAVYYCAG          RFLGYASSNAYHEALYNY-----DY  WGQGTQVTVSS
107CH1-7k1-20  QVQLQESGGGLVQAGGSLRLSCAVSG    NTLS---RYAMG  WFRQTPGK--EREFVA  AIRW------
NNAATYYAESVE   GR------FTISRDNAKNT--VYLQMNNLQPEDTAVYYCAG          RFLGYASSNAYHEALYNY-----DY  WGQGTQVTVSS
108CH1-7k1-21  QVQLQESGGGLVQAGGSLRLSCAVSG    NTLS---RYAMG  WFRQTPGK--EREFVA  AIRW------
NEGATYYADSVE   GR------FTISRDSGKNT--VYLQMNNLQPEDTAVYYCAG          RFLGYASSNAYHEALYNY-----DY  WGQGTQVTVSS
109CH1-7k1-22  QVQLQESGGGLVQAGGSLRLSCAVSG    NTLS---RYAMG  WFRQTPGK--EREFVA  AIRW------
NEGATYYAESVE   GR------FTISRDSGKNT--VYLQMNNLQPEDTAVYYCAG          RFLGYASSNAYHEALYNY-----DY  WGQGTQVTVSS
110CH1-7k1-23  QVQLQESGGGLVQAGGSLRLSCAVSG    NTLS---RYAMG  WFRQTPGK--EREFVA  AIRW------
NEGATYYAESVE   GR------FTISRDTGKNT--VYLQMNNLQPEDTAVYYCAG          RFLGYASSNAYHEALYNY-----DY  WGQGTQVTVSS
111CH1-7k1-24  QVQLQESGGGLVQAGGSLRLSCAVSG    NTLS---RYAMG  WFRQTPGK--EREFVA  AIRW------
NEGATYYADSVE   GR------FTISRDNAKNT--VYLQMNNLQPEDTAVYYCAG          RFLGYASSNAYHEALYNY-----DY  WGQGTQVTVSS
112CH1-7k1-25  QVQLQESGGGLVQAGGSLRLSCAVSG    NTLS---RYAMG  WFRQTPGK--EREFVA  AIRW------
NEGATYYAESVE   GR------FTISRDSGKNT--VYLQMNNLQPEDTAVYYCAG          RFLGYASSNAYHEALYNY-----DY  WGQGTQVTVSS
113CH1-7k1-26  QVQLQESGGGLVQAGGSLRLSCAVSG    NTLS---RYAMG  WFRQTPGK--EREFVA  AIRW------
NEGATYYADSVE   GR------FTISRDNAKNT--VYLQMNNLQPEDTAVYYCAG          RFLGYASSNAYHEALYNY-----DY  WGQGTQVTVSS
114CH1-7k1-27  QVQLQESGGGLVQAGGSLRLSCAVSG    NTLS---RYAMG  WFRQTPGK--EREFVA  AIRW------
NEGATYYADSVE   GR------FTISRDTGKNT--VYLQMNNLQPEDTAVYYCAG          RFLGYASSNAYHEALYNY-----DY  WGQGTQVTVSS
115CH1-7k1-28  QVQLQESGGGLVQAGGSLRLSCAVSG    NTLS---RYAMG  WFRQTPGK--EREFVA  AIRW------
NEGATYYADAVE   GR------FTISRDTGKNT--VYLQMNNLQPEDTAVYYCAG          RFLGYASSNAYHEALYNY-----DY  WGQGTQVTVSS
116CH1-7k1-29  QVQLQESGGGLVQAGGSLRLSCAVSG    NTLS---RYAMG  WFRQTPGK--EREFVA  AIRW------
NEGATYYAESVE   GR------FTISRDNAKNT--VYLQMNNLQPEDTAVYYCAG          RFLGYASSNAYHEALYNY-----DY  WGQGTQVTVSS
```

*Fig. 1 (Cont.)*

```
117CH1-7k3-9   QVQLQESGGGLVQAGGSLRLSCAVSG      NTLS---RYAMG    WFRQTPGN--EREFVA    AIRW----
NNGATYYADSVE    GR------FTISRDNAKNT--VYLQMNNLKPEDTAVYYCAG                          --DY WGQGTQVTVSS
118CH1-7k3-10  QVQLQESGGGLVQAGGSLRLSCAVSG      NTLS---RYAMG    RFLGYASSNAYHEALYNY  AIRW----
NNGATYYADAVE    GR------FTISRDNAKNT--VYLQMNNLKPEDTAVYYCAG                          --DY WGQGTQVTVSS
119CH1-7k3-11  QVQLQESGGGLVQAGGSLRLSCAVSG      NTLS---RYAMG    WFRQTPGN--EREFVA    AIRW----
NNGATYYADSVE    GR------FTISRDNAKNT--VYLQMNNLKPEDTAVYYCAG                          --DY WGQGTQVTVSS
120CH1-7k3-12  QVQLQESGGGLVQAGGSLRLSCAVSG      NTLS---RYAMG    RFLGYASSNAYHEALYNY  AIRW----
NNAATYYAESVE    GR------FTISRDNAKNT--VYLQMNNLKPEDTAVYYCAG                          --DY WGQGTQVTVSS
121CH1-7k3-13  QVQLQESGGGLVQAGGSLRLSCAVSG      NTLS---RYAMG    WFRQTPGN--EREFVA    AIRW----
NNAATYYADSVE    GR------FTISRDSGKNT--VYLQMNNLKPEDTAVYYCAG                          --DY WGQGTQVTVSS
122CH1-7k3-14  QVQLQESGGGLVQAGGSLRLSCAVSG      NTLS---RYAMG    RFLGYASSNAYHEALYNY  AIRW----
NNAATYYAESVE    GR------FTISRDTGKNT--VYLQMNNLKPEDTAVYYCAG                          --DY WGQGTQVTVSS
123CH1-7k3-15  QVQLQESGGGLVQAGGSLRLSCAVSG      NTLS---RYAMG    WFRQTPGN--EREFVA    AIRW----
NNAATYYADSVE    GR------FTISRDTGKNT--VYLQMNNLKPEDTAVYYCAG                          --DY WGQGTQVTVSS
124CH1-7k3-16  QVQLQESGGGLVQAGGSLRLSCAVSG      NTLS---RYAMG    RFLGYASSNAYHEALYNY  AIRW----
NNAATYYADAVE    GR------FTISRDTGKNT--VYLQMNNLKPEDTAVYYCAG                          --DY WGQGTQVTVSS
125CH1-7k3-17  QVQLQESGGGLVQAGGSLRLSCAVSG      NTLS---RYAMG    WFRQTPGN--EREFVA    AIRW----
NNAATYYADSVE    GR------FTISRDNAKNT--VYLQMNNLKPEDTAVYYCAG                          --DY WGQGTQVTVSS
126CH1-7k3-18  QVQLQESGGGLVQAGGSLRLSCAVSG      NTLS---RYAMG    RFLGYASSNAYHEALYNY  AIRW----
NNAATYYAESVE    GR------FTISRDNAKNT--VYLQMNNLKPEDTAVYYCAG                          --DY WGQGTQVTVSS
127CH1-7k3-19  QVQLQESGGGLVQAGGSLRLSCAVSG      NTLS---RYAMG    WFRQTPGN--EREFVA    AIRW----
NNAATYYADAVE    GR------FTISRDTGKNT--VYLQMNNLKPEDTAVYYCAG                          --DY WGQGTQVTVSS
128CH1-7k3-20  QVQLQESGGGLVQAGGSLRLSCAVSG      NTLS---RYAMG    RFLGYASSNAYHEALYNY  AIRW----
NNAATYYAESVE    GR------FTISRDNAKNT--VYLQMNNLKPEDTAVYYCAG                          --DY WGQGTQVTVSS
```

Fig. 1 (Cont.)

```
129CH1-7k3-21   QVQLQESGGGLVQAGGSLRLSCAVSG      NTLS---RYAMG   WFRQTPGN--EREFVA   AIRW------DY  WGQGTQVTVSS
NEGATYYADSVE    GR------FTISRDSGKNT--VYLQMNNLKPEDTAVYYCAG
130CH1-7k3-22   QVQLQESGGGLVQAGGSLRLSCAVSG      NTLS---RYAMG   RFLGYASSNAYHEALYNY--DY  WGQGTQVTVSS
NEGATYYAESVE    GR------FTISRDSGKNT--VYLQMNNLKPEDTAVYYCAG
131CH1-7k3-23   QVQLQESGGGLVQAGGSLRLSCAVSG      NTLS---RYAMG   WFRQTPGN--EREFVA   AIRW------DY  WGQGTQVTVSS
NEGATYYADSVE    GR------FTISRDTGKNT--VYLQMNNLKPEDTAVYYCAG
132CH1-7k3-24   QVQLQESGGGLVQAGGSLRLSCAVSG      NTLS---RYAMG   RFLGYASSNAYHEALYNY--DY  WGQGTQVTVSS
NEGATYYAESVE    GR------FTISRDTGKNT--VYLQMNNLKPEDTAVYYCAG
133CH1-7k3-25   QVQLQESGGGLVQAGGSLRLSCAVSG      NTLS---RYAMG   WFRQTPGN--EREFVA   AIRW------DY  WGQGTQVTVSS
NEGATYYADAVE    GR------FTISRDNAKNT--VYLQMNNLKPEDTAVYYCAG
134CH1-7k3-26   QVQLQESGGGLVQAGGSLRLSCAVSG      NTLS---RYAMG   RFLGYASSNAYHEALYNY--DY  WGQGTQVTVSS
NEGATYYAESVE    GR------FTISRDNAKNT--VYLQMNNLKPEDTAVYYCAG
135CH1-7k3-27   QVQLQESGGGLVQAGGSLRLSCAVSG      NTLS---RYAMG   WFRQTPGN--EREFVA   AIRW------DY  WGQGTQVTVSS
NEGATYYADAVE    GR------FTISRDNAKNT--VYLQMNNLKPEDTAVYYCAG
136CH1-7k3-28   QVQLQESGGGLVQAGGSLRLSCAVSG      NTLS---RYAMG   RFLGYASSNAYHEALYNY--DY  WGQGTQVTVSS
NEGATYYAESVE    GR------FTISRDTGKNT--VYLQMNNLKPEDTAVYYCAG
137CH1-7k3-29   QVQLQESGGGLVQAGGSLRLSCAVSG      NTLS---RYAMG   WFRQTPGN--EREFVA   AIRW------DY  WGQGTQVTVSS
NEGATYYADAVE    GR------FTISRDNAKNT--VYLQMNNLKPEDTAVYYCAG
138CH1-7k5-9    QVQLQESGGGLVQAGGSLRLSCAVSG      NTLS---RYAMG   RFLGYASSNAYHEALYNY--DY  WGQGTQVTVSS
NEGATYYAESVE    GR------FTISRDNAKNT--VYLQMNNLKPEDTAVYYCAG
NNGATYYADAVE    GR------FTISRDNAKNT--VYLQMNNLKPEDTAVYYCAG
139CH1-7k5-10   QVQLQESGGGLVQAGGSLRLSCAVSG      NTLS---RYAMG   WFRQTPGK--EREFVA   AIRW------DY  WGQGTQVTVSS
NNGATYYADAVE    GR------FTISRDNAKNT--VYLQMNNLKPEDTAVYYCAG
140CH1-7k5-11   QVQLQESGGGLVQAGGSLRLSCAVSG      NTLS---RYAMG   WFRQTPGK--EREFVA   AIRW------DY  WGQGTQVTVSS
NNGATYYAESVE    GR------FTISRDNAKNT--VYLQMNNLKPEDTAVYYCAG
```

Fig. 1 (Cont.)

```
141CH1-7k5-12  QVQLQESGGGLVQAGGSLRLSCAVSG       NTLS----RYAMG  WFRQTPGK--EREFVA    AIRW------
NNAATYYADSVE    GR------FTISRDSGKNT--VYLQMNNLKPEDTAVYYCAG                         DY WGQGTQVTVSS
142CH1-7k5-13  QVQLQESGGGLVQAGGSLRLSCAVSG       NTLS----RYAMG  RFLGYASSNAYHEALYNY----DY WGQGTQVTVSS
NNAATYAESVE     GR------FTISRDSGKNT--VYLQMNNLKPEDTAVYYCAG                         
143CH1-7k5-14  QVQLQESGGGLVQAGGSLRLSCAVSG       NTLS----RYAMG  WFRQTPGK--EREFVA    AIRW------
NNAATYYADSVE    GR------FTISRDTGKNT--VYLQMNNLKPEDTAVYYCAG                         DY WGQGTQVTVSS
144CH1-7k5-15  QVQLQESGGGLVQAGGSLRLSCAVSG       NTLS----RYAMG  RFLGYASSNAYHEALYNY----DY WGQGTQVTVSS
NNAATYAESVE     GR------FTISRDTGKNT--VYLQMNNLKPEDTAVYYCAG                         
145CH1-7k5-16  QVQLQESGGGLVQAGGSLRLSCAVSG       NTLS----RYAMG  WFRQTPGK--EREFVA    AIRW------
NNAATYYADAVE    GR------FTISRDSGKNT--VYLQMNNLKPEDTAVYYCAG                         DY WGQGTQVTVSS
146CH1-7k5-17  QVQLQESGGGLVQAGGSLRLSCAVSG       NTLS----RYAMG  RFLGYASSNAYHEALYNY----DY WGQGTQVTVSS
NNAATYAEAVE     GR------FTISRDSGKNT--VYLQMNNLKPEDTAVYYCAG                         
147CH1-7k5-18  QVQLQESGGGLVQAGGSLRLSCAVSG       NTLS----RYAMG  WFRQTPGK--EREFVA    AIRW------
NNAATYYADAVE    GR------FTISRDNAKNT--VYLQMNNLKPEDTAVYYCAG                         DY WGQGTQVTVSS
148CH1-7k5-19  QVQLQESGGGLVQAGGSLRLSCAVSG       NTLS----RYAMG  RFLGYASSNAYHEALYNY----DY WGQGTQVTVSS
NNAATYAEAVE     GR------FTISRDNAKNT--VYLQMNNLKPEDTAVYYCAG                         
149CH1-7k5-20  QVQLQESGGGLVQAGGSLRLSCAVSG       NTLS----RYAMG  WFRQTPGK--EREFVA    AIRW------
NNAATYYADSVE    GR------FTISRDTGKNT--VYLQMNNLKPEDTAVYYCAG                         DY WGQGTQVTVSS
150CH1-7k5-21  QVQLQESGGGLVQAGGSLRLSCAVSG       NTLS----RYAMG  RFLGYASSNAYHEALYNY----DY WGQGTQVTVSS
NEGATYYADSVE    GR------FTISRDSGKNT--VYLQMNNLKPEDTAVYYCAG                         
151CH1-7k5-22  QVQLQESGGGLVQAGGSLRLSCAVSG       NTLS----RYAMG  WFRQTPGK--EREFVA    AIRW------
NEGATYAESVE     GR------FTISRDSGKNT--VYLQMNNLKPEDTAVYYCAG                         DY WGQGTQVTVSS
152CH1-7k5-23  QVQLQESGGGLVQAGGSLRLSCAVSG       NTLS----RYAMG  RFLGYASSNAYHEALYNY----DY WGQGTQVTVSS
NEGATYYADSVE    GR------FTISRDTGKNT--VYLQMNNLKPEDTAVYYCAG                         
```

Fig. 1 (Cont.)

```
153CH1-7k5-24  QVQLQESGGGLVQAGGSLRLSCAVSG    NTLS----RYAMG  WFRQTPGK--EREFVA    AIRW------
               GR------FTISRDTGKNT--VYLQMNNLKPEDTAVYYCAG
               NEGATYYAESVE  RFLGYASSNAYHEALYNY-----DY  WGQGTQVTVSS
154CH1-7k5-25  QVQLQESGGGLVQAGGSLRLSCAVSG    NTLS----RYAMG  WFRQTPGK--EREFVA    AIRW------
               GR------FTISRDSGKNT--VYLQMNNLKPEDTAVYYCAG
               NEGATYYADAVE  RFLGYASSNAYHEALYNY-----DY  WGQGTQVTVSS
155CH1-7k5-26  QVQLQESGGGLVQAGGSLRLSCAVSG    NTLS----RYAMG  WFRQTPGK--EREFVA    AIRW------
               GR------FTISRDNAKNT--VYLQMNNLKPEDTAVYYCAG
               NEGATYYADSVE  RFLGYASSNAYHEALYNY-----DY  WGQGTQVTVSS
156CH1-7k5-27  QVQLQESGGGLVQAGGSLRLSCAVSG    NTLS----RYAMG  WFRQTPGK--EREFVA    AIRW------
               GR------FTISRDNAKNT--VYLQMNNLKPEDTAVYYCAG
               NEGATYYADAVE  RFLGYASSNAYHEALYNY-----DY  WGQGTQVTVSS
157CH1-7k5-28  QVQLQESGGGLVQAGGSLRLSCAVSG    NTLS----RYAMG  WFRQTPGK--EREFVA    AIRW------
               GR------FTISRDTGKNT--VYLQMNNLKPEDTAVYYCAG
               NEGATYYADAVE  RFLGYASSNAYHEALYNY-----DY  WGQGTQVTVSS
158CH1-7k5-29  QVQLQESGGGLVQAGGSLRLSCAVSG    NTLS----RYAMG  WFRQTPGK--EREFVA    AIRW------
               GR------FTISRDNAKNT--VYLQMNNLKPEDTAVYYCAG
               NEGATYYAESVE  RFLGYASSNAYHEALYNY-----DY  WGQGTQVTVSS
```

CDR-I

159     NTLSRYAMG
160     NTLSQYAMG
161     NTLSRYATG
162     NTLSPYAMG

CDR-II

163     AIRWNNGATYYADSVE
164     AIRWNNGATYYAESVE
165     AIRWNNGATYYADAVE
166     AIRWNNGATYYADSVK
167     AIRWNNGATYYAESVK
168     AIRWNNGATYYADAVK
169     AIRWNNGNTYYADSVK
170     AIRWNNGNTYYADSVE
171     AIRWNNGATYYADSVE
172     AIRWTNGNTYYADSVE
173     AIRWNSGHTYYADSVE
174     AIRWENGNTYYADSVE
175     PIRWNNGNTYYADSVE
176     AIRWNNAATYYADSVE
177     AIRWNNAATYYAESVE
178     AIRWNNAATYYADAVE
179     AIRWNEGATYYADSVE
180     AIRWNEGATYYAESVE
181     AIRWNEGATYYADAVE

CDR-III

182     RFLGYASSNAYHEALYNYDY
183     RFLPYASSNAYHEALYNYDY
184     RFLPYASSNAYHESLYNYDY
185     RFLPYASSNAYHETLYNYDY

```
Guin.Pig IgG2   71  ARTTAPSVFPLAASCVD--TSGSMMTLGCLVKGYFFPEPVTV-KW----
                    NSGALTSG-VHTFPAVLQS--GLYSLTSMVTVPSSQKK-----ATCNVAHPASSTKV-DKTV
Horse IgG1      79  ASTTAPKVFALAPGCGT--TSDSTVALGCLVSGYFPEPVKV-SW----
                    NSGSLTSG-VHTFPSVLQS-SGFYSLSSMVTVPASTWTS--E-TYICNVHAASNFKV-DKRI
---------------------------------------------------------------
Rabbit IgG      67  GQPKAPSVFPLAPCCGD--TPSSTVTLGCLVKGYLPEPVTV-TW----
                    NSGTLTNG-VRTFPSVRQS-SGLYSLSSVVSVTSS------SQPVTCNVAHPATNTKV-DKTV     NEGATIVE
Swine IgG1      69  APKTAPSVYPLAPCGRD--TSGPNVALGCLASSYFPEPVTV-TW----
                    NSGALTSG-VHTFPSVLQP-SGLYSLSSMVTVPASSLSS--K-SYTCNVNHPATTTKV-DKRV
Swine IgG2      69  APKTAPSVYPLAPCGRD--VSGPNVALGCLASSYFPEPVTV-TW----
                    NSGALTSG-VHTFPSVLQP-SGLYSLSSMVTVPASSLSS--K-SYTCNVNHPATTTKV-DKRV
Bovine IgG1     68  ASTTAPKVYPLSSCCGD--KSSSTVTLGCLVSSYMPEPVTV-TW----
                    NSGALKSG-VHTFPAVLQS-SGLYSLSSMVTVPASSSG---TQTFTCNVAHPASSTKV-DK
Bovine IgG2     68  ASTTAPKVYPLSSCCGD--KSSSGVTLGCLVSSYMPEPVTV-TW----
                    NSGALKSG-VHTFPSVLQS-SGLYSLSSMVTVPASSSG---TQTFTCNVAHPASSTKV-DK
Sheep IgG1      69  ASTTPPKVYPLTSCCGD--TSSSIVTLGCLVSSYMPEPVTV-TW----
                    NSGALTSG-VHTFPAILQS-SGLYSLSSVVTVPASTSG---AQTFICNVAHPASSTKV-DKRV
Goat IgG1       69  ASTTPPKVYPLTSCCGD--TSSSIVTLGCLVSSYMPEPVTV-TW----
                    NSGALTSG-VHTFPAVLQS-SGLYSLSSMVTVPASTSG---AQTFICNVAHPASSTKV-DKRV
Lama IgG1a      65  ASTKAPSVYPLTARCGD--TPGSTVAFGCLVWGYIPEPVTV-TW----
                    NSGALSSG-VHTFPSVFMS-SGLYTLSSLVTMPASSST---GKTFICNVAHPASSTKV-DKRV
Lama IgG1b      66  ASTKAPSVYPLTARCGD--TPGSTVAFGCLVWGYIPEPVTV-TW----
                    NSGALSSG-VHTFPSVFMS-SGLYSLSSLVTLPTSSST---GKTFICNVAHPASSTKV-DKRV
```

Fig. 2 (Cont.)

```
Rat IgG1    67   AETTAPSVYPLAPGTAL--KSNSMVTLGCLVKGYFPEPVTV--TW----
NSGALSSG-VHTFPAVLQ---SGLYTLTSSVTVPSS--TWP-SQTVT-CNVAHPASSTKV-DKKI
Rat IgG2a   66   AETTAPSVYPLAPGTAL--KSNSMVTLGCLVKGYFPEPVTV--TW----
NSGALSSG-VHTFPAVLQ---SGLYTLTSSVTVPSS--TWS-SQAVT-CNVAHPASSTKV-DKKI
Rat IgG2b   66   AQTTAPSVYPLAPGCGD--TTSSTVTLGCLVKGYFPEPVTV--TW----
NSGALSSD-VHTFPAVLQ---SGLYTLTSSVT---SS-TWP-SQTVT-CNVAHPASSTKV-DKKV
Rat IgG2c   62   ARTTAPSVYPLVPGCSG--TSGSLVTLGCLVKGYFPEPVTV--KW----
NSGALSSG-VHTFPAVLQ---SGLYTLSSSVTVPSS--TWS-SQTVT-CSVAHPATKSNL-IKRI
Mouse IgG1  65   AKTTPPSVYPLAPGSAA--QTNSMVTLGCLVKGYFPEPVTV--TW----
NSGSLSSG-VHTFPAVLQ---SDLYTLSSSVTVPSS--PRP-SETVT-CNVAHPASSTKV-DKKI
Mouse IgG2a 64   AKTTAPSVYPLAPVCGD--TTGSSVTLGCLVKGYFPEPVTL--TW----
NSGSLSSG-VHTFPAVLQ---SDLYTLSSSVTVTSS--TWP-SQSIT-CNVAHPASSTKV-DKKI
Mouse IgG2b 62   AKTTPPSVYPLAPGCGD--TTGSSVTLGCLVKGYFPEPSVTV--TW----
NSGSLSSS-VHTFPALLQ---SGLYTMSSSVTVPSS--TWP-SQTVT-CSVAHPASSTTV-DKKL
Mouse IgG3  60   ATTTAPSVYPLVPGCSD--TSGSSVTLGCLVKGYFPEPVTV--KW----
NYGALSSG-VRTVSSVLQ---SGFYSLSSSLVTVPSS--TWP-SQTVI-CNVAHPASKTEL-IKRI
```

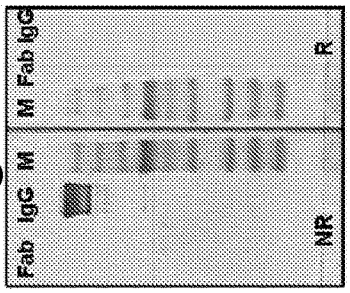
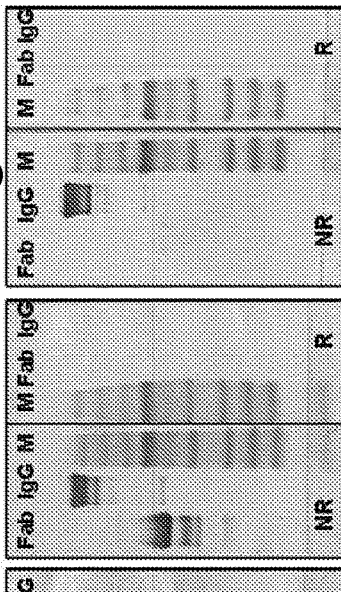
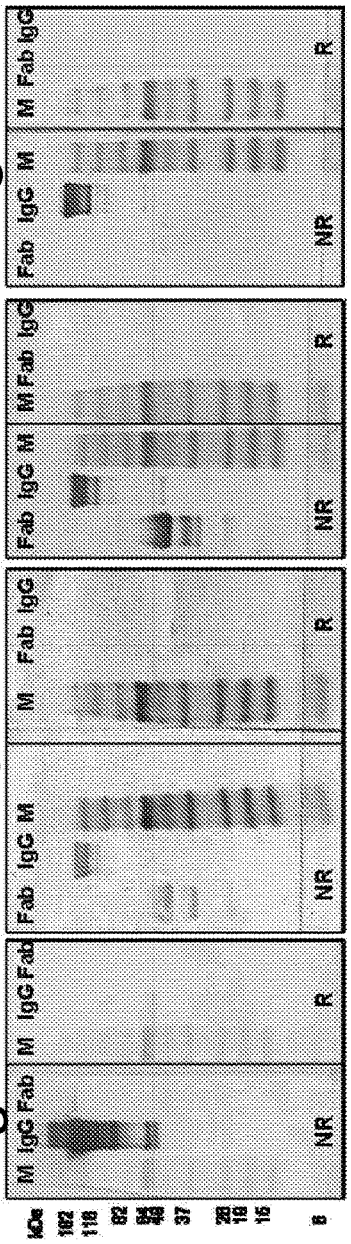
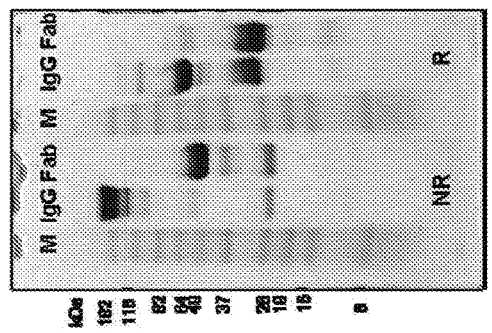

ANTIGEN-BINDING PROTEIN DIRECTED AGAINST EPITOPE IN THE CH1 DOMAIN OF HUMAN IGG ANTIBODIES

SEQUENCE LISTING

The instant application contains a Sequence Listing which has been submitted electronically in ASCII format and is hereby incorporated by reference in its entirety. Said ASCII copy, created on Jul. 24, 2017, is named LT00829US_SL.txt and is 239,631 bytes in size.

FIELD OF THE INVENTION

The present invention relates to the field of biochemistry and immunology, in particular immunoaffinity and antibody technology. The invention relates to methods for capture of target molecules comprising a human IgG-CH1 domain using an antigen-binding protein that is capable of binding a human CH1 domain. The invention further relates to means for use in said methods, including antigen-binding proteins derived from camelid antibodies, immunoadsorbant materials comprising such proteins and means and methods for their production.

BACKGROUND OF THE INVENTION

Efficient, rapid, save and cost efficient purification of mammalian IgG antibodies and/or Fab fragments thereof, in particular human and/or humanized IgG antibodies and/or Fab fragments thereof is a much studied problem in the art. With the advent of new antibody based medicaments, purification of IgG and/or Fab fragments thereof becomes a more critical and costly step in the production of antibody based medicaments, requiring a high degree of purity. In addition, such therapeutic antibodies must retain their binding affinity as well as biological activities including effector functions.

For the purification of all four subclasses of human or humanized IgG, i.e. human/humanized IgG1, IgG2, IgG3 and IgG4, commonly used purification methods comprise the use of classical biochemical separation and purification techniques such as anion/kation exchange, size-exclusion/gelfiltration, precipitations and use of specific affinity ligands. Commonly used affinity ligands are bacterially derived Protein-A and Protein-G, monoclonal antibodies and camelid antibodies or binding fragments derived therefrom that bind one or more of the four subclasses of human or humanized IgG.

Protein A binds to the CH2-CH3 interface of human IgG1, human IgG2 and human IgG4 (Fc) and as such cannot be used for the purification of human IgG3 and thus not for all human IgG subclasses. Protein A shows binding to some human VH domains of the VH3 family but not to human VH1 and VH2 (Jansson et al (1998) FEMS Immunology and Medical Microbiology 20:69-78) and therefore Protein A cannot be used as a generic tool for purification of all human IgG derived Fab fragments. Furthermore, Protein A cannot be used to selectively capture human IgG derived Fab fragments from feed stock samples consisting of a mixture of human IgG Fc- and Fab fragments, due to its more prominent binding reactivity towards IgG Fc domains. In addition, Z-domain based Protein A variants (like Mab Select Sure) lack the ability to bind to human VH3 domains and as such can not be used for Fab purification.

Protein-G is a bacterial surface protein expressed by group C and G streptococci. Protein-G recognizes a common site at the interface between CH2 and CH3 domains on the Fc part of human IgG1, IgG2, IgG3 and IgG4 antibodies (Fcγ) with high affinity. In addition, Protein-G shows binding to the Fab portion of IgG antibodies through binding to the CH1 domain of IgG in combination with a CL-domain of the kappa isotype (Derrick and Wigley (1994) J. Mol. Biol. 243:906-918). Protein-G only binds to Fab from IgG1, IgG3 and IgG4, but not to Fab of IgG2 (Perosa et al (1997) Journal of Immunological Methods 203:153-155). Binding affinity towards CH1 is significantly lower compared to its epitope on the Fc part, which for instance reflects in the low flow rates which must be used to enable efficient purification of human Fab fragments (Proudfoot et al. (1992) Protein expression and purification 3:368-373). Regarding binding of Protein-G at the interface between CH2 and CH3 domains, experimental data indicate that induced fit occurs, which may explain the harsh conditions required for elution as illustrated by an elution pH at or below pH 2.5 (PROTEUS, Protein G Antibody Purification Handbook; Mini&Midi spin columns; 5 Sep. 2005; Pro-Chem, Littleton, USA). These harsh conditions may affect the conformation of the binding sites, thereby altering the immune function of purified IgG antibodies (P. Gagnon, 1996, in Purification tools for monoclonal antibodies, published by Validated Biosystems, Inc 5800N). X-ray crystallographic measurements have shown that through binding to Protein-A, the CH2 domains can be displaced longitudinally towards the CH3 domains, which finally causes partial rotation and destabilization of the carbohydrate region between the CH2 domains. The distortion interferes with subsequent protein-protein interactions that are required for the IgG to exert its effector functions. Aside from the consequences of harsh elution conditions (especially for Protein-G) on the antigen binding capabilities, these secondary effects sometimes interfere with or alter antibody effector functions and increased susceptibility of immunoglobulins to proteolysis. Loss of effector functions, caused by denaturation, altered folding and chemical modifications that arise during purification steps, are highly undesirable if the human or humanized antibodies are to be used for therapeutic purposes. In particular, reduction of intra- and inter-molecular sulphur bridges is often a problem that arises during purification and storage.

Protein L binds human Fab via VL kappa 1, 3, and 4 but does not bind to VL kappa 2 and none of the VL domains of the lambda isotype. Thus, Protein L does not bind to all human IgG derived Fab fragments and is not selective for IgG only.

As alternative to human IgG binding proteins like Protein-G, several mouse monoclonal antibodies (Mabs) have been described in literature that are capable of binding to the Fc domain of human IgG antibodies (Nelson P N, et al. Characterisation of anti-IgG monoclonal antibody A57H by epitope mapping. Biochem Soc Trans 1997; 25:373.). Some common Fc epitopes have been identified and a number of examples are: Mabs G7C, JD312 have a binding epitope on CH2, amino acids 290-KPREE-294. Mabs PNF69C, PNF110A, PNF211C, have a binding epitope on CH2-CH3, AA: 338-KAKGQPR-344. Mab A57H shows binding epitope on CH3, AA 380-EWESNGQPE-388. A problem associated with the use of mouse Mabs, or Mabs from other non-human species, is the release of Mabs from the matrix which causes contamination in the purified preparations that is difficult to remove. Furthermore, Mabs and functional fragments thereof (Fab, Fab2) are easily denatured and S—S bridges, necessary for the correct the 3D structure of the molecule and the alignment of the heavy and light chains, are easily disrupted, in particular under harsh elution conditions that are oftentimes required for release of column bound human IgG's. Due to the vulnerability of the Mab-based affinity ligands the capacity of the column is rapidly reduced, and columns have a very limited re-use capacity after elution and are unsuitable for continuous operation.

Instead of (sc)Fv fragments as described in EP-A-434317, antibody fragments derived from antibodies naturally devoid of light chains (VHH) as described in WO2006/059904 can also be used to generate immunosorbent materials for the purification of human IgG antibodies. Advantage of use of these VHH fragments are that they are single domain peptides, which are exceptionally stable even at higher temperatures. Furthermore, VHH's, are small and easily produced in cost-efficient host organisms such as *Saccharomyces cerevisiae*. In addition, due to the sequence similarity between these VHH fragments and the human VH3 domain family, immunogenecity is expected to be very low compared to bacterial surface proteins like Protein-A and G. These antibodies are described in more detail in EP-A-656946.

The amino acid sequences as described in WO2006/059904 relate to VHH fragments that bind to the light chain of human antibodies of either the kappa or lambda isotype, and as such do not enable selective purification of antibodies and/or Fab fragments of the IgG isotype only. In addition, the excess of light chains present in the supernatant of e.g. cell lines expressing human IgG antibodies and/or Fab fragments thereof, will also be captured by said ligands. Synthetic ligands such as Fabsorbent™ F1P HF (ProMetic BioSciences Ltd, Cambridge, UK) have the same drawbacks.

The amino acid sequences as described in WO2009/011572 relate to VHH fragments that bind to the Fc part of human IgG. As such they do not allow purification of fragments of human IgG that do not comprise the Fc domain, such as Fab of F(ab')$_2$ fragments of human IgG.

Carredano et al. describe the development of synthetic affinity ligands for human Fab purification, binding to a conserved cavity common to all antibodies of the IgG-kappa type (a small pocket formed between the IgG CH1 and the CL-kappa domain) (Carredano et al. (2004) Protein Science 13:1476-1488). Although the IgG-CH1 is considered to be the most conserved region among different IgG Fab fragments, Carredano et al. concluded this domain to be less suitable for generating good binding affinity ligands, because of its flat structure (as also reported in Derrick et al. supra). Rather, the above cavity was selected, hence accepting a lack of reactivity towards human Fab fragments comprising a light chain of the lambda isotype.

Thus, binding agents known in the art have been described that can be used for the purification of human IgG antibodies and/or Fab fragments thereof. However, none of these binding agents (on its own) can provide a generic purification process for all human IgG antibodies and/or Fab fragments thereof. Thus, there is a need in the art for new means and methods that allow a generic approach for the capture and/or purification of human or humanized IgG1, IgG2, IgG3 and IgG4 and/or Fab fragments thereof.

SUMMARY OF THE INVENTION

In a first aspect, the present invention relates to a method for capturing a target molecule comprising a human IgG-CH1 domain, wherein the method comprises the steps of: a) bringing a sample comprising the target molecule in contact with an immunoadsorbent material comprising an antigen-binding protein immobilised on a support; and, b) allowing capture of the target molecule with the immunoadsorbent material by specific binding to the antigen-binding protein; wherein the antigen-binding protein is capable of binding to a single epitope, which epitope is comprised in the CH1 domain of each of human IgG1, human IgG2, human IgG3 and human IgG4, wherein the antigen-binding protein is cross-blocked by a VHH having the amino acid sequence of SEQ ID NO: 1 or wherein the antigen-binding protein is cross-blocked by a VHH having any one of the amino acid sequences of SEQ ID NO: 1-158, and preferably wherein the antigen-binding protein comprises an immunoglobulin-derived variable domain that comprises a complete antigen-binding site for the epitope.

In a preferred embodiment, the antigen-binding protein comprises: a) an antibody obtainable from camelids or sharks, which antibody consists of only heavy chains and is naturally devoid of light chains; b) a variable domain of an antibody defined in a); or, c) a variable domain wherein the frame work sequences of a variable domain defined in b) are grafted with CDRs obtained from other sources.

In a preferred embodiment, the target molecule is a molecule selected from the group consisting of a human or humanized IgG1 molecule, a human or humanized IgG2 molecule, a human or humanized IgG3 molecule, a human or humanized IgG4 molecule, a human or humanized IgG Fab, a human or humanized IgG F(ab')$_2$, a one armed human or humanized IgG antibody, a single chain human or humanized IgG antibody, IVIG, and human or humanized IgG digests. In a preferred embodiment, the human or humanized IgG digest is a papain or pepsin human IgG digest.

Alternatively or in combination with an earlier preferred embodiment, in a preferred embodiment, the antigen-binding protein binds to an epitope of the CH1 domain which epitope involves one or more of the amino acids: a phenylalanine at position 122, none or a single cysteine at either one of positions 127 and 128, a serine or a lysine at position 156 and/or an asparagine or a serine at position 216, whereby the positions of the amino acids are based on Kabat numbering.

Alternatively or in combination with an earlier preferred embodiment, in a preferred embodiment, the antigen-binding protein is: a) an antibody; b) an antibody fragment comprising a full antigen binding site; c) a single domain heavy chain antibody devoid of light chains; d) a fragment of a single domain heavy chain antibody devoid of light chains comprising a full antigen binding site; or, e) an immunoglobulin-derived variable domain comprising a complete antigen-binding site. Preferably, the antigen-binding protein is a camelid VHH or camelidised VH.

In a preferred embodiment, the invention relates to a method for purifying a target molecule, the method comprising capturing the target molecule with the immunoadsorbent material in a method as defined in previous embodiments, wherein the method further comprises the step of: c) eluting the bound target molecules under conditions that decrease the affinity between the target molecules and the immunoadsorbent material, and optionally recovery of the target molecule. In a preferred embodiment, the antigen-binding protein does not bind to free light chains, more preferably not to free light chains of human antibodies, more preferably not to light chains of human IgG.

In an aspect, the present invention relates to a method for purifying a Fab fragment comprising a human IgG-CH1 domain without copurification of free light chains, wherein the method comprises the steps of: a) bringing a sample comprising the target molecule and free light chains in contact with an immunoadsorbent material comprising an antigen-binding protein immobilised on a support; b) allowing capture of the target molecule with the immunoadsorbent material by specific binding to the antigen-binding protein; and c) eluting the bound target molecules under conditions that decrease the affinity between the target molecules and the immunoadsorbent material, and optionally recovery of the target molecule; wherein the antigen-binding protein is as defined in any of the preceding embodiments.

In an aspect, the present invention relates to an in vitro method for adsorbing a target molecule comprising a human IgG-CH1 domain from a fluid, the method comprising the step of bringing an immunoadsorbent material into contact with the fluid, wherein the immunoadsorbent material comprises an antigen-binding protein as defined in any of the preceding embodiments immobilised onto a carrier, and wherein preferably the antigen-binding protein is immobilised onto the carrier by a covalent link.

In an aspect, the present invention relates to an antigen-binding protein as defined in any one of the preceding embodiments.

In an aspect, the present invention further relates to a nucleic acid comprising a nucleotide sequence encoding an antigen-binding protein according to the invention.

In an aspect, the present invention further relates to a host cell comprising a nucleic acid according to the invention.

In a further aspect, the invention relates to a method for producing an antigen-binding protein according of the invention, the method comprising the step of culturing a host cell according to the invention under conditions conducive to expression of the antigen-binding protein.

In a further aspect, the invention relates to an immunoadsorbent material comprising an antigen-binding protein according to the invention.

In a further aspect, the invention relates to a use of an antigen-binding protein according to the invention or of an immunoadsorbent material according to the invention for the detection and/or purification of a target molecule comprising a human IgG-CH1 domain, preferably for the in vitro detection and/or in vitro purification of a target molecule comprising a human IgG-CH1 domain. In a preferred embodiment, the target molecule is a molecule selected from the group consisting of a human or humanized IgG1, a human or humanized IgG2, a human or humanized IgG3, a human or humanized IgG4, a human or humanized IgG Fab, a human or humanized IgG F(ab')2, a one armed human or humanized IgG antibody, a single chain human or humanized IgG antibody, IVIG, and human or humanized IgG digests. In a preferred embodiment, the human IgG digest is a papain or pepsin human or humanized IgG digest. In a preferred embodiment, the target molecule is a human IgG or a human or humanized IgG Fab without co-binding of free light chains. In a preferred embodiment the target molecule is a human IgG Fab in the presence of free light chains.

DESCRIPTION OF THE INVENTION

Definitions

"Sequence identity" or "identity" is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 is ClustalW (1.83) using a blosum matrix and default settings (Gap opening penalty: 10; Gap extension penalty: 0.05). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

The word "isotype" in the context of an antibody or an immunoglobulin (Ig) is herein used to define the antibody isotypes known as IgA, IgD, IgE, IgG and IgM. "human IgG subclasses" are herein used to indicate IgG1, IgG2, IgG3 and IgG4.

"Intravenous immunoglobulin", "Intra Venous Immunoglobulin" or "IVIG" is a blood product administered intravenously. It contains the pooled IgG extracted from the plasma of over a thousand blood donors. IVIG is used in the treatment of immune deficiencies such as X-linked a gammaglobulinemia, hypogammaglobulinemia, acquired compromised immunity conditions featuring low antibody levels, inflammatory and autoimmune diseases and acute infections. IVIG is given as a plasma protein replacement therapy (IgG) for immune deficient patients who have decreased or abolished antibody production capabilities. IVIG is also used in a variety of other conditions, such as allogeneic bone marrow transplant, chronic lymphocytic leukemia, idiopathic thrombocytopenic purpura, peiatric HIV, primary immunodeficiencies, Kawasaki disease, chronic inflammatory demyelinating polyneuropathy, kidney transplant with a high antibody recipient or with an ABO incompatible donor, autism, chronic fatigue syndrome, *Clostridium difficile* colitis, dermatomyositis and polymyositis, graves ophthalmopathy, guillain-Barré syndrome, muscular dystrophy and inclusion body myuositis.

An epitope (also known as "antigenic determinant") is defined as the portion of the target molecule that is bound by the antigen-binding protein. The part of an antigen-binding protein that recognizes the epitope is called a paratope. The epitopes of protein target molecules are divided into two categories, conformational epitopes and linear epitopes, based on their structure and interaction with the paratope. A conformational epitope is composed of discontinuous sections of the target molecule's amino acid sequence. These epitopes interact with the paratope based on the 3-D surface features and shape or tertiary structure of the target molecule. In contrast, linear epitopes interact with the paratope based on their primary structure, the amino acids that make up a linear epitope are a continuous sequence of amino acids from the target molecule. In case the antigen-binding protein is an antibody, the epitope is the portion of a target molecule that triggers an immunological response upon immunisation of an individual vertebrate host with this molecule. Generally it is the site of the target molecule where binding to an antibody takes place. The epitope is preferably present naturally in the target molecule. Optionally the epitope(s) is/are a sequence that has been artificially included in the target molecule. Optionally a multitude of the same or different epitopes is included in the target molecule to facilitate its purification and detection.

The term "specific binding" or "binding" as used herein, in reference to the interaction of an antigen-binding protein and a target molecule, means that the antigen-binding protein recognizes a target molecule and that the interaction is dependent upon the presence of a particular structure (i.e., the antigenic determinant or epitope) on the target molecule; in other words, the antigen-binding protein is recognizing and binding to a specific target molecule structure rather than to proteins in general. An antigen-binding protein of the invention, that can bind to, that can specifically bind to, that has affinity for and/or that has specificity for a specific target molecule (antigenic determinant, epitope, antigen or protein) may be said to be "against" or "directed against" said target molecule. The term "specificity" refers to the number of different types of antigens or antigenic determinants to which a particular antigen-binding protein molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein. Alternatively, the affinity can also be expressed as the affinity constant ($K_A$), which is $1/K_D$. Affinity can be determined in a manner known per se, depending on the specific combination of antigen-binding protein and antigen of interest. Avidity is herein understood to refer to the strength of binding of a target molecule with multiple binding sites by a larger complex of binding agents, i.e. the strength of binding of multivalent binding. Avidity is related to both the affinity between an antigenic determinant and its antigen binding site on the antigen-binding molecule and the number of binding sites present on the antigen-binding molecule. Affinity, on the other hand refers to simple monovalent receptor ligand systems.

The terms peptide and polypeptide are used synonymously herein to refer to this class of compounds without restriction as to size. The largest members of this class are referred to as proteins.

DETAILED DESCRIPTION OF THE INVENTION

The inventors have found a new method for the selective capture and/or purification of target molecules comprising a human IgG-CH1 domain, including human or humanized IgG1, IgG2, IgG3, IgG4 antibodies and/or fragments thereof, wherein the method involves a particular class of antigen-binding proteins that are useful for incorporation into and/or attachment to immunoadsorbent materials. The antigen-binding proteins that are used in this method preferably act through binding of an epitope that is present in the CH1 domain of each of human IgG1, human IgG2, human IgG3 and human IgG4 and thus independent of the IgG-Fc domain. An antigen-binding protein that is used in a method of the invention preferably binds to a unique epitope solely present on the CH1 domain of an antibody heavy chain of the IgG isotype. Furthermore, the antigen-binding proteins that are used in a method of the invention preferably do not bind to human heavy chain antibody isotypes other than IgG nor to IgG antibodies from e.g. bovine and swine. More preferably, the antigen-binding proteins show effective elution, i.e. release of the target molecule, under mild conditions (e.g., pH≥3). The antigen-binding proteins used in a method according to the invention have the affinity and selectivity required for specific binding of human IgG antibodies and/or Fab (Fragment antigen binding) fragments or other fragments that comprise a human IgG CH1 domain of one of the four human IgG subclasses, independent of the type of light chain and VH subclass. Through selective binding of the CH1 domains of human IgG1, human IgG2, human IgG3 and human IgG4, the antigen-binding protein of the invention can be used for capture and/or to purify any human IgG derived Fab fragment independent of its IgG subclass, light chain isotype and VH subclass. This selectivity further results in a clear benefit of lack of cross-binding to free antibody light chains and/or IgG Fc fragments that can be present in feed stock materials originating from e.g. recombinant expression systems and/or pepsin or papain treated IgG digestion products. This selectivity is unique and has not been demonstrated with any of the antigen-binding proteins known in the art. Interestingly, up to this date the inventors are not aware that anyone has ever reported an antigen-binding protein specific for an epitope present on the CH1 domains of human IgG antibodies of all isotypes.

The current invention provides a generic tool for the isotype specific capture and/or purification of human IgG antibodies and/or Fab fragments thereof, independent of the IgG subclass, the type of light chain and VH subclass of said human IgG antibody or Fab fragment, thereby e.g. eliminating the need of different types of binding agents and/or processes to enable purification of the entire set of human IgG antibody targets.

Thus, the antigen-binding proteins of the current invention enable the selective capture and/or purification of all human IgG derived Fab fragments, without showing any cross-reactivity towards free antibody light chains and/or IgG Fc fragments that can be present in the feed stock materials. None of the binding agents known in the art can selectively purify human IgG Fabs without showing cross-reactivity to either free light chains (e.g. Protein L, KappaSelect, FabSorbent) or to the IgG Fc domain (e.g. Protein A and G) nor can each of these binding agents when taken on their own, cover the purification of all types of Fab fragments derived from all 4 human IgG subclasses. Furthermore, due to the binding of Protein A and G to IgG Fc domains, Protein A and G cannot be used to selectively capture human IgG derived Fab fragments from feed stock samples consisting of a mixture of human IgG Fc- and Fab fragments.

Since the binding agents of the current invention show comparable binding characteristics towards the CH1 domain of all 4 different human IgG subclass antibodies, it enables selective purification of polyclonal IgG from e.g. human plasma derived feed stock samples under mild elution conditions without altering the IgG subclass distribution of the starting material independent of the percentage of breakthrough in situations wherein the immunosorbent material is overloaded.

In a first aspect, the invention relates to a method for capturing a target molecule comprising an amino acid sequence as presented by a human IgG-CH1 domain. The method preferably comprises the steps of: a) bringing a composition comprising the target molecule in contact with the immunoadsorbent material comprising an antigen-binding protein of the invention, preferably immobilised on a support; and b) allowing capture of the target molecule with the immunoadsorbent material by specific binding to the antigen-binding protein, preferably under conditions that allow binding of the target molecules to the antigen-binding protein in the immunoadsorbent material. We will now first describe an antigen-binding protein according to the invention.

Antigen-Binding Protein

In a second aspect, the present invention relates to an antigen-binding protein that specifically binds to a single epitope, which epitope is comprised in the CH1 domain of each of human IgG1, human IgG2, human IgG3 and human IgG4. Preferably, an antigen-binding protein of the invention is capable of specifically binding to an epitope present in the CH1 domain of the human IgGs that is also specifically bound by one or more VHHs having an amino acid sequence selected from SEQ ID NO: 1-158 (the reference VHHs). Binding of an antigen-binding protein of the invention to an epitope in the CH1 domain of the human IgGs that is also specifically bound by at least one of the reference VHHs is preferably determined by the ability of the antigen-binding protein to cross-block the binding of one or more of the reference VHHs (i.e. any one or more of SEQ ID NO: 1-158) to the epitope.

Thus, a preferred antigen-binding protein of the invention has the ability to cross-block the binding of one or more VHHs having an amino acid sequence selected from SEQ ID NO: 1-158 to a target molecule comprising a human CH1 domain, such as for example SEQ ID NO: 28. The ability of an antigen-binding protein to cross-block the binding of a reference VHH is herein defined as the ability to reduce the binding of the reference VHH to a suitable target molecule comprising a CH1 domain of a human IgG by at least 10, 20, 50, 75, 90, 95, 99, 99.9 or 99.99% when the target molecule has first been bound by the antigen-binding protein, or vice versa (i.e. binding of the antigen-binding protein is reduced when the target molecule is first bound by the reference VHH).

The ability to cross-block may in principle be determined using any type of immunoassay, preferably a competitive immunoassay, including e.g. ELISA, solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1125 label (see Morel et al., Molec. Immunol. 25(1): 7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)).

Typically, such an assay involves the use of a purified target molecule bound to a solid surface, an unlabelled test antigen-binding protein and a labelled reference VHH. Competitive inhibition is measured by determining the amount of label bound to the solid surface in the presence of the test antigen-binding protein. Usually the test antigen-binding protein is present in excess. An example of a suitable competitive binding assay is e.g. presented below. Antigen-binding protein identified by competition assay (competing antigen-binding protein) include antigen-binding protein binding to the same epitope as the reference VHH and antigen-binding protein binding to an adjacent epitope sufficiently proximal to the epitope bound by the reference antigen-binding protein for steric hindrance to occur. A suitable target molecule is any target molecule comprising a human CH1 domain, as defined herein below including e.g. human IgGs and Fab fragments thereof.

E.g. one can use a reference anti-IgG-CH1 VHH fragment and the antigen-binding protein to be determined in e.g. a sandwich ELISA set-up to determine whether both binding proteins are able to simultaneously bind to a CH1 domain of a human IgG Fab fragment. For this purpose the reference anti-IgG-CH1 VHH fragment is preferably coated on a Maxisorp ELISA plate and blocked with 2% (w/v) milk powder (Protifar) in PBS. As a control an anti human Fab kappa light chain VHH fragment (anti Fab-kappa) is preferably coated next to a no-coat control. Polyclonal human IgG Fab fragments are then allowed to bind to the immobilized VHH fragments for 1 hr (10 µg/ml Fab in 1% (w/v) milk powder and 0.05% (v/v) Tween-20 in PBS, 100 µl/well). After washing, the bound human Fab fragments are detected either using biotinylated antigen-binding protein of which the cross-blocking is to be determined or Protein L (the latter binding to the VL-kappa domain of human Fabs) followed by an incubation with HRPO conjugated streptavidin for detection.

A target molecule is herein defined as a molecule that is to be bound by a binding agent, preferably an antigen-binding protein of the invention. A target molecule may be a protein that requires capture, purification, or that needs to be removed from a sample or a protein that is to be detected or identified.

In a preferred embodiment, an antigen-binding protein of the invention is able to selectively bind to a target molecule comprising a human IgG-CH1 domain or an allelic variant thereof. Preferably, the target molecule comprising a human IgG-CH1 domain is a molecule selected from the group consisting of a human IgG1 molecule, a human IgG2 molecule, a human IgG3 molecule, a human IgG4 molecule, a human Fab, a human F(ab')$_2$, a one armed human antibody, a single chain human antibody a humanized IgG1 molecule, a humanized IgG2 molecule, a humanized IgG3 molecule, a humanized IgG4 molecule, a humanized Fab, a humanized F(ab')$_2$, a one armed humanized antibody, a single chain humanized antibody and IVIG. A humanized antibody or antibody fragment is herein understood as a chimeric antibody or antibody fragment wherein at least part of one or more of the constant domains are of human origin and wherein at least part of one or more of the CDRs are not of human origin.

An advantage of an antigen-binding protein of the present invention for the purification of IVIG is that the subclass distribution is maintained. An advantage of an antigen binding protein according to the present invention in the purification of Fab fragments, is that the antigen binding protein of the invention does not cross-bind to free light chains and Fc fragments. In another embodiment, the target molecule comprising a human IgG-CH1 domain is a recombinant protein. The recombinant protein can be a fusion protein or a chimeric protein such as a humanized antibody.

Alternatively or in combination with a previous embodiment, an antigen-binding protein of the invention is able to selectively bind to a target molecule comprising a human IgG CH1 domain of human IgG1, IgG2, IgG3 or IgG4 defined by the amino acid sequence of any one of SEQ ID NO: 190-193. In a preferred embodiment, an antigen-binding protein of the invention is able to selectively bind to an epitope of an IgG CH1 domain which epitope is defined by any one of the amino acid sequences of SEQ ID NO: 194-200. In a preferred embodiment, an antigen-binding protein of the invention is not able to selectively bind to an epitope of a IgG CH1 domain which epitope is defined by the any one of the amino acid sequences of SEQ ID NO: 201-217.

An antigen-binding protein according to the invention preferably does not bind to human non-IgG related antibody isotypes, an Fc domain of a human IgG, an Fv domain of a human IgG, or free light chains of human IgG. In particular, Protein G and protein A are not antigen-binding proteins according to the invention.

In a preferred embodiment, an antigen-binding protein according to the invention binds to an epitope present in the CH1 domain of a human IgG1, IgG2, IgG3 and IgG4 antibody heavy chain of the IgG isotype wherein the binding to the epitope in the CH1 domain is of comparable nM affinity for each of the four human IgG subclasses, i.e. the affinities for each of the four subclasses preferably do not differ by more than one order of magnitude, more preferably the difference is less than a factor 5, 4, 3 or 2.

In an embodiment, an antigen-binding protein of the invention does not bind to at least one CH1 domain of an IgG selected from the group consisting of rabbit IgG, swine IgG1, swine IgG2, bovine IgG1, bovine IgG2, sheep IgG1, goat IgG1, lama IgG1a, lama IgG1b, rat IgG1, rat IgG2a, rat IgG2b, rat IgG2c, mouse IgG1, mouse IgG2a, mouse IgG2b and mouse IgG3.

Human IgG1, human IgG2, human IgG3 and/or human IgG4 as used herein can be native, intact, or complete human IgG1, human IgG2, human IgG3 and/or human IgG4. It can also encompass humanized IgG1, IgG2, IgG3 and/or IgG4.

Preferably, binding of the antigen-binding protein to the target molecule, e.g. human IgG, and subsequent elution of the target molecule does not affect effector functions of the target molecule as may be determined in assays known per se. Also preferred is that binding of the antigen-binding protein to the target molecule, such as human IgG, and subsequent elution of the target molecule does not reduce, inhibit or otherwise affect binding of the target molecule to its predetermined antigen.

In a preferred embodiment, an antigen-binding protein of the invention binds to an epitope of the CH1 domain which epitope comprises, involves and/or is defined by one or more of the amino acids: a phenylalanine at position 122, none or a single cysteine at either one of positions 127 and 128, a serine or a lysine at position 156 and/or an asparagine or a serine at position 216, whereby the positions of the amino acids are based on Kabat numbering (E. A. Kabat, T. T. Wu, H. M. Perry, K. S. Gottesman and C. Foeller, Sequences of Proteins of Immunological Interest (5th Edition), *NIH Publication No.* 91-3242, U.S. Department of Health and Human Services, Public Health Service, National Institutes of Health (1991)). It follows that the epitope of the CH1 domain to which an antigen-binding protein of the present invention binds particularly does not comprise a tyrosine residue at position 122 and does not comprise a threonine residue at position 156. More preferably, the epitope comprises either a serine residue at position 156 and an asparagine residue at position 216 or a lysine residue at position 156 and a serine residue at position 216.

The epitope recognized on the CH1 domain of IgG antibodies by an antigen-binding protein of the current invention is different compared to the one recognized by Protein G. For instance, the latter affinity ligand does not discriminate between CH1 domains having a Phe or a Tyr residue at position 122 as observed for the binding agents of the current invention (which do not binding to CH1 domains having a Tyr at position 122).

To test whether a potential antigen-binding protein is able to specifically bind to a target molecule but not to another molecule such as for example human IgG Fc fragments, Fv fragments and/or light chains, preferably an ELISA and/or surface plasmon resonance analysis as described in the Examples can be performed.

In a preferred embodiment, an antigen-binding protein according to the invention comprises one or more single binding domains, whereby a single binding domain does not comprise a light chain and whereby the single binding domain comprises the full antigen-binding capacity. Preferably, an antigen-binding protein of the invention is selected from the group consisting of an antibody comprising heavy chains and being devoid of light chains, a fragment thereof, an affibody, a single domain antibody and a fragment thereof. Examples of antigen-binding proteins according to the invention are VHH derived from camelid or shark heavy chain only antibodies that are naturally devoid of light chains and affibodies. Preferably an antigen-binding protein is an antibody that comprises heavy chains only and that is naturally devoid of light chains or antibody fragment thereof. Alternatively, (and also preferred) antigen-binding protein of the invention can be derived from an antibody naturally devoid of light chains or a fragment thereof, e.g. by modification such as mutation. Antibodies naturally devoid of light chains may be obtained e.g. by immunisation of camelids (e.g. llama, camels, dromedaries, Bactrian camels, alpacas, vicuñas and guanacos) or sharks (see further below). These antibodies comprise heavy chains only and are devoid of light chains. The advantage of these single domain heavy chain antibodies is that they are exceptionally stable, small and are easily produced in host organisms such as *Saccharomyces cerevisiae*.

Thus, an antigen-binding protein of the invention preferably comprises an immunoglobulin-derived variable domain that comprises a complete antigen-binding site for the epitope on a target molecule in a single polypeptide chain. Such antigen-binding proteins specifically include but are not limited to:

1) antibodies obtainable from camelids and sharks that consist of only heavy chains and that are naturally devoid of light chains;

2) variable domains of the antibodies defined in 1), usually referred to as VHH domains;

3) engineered forms of the antibodies defined in 1) or domains in 2) such as e.g. "camelidised" or "(camelised)" antibodies in which frame work sequences of a camelid (or shark) VHH domain are grafted with CDRs obtained from other sources;

4) engineered forms of immunoglobuline-like variable domains in which frame works sequences from a variety of immunoglobuline-like molecules are combined with CDRs specific for a given target molecule as e.g. described in WO 04/108749.

In a preferred antigen-binding protein of the invention, the single polypeptide chain of the variable domain that comprises the full antigen-binding capacity preferably has an amino acid sequence and structure that can be considered to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. These framework regions and complementary determining regions are preferably are operably linked in the order FR1-CDR1-FR2-CDR2-FR3-CDR3-FR4 (from amino terminus to carboxy terminus).

The total number of amino acid residues in the variable domain with full antigen-binding capacity can be in the region of 110-135, and preferably is in the region of 115-129. However, a variable domain with full antigen-binding capacity in accordance with the invention is not particularly limited as to its length and/or size, as the domain meets the further functional requirements outlined herein and/or is suitable for the purposes described herein. The amino acid residues of a variable domain with full antigen-binding capacity are numbered according to the general numbering for VH domains given by Kabat et al. (E. A. Kabat, T. T. Wu, H. M. Perry, K. S. Gottesman and C. Foeller, Sequences of Proteins of Immunological Interest (5th Edition), *NIH Publication No.* 91-3242, U.S. Department of Health and Human Services, Public Health Service, National Institutes of Health (1991)), as applied to VHH domains from Camelids by Riechmann and Muyldermans (1999, J. Immunol. Methods 231 (1-2): 25-38, see for example FIG. 2 of said reference) and by Harmsen et al. (2000, Molecular Immunology 37: 579-590, see for example FIG. 1 of said reference).

According to this numbering, in a variable domain with full antigen-binding capacity: FR1 comprises the amino acid residues at positions 1-26; CDR1 comprises the amino acid residues at positions 27-35; FR2 comprises the amino acids at positions 36-49; CDR2 comprises the amino acid residues at positions 50-64; FR3 comprises the amino acid residues at positions 65-94; CDR3 comprises the amino acid residues at positions 95-102; and, finally, FR4 comprises the amino acid residues at positions 103-113.

In this respect, it should be noted that—as is well known in the art for VH domains and for VHH domains—the total number of amino acid residues in each of the CDR's may vary and may not correspond to the total number of amino acid residues indicated by the Kabat numbering. However, based on the conserved amino acids of the frame work region a skilled person will be able to align the respective frame work and complementarity determining regions in accordance with the Kabat definitions for those variable domains with full antigen-binding capacity that have a length other than 113 amino acids. Examples thereof are given in the definition of the complementarity determining regions in the amino acid sequences of IgG-CH1 as depicted in FIG. 1. Alternative methods for numbering the amino acid residues of VH domains, which methods can also be applied in an analogous manner to VHH domains from Camelids and to variable domains with full antigen-binding capacity, are the method described by Chothia et al. (Nature 342, 877-883 (1989)), the so-called "AbM definition" and the so-called "contact definition", or the IMGT numbering system (Lefranc et al., 1999, Nucl. Acids Res. 27: 209-212).

Alternatively or in combination with a previous embodiment, in a preferred embodiment the antigen-binding protein comprises an amino acid sequence that comprises 4 framework regions, FR1 to FR4, and 3 complementarity determining regions, CDR1 to CDR3, that are operably linked in the order FR1-CDR1-FR2-CDR2-FR3-CDR3-FR4, wherein: a) the CDR1 has an amino acid sequence selected from the group consisting of SEQ ID No's: 159-162 or an amino acid sequence that differs from SEQ ID No's: 159-162 in one, two, three, four, five or six of the amino acid residues; b) the CDR2 has an amino acid sequence selected from the group consisting of SEQ ID No's: 163-181 or an amino acid sequence that differs from SEQ ID No's: 163-181 in one, two, three, four, five, six, seven, eight, nine or ten of the amino acid residues; and, c) the CDR3 has an amino acid sequence selected from the group consisting of SEQ ID No's: 182-185 or an amino acid sequence that differs from SEQ ID No's: 182-185 in one, two, three, four, five, six, seven, eight, nine or ten of the amino acid residues; and, wherein each of the framework regions has at least 50, 55, 60, 65, 70, 75, 80, 85, 90, 95 or 100% amino acid identity with the framework amino acid sequence of any one of SEQ ID No's: 186-189. Alternatively, at least one of the CDRs in the antigen-binding protein is a CDR selected from the CDRs defined in a), b) and c), above.

In a preferred embodiment, the CDR1 has an amino acid sequence of SEQ ID NO:159 or 160. Alternatively or in combination with previous preferred embodiments, in a preferred embodiment of the invention the CDR2 has an amino acid sequence selected from the group consisting of SEQ ID NO:163-168, SEQ ID NO:176-181. Alternatively or in combination with previous preferred embodiments, in a preferred embodiment of the invention the CDR3 has an amino acid sequence selected from the group consisting of SEQ ID NO:182, SEQ ID NO:183 and SEQ ID NO:184.

In a preferred antigen-binding protein of the invention, the frame work amino acid sequence of a variable domain with full antigen-binding capacity preferably has at least 50, 55, 60, 65, 70, 75, 80, 85, 90, 95 or 100% amino acid identity with the frame work amino acid sequence of any one of SEQ ID No's: 186-189.

More preferably, the amino acid residues that are present at each position (according to the Kabat numbering) of the FR1, FR2, FR3 and FR4 of the single polypeptide chain of the variable domains that specifically bind to human IgG-CH1 according to the invention are as indicated in Tables 1 to 4 for FR1, FR2, FR3 and FR4. For each position, the amino acid residue that most frequently occurs at each position is indicated in bold. Next to these residues, Tables 1 to 4 provide some non-limiting residues that can be present at each position of the FR1, FR2, FR3 and FR4 of naturally occurring VHH domains (data was taken from patent WO 2009/011572; PCT/NL2008/050460). More preferably, however, the frame work amino acid residues of a variable domain with full antigen-binding capacity are chosen from the amino acid residues in Tables 1 to 4 that are present at each position (according to the Kabat numbering) of the FR1, FR2, FR3 and FR4 of the amino acid sequences of any one of SEQ ID No's: 186-189, of antigen-binding proteins that specifically bind a human IgG-CH1. For each position, the amino acid residue that most frequently occurs at each position is indicated in bold in Tables 1 to 4.

Thus, in a preferred embodiment of the invention, on the basis of the amino acid residues present on the positions described in Tables 1 to 4, the amino acid sequence of a variable domain comprising the full antigen-binding capacity in an antigen-binding protein of the invention can have the structure:

FR1-CDR1-FR2-CDR2-FR3-CDR3-FR4 in which FR1 has an amino acid sequence chosen from the group consisting of:

a)

(SEQ ID: 186)
[1] QVQLQESGGGLVQAGGSLRLSCAVSG [26];

b) an amino acid sequence that has at least 50, 55, 60, 65, 70, 75, 80, 85, 90, 95 or 100% sequence identity with the sequence in a); and/or,
c) the amino acid sequence of a) that has one or more amino acid substitutions as defined in Table 1;
in which FR2 is chosen from the group consisting of the amino acid sequence:
d)

(SEQ ID: 187)
1 [36] WFRQTPGNEREFVA [49];

e) an amino acid sequence that has at least 50, 55, 60, 65, 70, 75, 80, 85, 90, 95 or 100% sequence identity with the sequence in d); and/or
f) the amino acid sequence of d) that has one or more amino acid substitutions as defined in Table 2; in which FR3 is chosen from the group consisting of the amino acid sequence:
g)

(SEQ ID: 188)
[65] GRFTISRDSGKNTVYLQMNNLKPEDTAVYYCAG [94];

h) an amino acid sequence that has at least 50, 55, 60, 65, 70, 75, 80, 85, 90, 95 or 100% sequence identity with the sequence in g); and/or,
i) the amino acid sequence of g) that has one or more amino acid substitutions as defined in Table 3; and,
in which FR4 is chosen from the group consisting of the amino acid sequence:
j)

(SEQ ID: 189)
[103] WGQGTQVTVSS [113];

k) an amino acid sequence that has at least 50, 55, 60, 65, 70, 75, 80, 85, 90, 95 or 100% sequence identity with the sequence in j); and/or,
l) the amino acid sequence of j) that has one or more amino acid substitutions as defined in Table 4.

In an alternative preferred embodiment, the antigen-binding protein of the invention comprises a CDR1, CDR2 and CDR3 combination as given in one of the rows of FIG. 1, wherein the framework regions (FR1 to FR4) may be any of the framework regions (FR1 to FR4) as defined above, more preferably a framework region of the same row of FIG. 1. More preferably, the antigen-binding protein of the invention comprises a CDR1, CDR2 and CDR3 combination as given in one of the rows of FIG. 1, wherein the antigen-binding protein has an amino acid sequence with at least 90, 95, 98, 99 or 100% sequence identity to the sequence of the whole amino acid sequence provided in the same row of FIG. 1.

In a preferred embodiment, an antigen-binding protein of the invention comprises an amino acid sequence that has at least 85%, preferably at least 90%, more preferably at least 93, 95, 97, 98, 99 or 100% identity with any of the amino acid sequences of SEQ ID No: 1-158, more preferably wherein the antigen-binding protein consists of an amino acid sequence that has at least 90%, more preferably at least 93, 95, 97, 98, 99 or 100% identity with any of the amino acid sequences of SEQ ID NO:1-158.

The antigen-binding protein of the invention is a component that specifically binds to the target molecule with the desired binding affinity (as herein defined). The antigen-binding protein of the invention preferably is a mono-specific antigen-binding protein. A composition comprising a mono-specific antigen-binding protein, such as the immunoadsorbant materials of the present invention, is understood to mean a composition having a homogeneous population of the antigen-binding protein. It follows that the mono-specific antigen-binding protein is specific for a single epitope. It is however expressly included in the invention that the immunoadsorbant material may comprise more than one type of mono-specific antigen-binding protein, each consisting of a homogeneous population. Usually, however, in the context of the present invention, an immunoadsorbant material will not comprise more than 4, 6, 8, 10 or 20 different mono-specific antigen-binding proteins. The antigen-binding protein will usually be an antibody or fragment thereof, in which case the mono-specific antigen-binding protein will thus be a monoclonal antibody or a fragment thereof, which may be obtained from a cloned cell-line (e.g. hybridoma) or expressed from a cloned coding sequence. The term mono-specific antigen-binding protein as used herein thus excludes polyclonal antibodies and antisera.

Typically, antigen-binding proteins of the invention will bind the target molecule with a dissociation constant ($K_D$) of about $10^{-5}$ to $10^{-12}$ M or less, and preferably $10^{-7}$ to $10^{-12}$ M or less and more preferably $10^{-8}$ to $10^{-12}$ M or less, and/or with a binding affinity of at least $10^{-7}$ M, preferably at least $10^{-8}$ M, more preferably at least $10^{-9}$ M, such as at least $10^{-19}$, $10^{-11}$, $10^{-12}$ M or more. Any $K_D$ value greater than $10^{-4}$ M (i.e. less than 100 µM) is generally considered to indicate non-specific binding. Preferably, a polypeptide of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (MA), enzyme immunoassays (EIA) and sandwich competition assays, and the different variants thereof known per se in the art (see also above). In a preferred embodiment the antigen-binding protein of the invention will bind to the desired antigen with an affinity as defined above yet this affinity is combined an efficient release of the antigen from the antigen-binding protein under mild elution conditions.

Mild elution conditions are herein understood to be conditions under which the activity and/or integrity (e.g. secondary/tertiary structure) are only slightly affected (e.g. less than 10% inactive or denatured), preferably there is no detectable reduction in activity and/or integrity of the antigen. Examples of such mild elution conditions include e.g. the acidic conditions as specified herein below, including e.g. 0.1 M glycine or 0.02 M citric acid pH 3.0 or pH 4.0, 0.1 M arginine pH 4.0 or pH 5.0. Other examples of mild elution conditions at (near)-neutral pH include e.g. high ionic strength such as condition equivalent 2 M NaCl or 2M MgCl2 (in e.g. 20 mM Tris pH 8.0) or chaotropic agents such as ethylene glycol or propylene glycol (40-60%, preferably about 50% (v/v), in e.g. 20 mM Imidazol, 10 mM $CaCl_2$, 0.01% Tween 80, 250 mM NaCl at pH7.0). Examples of antigen-binding proteins of the invention that release the antigen under at pH 3.0 include antigen-binding proteins that have a structure as herein defined above wherein: a) the CDR1 has an amino acid sequence selected from the group consisting of SEQ ID No's: 159-162, or an amino acid sequence that differs from SEQ ID No's: 159-162 in one, two, three, four, five or six amino acid residues; b) the CDR2 has an amino acid sequence selected from the group consisting of SEQ ID No's: 163-181, or an amino acid sequence that differs from SEQ ID No's: 163-181 in one, two, three, four, five, six, seven, eight, nine or ten amino acid residues; and, c) the CDR3 has an amino acid sequence selected from the group consisting of SEQ ID No's: 182-189, or an amino acid sequence that differs from SEQ ID No's: 182-189 in one, two, three, four, five, six, seven, eight, nine or ten amino acid residues. More preferably the antigen-binding protein has an amino acid sequence selected from the group consisting of SEQ ID No's 1-158.

An antigen-binding protein of the invention that binds to an CH1 domain of a human IgG1, human IgG2, human IgG3 and human IgG4 molecule is an antigen-binding protein that preferably has one or more properties selected from the group consisting of: a) the antigen-binding protein binds the human IgG molecule with a binding affinity of at least $10^{-7}$ M, $10^{-8}$ M, or $10^{-9}$ M as analyzed by BiaCore as described in the Examples; b) the antigen-binding protein is obtainable by expression in yeast at an expression level of at least 0.5, 0.8, 1.0 g/L of yeast culture.

In one embodiment the invention pertains to particular form of an antigen-binding protein of the invention: a multivalent antigen-binding protein. The multivalent antigen-binding protein comprises the amino acid sequences of at least two antigen-binding proteins as defined herein above. The amino acid sequences of at least two antigen-binding proteins may be different from each other or they may be identical, e.g. copies or repeats of one amino acid sequence. The amino acid sequences of the at least two antigen-binding proteins will usually be fused head-to tail, i.e. the C-terminus of the most N-terminal sequence fused to the N-terminus of the second sequence and so on. The amino acid sequences of at least two antigen-binding proteins may be fused directly linked or via a linker or spacer. Multivalent antigen-binding proteins of the invention may be produced by expression of a nucleotide sequence encoding the multivalent protein wherein two or more coding sequences of the antigen-binding proteins are operably linked together in the same reading frame. The skilled person will know how to operably fuse protein coding sequences. An advantage of a multivalent antigen-binding protein is that the dynamic binding capacity is improved, particularly if the multivalent antigen-binding domains are directionally immobilized on a solid support, for example using covalent binding.

Antigen-binding proteins of the invention also include modified forms wherein amino acid residues are substituted with lysine residues in order to increase the isoelectric point (pI). Examples of such antigen-binding proteins that are modified forms of SEQ ID No:1 are presented by SEQ ID No's: 10, 19, 28, 37, 46, 55, 64 and 73. Antigen-binding proteins with a pI of above 7 are easier to purify than antigen-binding proteins with a pI under 7, wherein purification is for example from a source such as a yeast fermentation broth via ionic exchange chromatography.

Other advantageous modified forms of an antigen-binding protein are for example forms wherein the antigen-binding proteins have improved stability, e.g. improved caustic stability, improved stability towards denaturing agents and/or improved protease stability. Examples of such antigen-binding proteins that are modified forms of SEQ ID No:28 are presented by SEQ ID No: 29-36, 117-137. The skilled person is aware that some amino acid residues are disadvantageous for the stability of a polypeptide or protein. For example, in the deamidation reaction, the side chain amide linkage in a glutamine or asparagine residue is hydrolyzed to form a free carboxylic acid. As described by Bischoff et al (J. of Chrom B (1994), 622, 261-278) non-enzymatic deamidation of asparagine (Asn, N) and glutamine (Gln, Q) residues in peptides and proteins can occur and that hydrolysis of the amide bond is significantly accelerated under alkaline conditions, especially when e.g. asparagine is followed by a glycine (Gly, G) or a serine (Ser, S) residue. In this respect, asparagine deamidates more easily than glutamine in corresponding positions. In Bischoff et al. combinations of residues are provided that display less labile aspargine residues within a peptide or protein sequence and as such could be incorporated into a VHH sequence e.g. based on commonly occurring—or alternative combinations of residues in order to increase alkaline stability. Furthermore, Geiger et al (J. of Biol Chem (1987) vol. 262, no. 2, 785-794) describe that next to asparagine residues, aspartic acid residues (Asp, D) may be hotspots for non-enzymatic degradation of proteins as well. In this respect, Terashima et al (Anal. Biochem. (2007), 368, 49-60) describes that isomerization of aspartic acid (Asp, D) is accelerated when glycine (Gly, G) is at the C-terminal of the aspartic acid residue and as such other combinations of residues can be envisaged as mentioned above in order to increase stability of an anti-IgG-CH1 antigen-binding protein.

TABLE #1

| Non-limiting examples of amino acid residues in FR1 | | | | | | | | | | | | | | | | | | | | | | | | | | |
|---|---|---|---|---|---|---|---|---|---|---|---|---|---|---|---|---|---|---|---|---|---|---|---|---|---|---|
| | Position | | | | | | | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| a.a. residue anti-IgG CH1 a.a. sequences | Q | V | Q | L | Q | E | S | G | G | G | L | V | Q | A | G | G | S | L | R | L | S | C | A | V | S | G |
| | | | | D | | | | | | | S | | | | E | A | | T | | | | | E V | | | |
| a.a. residue | A | K | E Q F | | D | M | A | E | Q | | D | F | V | L | F | F | | | D | A | A | Q | | | | |

TABLE #1-continued

Non-limiting examples of amino acid residues in FR1

| | Position | | | | | | | | | | | | | | | | | | | | | | | | | |
|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| Camelid VHH's | E | | | L<br>V | A | | | | | | R | V<br>W | | K<br>P<br>R | A<br>G<br>S<br>V<br>P<br>T | | E | | N<br>S<br>K | I<br>V | T<br>A | | P<br>T<br>R<br>S | I<br>L<br>S<br>T<br>P<br>D | F<br>P<br>T<br>L | P<br>A<br>D<br>E<br>R<br>S<br>T<br>V |

TABLE #2

Non-limiting examples of amino acid residues in FR2

| | Position | | | | | | | | | | | | | |
|---|---|---|---|---|---|---|---|---|---|---|---|---|---|---|
| | 36 | 37 | 38 | 39 | 40 | 41 | 42 | 43 | 44 | 45 | 46 | 47 | 48 | 49 |
| a.a. residue anti-IgG CH1 a.a. sequences | W | F | R | Q | T<br>A<br>V | P | G<br>L | N<br>R<br>H | E<br>K<br>K | R | E | F | V | A |
| a.a. residue Camelid VHH's | | L<br>Y<br>H<br>I<br>V | | H<br>P<br>R<br>E | F<br>L<br>T<br>P<br>G | A<br>S | E | D<br>E<br>Q<br>R<br>V<br>T<br>A | A<br>D<br>R<br>S<br>L<br>Q<br>G | C<br>I<br>L<br>P<br>Q<br>V | D<br>K<br>Q<br>V<br>Q<br>V<br>A<br>G<br>W | I<br>M<br>R<br>V<br>Y<br>L<br>S | L<br>I | T<br>V<br>S<br>G |

TABLE #3

Non-limiting examples of amino acid residues in FR3

| | Position | | | | | | | | | | | | | | | | |
|---|---|---|---|---|---|---|---|---|---|---|---|---|---|---|---|---|---|
| | 65 | 66 | 67 | 68 | 69 | 70 | 71 | 72 | 73 | 74 | 75 | 76 | 77 | 78 | 79 | 80 | 81 |
| a.a. residue anti-IgG CH1 a.a. sequences | G | R | F | T | I | S<br>A | R | D<br>Y<br>N | S<br>T | G<br>A | K<br>R | N<br>D<br>K | T<br>L | V | Y<br>F | L | Q |
| a.a. residue Camelid VHH's | A<br>D | | L<br>V | A<br>N<br>S | L<br>M<br>V | T<br>F<br>Y<br>T | H<br>I<br>L<br>Q<br>T<br>W<br>G<br>K<br>N<br>M<br>S | G<br>N<br>V<br>F<br>E<br>I<br>L<br>V<br>R<br>K<br>Y<br>G | A<br>D<br>F<br>S<br>I<br>L<br>V<br>P | D<br>N<br>Q<br>T<br>G<br>N<br>H<br>P | R<br>L<br>S<br>Q<br>T | E<br>S<br>I<br>Y<br>T<br>S<br>M<br>A<br>E | F<br>I<br>P<br>A<br>M<br>E | A<br>M<br>I<br>S<br>G<br>N<br>E<br>L | F<br>H<br>D<br>S<br>N | V<br>V | I<br>R<br>T<br>E<br>V<br>L |

| | Position | | | | | | | | | | | | | |
|---|---|---|---|---|---|---|---|---|---|---|---|---|---|---|
| | 82 | 82a | 82b | 82c | 83 | 84 | 85 | 86 | 87 | 88 | 89 | 90 | 91 | 92 | 93 | 94 |
| a.a. residue anti-IgG CH1 a.a. sequences | M | N<br>D | N<br>S<br>M | L | K<br>Q | P<br>A | E<br>D | D | T | A | V<br>I | Y | Y<br>F | C | A | G<br>A |
| a.a. residue Camelid VHH's | L<br>I<br>V | G<br>H<br>S<br>T | D<br>G<br>R<br>T | P<br>V<br>I | N<br>G<br>I<br>M | D<br>R<br>S<br>T | G<br>Q | | A<br>S | S<br>G | A<br>D<br>L<br>M | F<br>H<br>T<br>V | D<br>K<br>R<br>T | | G<br>V<br>C<br>F<br>K | |

TABLE #3-continued

Non-limiting examples of amino acid residues in FR3

| | | | | | |
|---|---|---|---|---|---|
| T | L | N | L | N | L |
| E | V | T | S | H | S |
| R | F | S | | V | I |
| | | R | | Y | R |
| | | | | S | T |
| | | | | F | |

TABLE #4

Non-limiting examples of amino acid residues in FR4

| | Position | | | | | | | | | |
|---|---|---|---|---|---|---|---|---|---|---|
| | 103 | 104 | 105 | 106 | 107 | 108 | 109 | 110 | 111 | 112 113 |
| a.a. residue anti-IgG CH1 a.a. sequences | W | G | Q | G | T | Q | V | T | V | S S |
| a.a. residue Camelid VHH's | P R S | D R A | E R K P | | A I | R L | I | I A N | A I | F | A L P T |

Method for Purification of Target Molecules

As indicated earlier herein, in a first aspect, the invention relates to a method for capturing a target molecule comprising an amino acid sequence as presented by a human IgG-CH1 domain. The method preferably comprises the steps of: a) bringing a composition comprising the target molecule in contact with the immunoadsorbent material comprising an antigen-binding protein of the invention, preferably immobilised on a support; and b) allowing capture of the target molecule with the immunoadsorbent material by specific binding to the antigen-binding protein, preferably under conditions that allow binding of the target molecules to the antigen-binding protein in the immunoadsorbent material.

Embodiments of the method for capturing the target molecule are suitable for use with any affinity capture protocol, including, e.g. the immunoassays as indicated herein above. Embodiments of the method for capturing the target molecule are further suitable for purification and/or concentration of one or more target molecules present in a fluid sample (see below) and/or for providing a fluid sample depleted of one or more target molecules, e.g. for use in proteomics applications.

Thus, in one embodiment of the method for capturing the target molecule, the method is method for purifying (and/or concentration) a target molecule. The method comprises capturing the target molecule onto the immunoadsorbent material in a capturing method as defined above. The method further comprises the step of: c) eluting the bound target molecule under conditions that decrease the affinity between the target molecules and the immunoadsorbent material. Elution of the bound target molecule preferrably is performed under mild elution conditions as herein defined above. Optionally, the method can comprise a further step d) for recovery of the target molecule and/or further processing target molecule, including e.g. formulation and/or packaging of the purified target molecule.

In a preferred embodiment, the target molecule that is to be purified is selected from the group consisting of human and humanized target molecules as herein defined above and; IgGs from baboon; Chimpanzee; Rhesus; cat; dog; guinea pig; syrian hamster; horse and donkey, and IVIG from these species. A target molecule to be purified, such as human IgG1, human IgG2, human IgG3 and/or human IgG4, can be a native, an intact, or a complete target molecule. In another embodiment, the target molecule comprising a human IgG-CH1 domain is a recombinant protein. The recombinant protein can be a fusion protein or a chimeric protein such as a humanized IgG.

In a preferred embodiment, an antigen-binding protein of the invention is able to selectively bind to a target molecule comprising a human IgG-CH1 domain as defined herein above.

Since the antigen-binding proteins of the present invention show comparable binding characteristics towards the CH1 domain of all 4 different human IgG subclasses, an immunosorbent material comprising one of said binding agents can be used for the selective purification of polyclonal IgG from e.g. human plasma (e.g. intravenous immunoglobulin [IVIG]) without affecting the parent IgG subclass distribution. An advantage of an antigen binding domain according to the present invention in the purification of Fab fragments, is that the antigen binding domain of the invention does not cross-bind to free light chains and Fc fragments.

In a preferred embodiment, the invention relates to a method for purification of Fab fragments from a composition that also comprises free light chains. This is especially advantageous for example in the production of recombinant human Fab fragments. Without wishing to be bound to any theory, in the production of recombinant (human) Fabs, a significant amount of free light chains is produced that are highly soluble and that are difficult to separate from the recombinant assembled Fabs using the antibody binding proteins available thus far, which also have affinity for free light chains. When using a method for purification of the present invention, assembled Fab fragments can be effectively separated from free light chains in a single step, producing a purified sample wherein free light chains cannot be detected.

The human IgG-CH1 domain is as defined under 'antigen-binding protein' above herein.

The composition comprising the target molecule will often be an aqueous composition comprising many other proteins besides the target that is to be purified. The conditions of the contact step are preferably such that binding of the binding agent, to the target molecule occurs. Preferably in this step a loading buffer having pH around 6.5 to 8 is used. A suitable buffer is e.g. a PBS buffer or similar buffer a physiological ionic strength and pH.

In an embodiment, the method is performed in the presence of a denaturing agent. Such a denaturing agent may be added to the composition before or during a method of the invention. A variety of denaturing agents can be used individually, sequentially, or in combination. The denaturing agent may comprise, for example, one or more chaotropic agent(s), lyotropic agent(s), organic denaturant(s), and/or detergent(s). Preferably, when the denaturing agent includes a detergent, the denaturing agent also includes one or more chaotropic agent(s), lyotropic agent(s), and/or organic denaturant(s), e.g., the denaturing agent further comprises a detergent, in addition to a chaotropic agent, lyotropic agent and/or organic denaturant.

Chaotropic agents may include a variety of different compounds, such as, for example, urea, $CNS^-$, and $CO_3COO^-$, guanidine HCl, $NO_3^-$, and $ClO_4^-$. Lyotropic agents may include, for example, acetate, e.g., sodium acetate (NaOAc). Organic denaturants may include, for example, acetonitrile (ACN). Detergents may include anionic, cationic, nonionic, or zwitterionic, detergent(s). Anionic detergents may include, for example, deoxycholic acid, cholic acid and SDS (sodium dodecyl sulfate); cationic detergents may include, for example, cetyltrimethylammonium bromide (CTAB). Nonionic detergents may include, for example, digitonin, triton, tween and nonidet 40 (NP40); Zwitterionic detergents may include, for example, CHAPS, CHAPSO, BigCHAP, CHAPS, ZWITTERGENT 3-08, ZWITTERGENT 3-10, ZWITTERGENT 3-12, ZWITTERGENT 3-14, and ZWITTERGENT 3-16.

Preferably, the denaturing agent is utilized with a buffer, e.g., to provide a denaturant fluid comprising at least one denaturing agent. A variety of buffers are suitable, for example, zwitterionic, phosphate, acetate, and carbonate. Zwitterionic buffers may include, for example, Tris buffer. Phosphate buffers, e.g., phosphate buffer solutions, may include, for example, sodium phosphate and potassium phosphate buffers. In an embodiment, the denaturing agent is selected from the group consisting of urea, CHAPS, guanidine HCl, CTAB, acetate, and acetonitrile. In some embodiments wherein at least one denaturing agent is urea, the urea has a concentration of at least about 0.8M, or at least about 1M, when placed in contact with the target molecule and/or the antigen-binding protein. In some embodiments wherein at least one denaturing agent is CHAPS, the CHAPS has a concentration of at least about 0.1%, or at least about 0.25%, when placed in contact with the target molecule and/or the antigen-binding protein. In some embodiments wherein at least one denaturing agent is guanidine HCL, the guanidine HCl has a concentration of at least about 0.03M, or at least about 0.05M, when placed in contact with target molecule and/or the antigen-binding protein. In some embodiments wherein at least one denaturing agent is acetonitrile, the acetonitrile has a concentration of at least about 8%, or at least about 10%, when placed in contact with target molecule and/or the antigen-binding protein.

The concentration of denaturing agent(s) placed in contact with the target molecule optionally may be adjusted to optimize the denaturation of the target molecule and/or the reduction of non-specific binding.

It is preferred that the loaded material is washed until the non specific binders have eluted. This is usually done by rinsing with a suitable buffer, which may be the same as the loading buffer. Desorption or elution of the target molecule is the next step. This is preferably done by changing the conditions such that the antibody or fragment no longer binds the target molecule. Elution may be achieved by changing the conditions with respect to pH, salt, temperature or any other suitable measure. A preferred elution method for desorption is elution with a buffer having a pH below 4, 3 or 2. Suitable elution buffers are described herein above.

The composition comprising the target molecule includes, but is not limited to, any quantity of a substance from a live or dead organism or a part thereof, such as for example blood, serum, plasma, urine, tears, cells, organs, tissues, bone, bone marrow, lymph, lymph nodes, synovial tissue, chondrocytes, synovial macrophages, endothelial cells, and skin. A composition comprising the target molecule can also be a composition comprising a recombinantly produced target molecule such as a microorganism, such as for example yeast, fungi, bacteria (e.g. *Escherichia coli*), or tissue culture cells, media, supernatants, filtrates and fermentation broths comprising the target molecule. A composition comprising the target molecule can also be a composition comprising a target molecule that has been treated with papain and/or pepsin, e.g. in order to produce Fab fragments from intact IgG molecules.

More specifically the invention relates to a method for the purification of a target molecule by immunoaffinity comprising the steps of: c) loading immunoadsorbent material comprising an antigen-binding protein of the invention with a composition comprising a target molecule, preferably under conditions where binding of the target molecule to the antigen-binding protein takes place; d) optionally, washing the loaded immunoadsorbent to remove non specific binders; and, e) eluting the target molecule by applying elution conditions. Optionally, the method can include the steps of a) selecting an antigen-binding protein or fragment thereof, that binds to the target molecule; and, b) binding the antigen-binding protein or fragment thereof to immunonoadsorbent material. Preferably a fragment of the antigen-binding protein retains binding affinity as defined above in the context of this invention. The method may further include the step f) of recovery of the target molecule and/or further processing target molecule, including e.g. formulation and/or packaging of the purified target molecule.

Use of an Antigen-Binding Protein for Detection and/or Purification

In a third aspect, the invention pertain to the use of an antigen-binding protein as defined herein or of an immunoadsorbent material as defined herein for the detection and/or purification of a target molecule comprising an amino acid sequence as presented by a human IgG-CH1 domain. Preferably, the amino acid sequence of the human IgG-CH1 domain is as described under 'antigen-binding protein' above. In a preferred embodiment, the target molecule to be detected and/or purified is as defined herein above. In a preferred embodiment, the detection and/or purification is in vitro detection and/or in vitro purification.

Therapeutic Aphereses

In a fourth aspect the invention relates to methods for therapeutic apheresis. Therapeutic apheresis is an extracorporeal blood treatment to eliminate pathogenic compounds from the blood (Bosch, 2003, J. Artif. Organs 6(1): 1-8). One example of TA concerns the adsorption of antibodies in a variety of antibody-mediated immune diseases. A commonly used matrix for adsorption of antibodies in TA is Protein A sepharose. This matrix is used for the treatment of various auto-immune diseases and antibody-mediated transplant rejections. However, due to low affinity for human IgG subclass 3 antibodies, Protein A matrix is not efficient in the removal of IgG3 antibodies. Advantageously, the antigen-binding proteins of the present invention that are specific for mammalian or human IgG can also be used for the depletion of IgG, including IgG3, in patients suffering from antibody-mediated diseases. Preferably the method for therapeutic apheresis comprises at least one of removing, depleting and inactivating human IgG in (from) a body fluid. Preferably the removing, depleting and inactivating of human IgG in (from) a body fluid is performed ex vivo. The body fluid preferably is blood, a blood fraction such as e.g. blood plasma or blood serum, or another body fluid. In the method an antigen-binding protein of the invention as defined hereinabove or an immunoadsorbent material comprising the antigen-binding protein as defined above, is brought into extracorporeal contact with the body fluid of a subject, preferably a human subject. The immunoadsorbent apheresis material may be in the form of particles or beads, which may advantageously be packed into a flow chamber or a column, through which the body fluid of the subject or patient is passed extracorporeally. Before or after a treatment in which IgG is depleted, one or more further treatment stages for the body fluid can be carried out. Several treatments of the body fluid can be carried out in successive units, in which IgG is depleted by adsorption, to achieve the desired end concentration of IgG. Samples of the body fluid before and after IgG depletion may be tested using e.g. ELISA for IgG levels (using e.g. the antigen-binding proteins of the invention). The body fluid may then be reinfused into the subject or human patient, although the latter step may be explicitly excluded from a preferred extracorporal embodiment of the method. In preferred embodiments the methods of the invention for therapeutic apheresis are applied on body fluids from patient or subjects suffering from an antibody-mediated autoimmune disease, antibody-mediated transplant rejection or an autoimmune disease with an antibody-mediated component. Examples of such diseases include Myasthenia gravis, Goodpasture syndrome, Systemic Lupus Erythematosis (SLE) and dilated cardiomyopathy (DCM). The apheretic methods of the invention are particularly useful for autoimmune diseases in which auto-antibodies of subclass 3 are involved, like e.g. SLE and DCM, as IgG3 is not efficiently depleted using Protein A (Staudt et al., 2002, Circulation 106: 2448-2453).

In one aspect the invention thus also pertains to the use of an antigen-binding protein of the invention that binds a mammalian IgG molecule for extracorporeal removal or depletion of mammalian IgG in a subject's body fluid, preferably a human subject.

Fusion Protein

In fifth aspect the invention relates to a fusion protein wherein the amino acid sequence of an antigen-binding proteins as defined herein is fused with an amino acid sequence of a therapeutic protein. The two amino acid sequences are preferably linked together by a genetic fusion wherein nucleotide sequences encoding the respective amino acid sequences are operably linked together in frame by means known per se in the art. The amino acid sequences may be linked directly or optionally through a spacer or linker amino acid sequence. The fusion proteins comprising an amino acid sequence of an antigen-binding protein of the invention fused to a therapeutic protein are useful in increasing the serum half-life of the proteins. Injected biotherapeutics may be rapidly cleared from the blood circulation after administration, requiring high doses or frequent administration to maintain effective therapeutic levels. To overcome these problems, the biotherapeutic proteins or peptides can be bound to circulating serum proteins such as IgGs to enhance their bioavailability. In the present invention the biotherapeutic proteins or peptides are bound to circulating IgGs by fusing the amino acid sequence of the biotherapeutic protein or peptide to that of an antigen-binding protein of the invention. This will enhance the bioavailability of the fused biotherapeutic protein or peptide. The genetic fusion of the antigen-binding proteins of the invention to biotherapeutics can provide a binding moiety directed to the CH1 domain of human IgG, resulting in increased half-life of the biotherapeutic in serum. Harmsen et al., (2005, Vaccine 23 (41), p. 4926-42) have indeed reported that binding of a model VHH with therapeutic potential to porcine IgG through a fusion with a VHH that binds porcine IgG resulted in an increase in the in vivo residence of the model VHH compared to a control fusion VHH that did not bind to porcine IgG. This method of improving serum half-life may be applied in principle to any biotherapeutic protein, including e.g. antigens (for vaccination), enzymes (for enzyme replacement therapy), hormones, chymokines, interleukins, (humanized) monoclonal antibodies, and the like.

Nucleic Acid

In a sixth aspect the invention relates to a nucleic acid comprising a nucleotide sequence encoding an antigen-binding protein as defined herein above. A preferred nucleic acid according to the invention is a nucleic acid construct, wherein the nucleotide sequence encoding the antigen-binding protein is operably linked to a promoter and optionally other regulatory elements such as e.g. terminators, enhancers, polyadenylation signals, signal sequences for secretion and the like. Such nucleic acid constructs are particularly useful for the production of the antigen-binding proteins of the invention using recombinant techniques in which a nucleotide sequence encoding the antigen-binding protein of interest is expressed in suitable host cells such as described in Ausubel et al., "Current Protocols in Molecular Biology", Greene Publishing and Wiley-Interscience, New York (1987) and in Sambrook and Russell (2001) "Molecular Cloning: A Laboratory Manual ($3^{rd}$ edition), Cold Spring Harbor Laboratory, Cold Spring Harbor Laboratory Press, New York). As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

Host Cell

In a seventh aspect, the invention pertains to a host cell comprising a nucleic acid as defined above. Preferably the host cell is a host cell for production of antigen-binding protein of the invention. The host cell may be any host cell capable of producing an antigen-binding protein of the invention, including e.g. a prokaryotic host cell, such as e.g., *E. coli*, or a (cultured) mammalian, plant, insect, fungal or yeast host cell, including e.g. CHO-cells, BHK-cells, human cell lines (including HeLa, COS and PER.C6), SD cells and Sf+ cells. A preferred host cell for production of an antigen-binding protein of the invention is however a cell of an eukaryotic microorganism such as yeasts and filamentous fungi. Preferred yeast host cell e.g. include e.g. *Saccharomyces cerevisiae, Pichia pastoris, Hansenula polymorpha*, and *Kluyveromyces lactis*. Preferred strains, constructs and fermentation conditions for production of the antigen-binding protein of the invention are described by van de Laar, et al., (2007, Biotechnology and Bioengineering, Vol. 96, No. 3: 483-494). For example, production of the antigen-binding proteins can be performed in standard bioreactors with a working volume between 10 and 10,000 liters. Dissolved oxygen can be controlled by automatic adjustment of the impeller speed. The pH can be controlled using phosphoric acid and ammoniac gas or ammonia solution and temperature controlled via e.g. a cooling jacket and heating jacket.

The offgas is analysed on ethanol concentration, rO$_2$ and rCO$_2$. The batch phase is started by adding 3%-8% of full-grown inoculum (e.g. 30° C., 0.3-0.4 VVM air, DO$_2$ minimum 30%, pH 5.0). When the ethanol concentration in offgas is declining in batch phase the ethanol fermentation can be started. The feed can be applied according to a pulsed feed profile to maintain the ethanol level within the demanded margins. The feed phases can be performed at 21° C. and 0.7-1.1 VVM air. During the ethanol fermentations DO$_2$ decreases to 0% and accumulated ethanol can be further controlled by a pulsed feed profile. Feed phase stops when the ethanol feed is depleted. The broth can be chilled to a temperature between 5-10° C. till further processing like biomass removal etc. (VVM=volumes of air per minute per volume of batch). In this context it is also understood that whenever herein we refer to an antigen-binding protein of the invention as being obtainable by expression in yeast at a certain minimal expression level, this level is obtained using the method as described in Example 1.1. of WO 97/25591 or Van der Laar (2007) Biotechnology and Bioengineering 96(3):483-494. Van der Laar et al. provides the (maximal) concentration of the antigen-binding protein (at the end of fermentation) for several VHH ligands. "g/L" refers to the amount of secreted antigen-binding protein (in grams) per liter of cell-free broth (i.e., after removal of biomass by e.g. filtration). Selection and generation of antigen specific VHH fragments is described in Frenken et al. (2000) Journal of Biotechnology 78:11-21.

Method for Producing Antigen-Binding Protein

Thus, a further aspect the invention relates to a method for producing an antigen-binding protein of the invention, wherein the method preferably comprises the steps of: a) culturing a host cell as defined above under conditions conducive to expression of the antigen-binding protein; and optionally, b) purifying the antigen-binding protein from at least one of the host cell and the culture medium. Suitable conditions may include the use of a suitable medium, the presence of a suitable source of food and/or suitable nutrients, a suitable temperature, and optionally the presence of a suitable inducing factor or compound (e.g. when the nucleotide sequences of the invention are under the control of an inducible promoter); all of which may be selected by the skilled person. Under such conditions, the amino acid sequences of the invention may be expressed in a constitutive manner, in a transient manner, or only when suitably induced. The antigen-binding proteins of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence of the invention) and/or preparative immunological techniques (i.e. using antibodies against the antigen-binding protein to be isolated).

Composition

In a further aspect, the invention relates to a composition comprising an antigen-binding protein as defined herein. A preferred embodiment thereof is an immunoadsorbent material comprising the antigen-binding protein. An immunoadsorbent material is herein understood to mean the combination of a carrier and an antigen-binding protein that is immobilized on the carrier. Preferably in the immunoadsorbent material the antigen-binding protein is immobilized onto a carrier, whereby more preferably, the antigen-binding protein is immobilised onto the carrier by a covalent link.

The carrier may be any material that may be used to for immobilization of an antigen-binding protein. Suitable examples are matrix materials, to entrap the binding agent, cell surfaces on which the binding agent is displayed and polymers that can be covalently linked to the binding agent. The person skilled in the art of affinity chromatography is well aware of suitable carriers such as e.g. porous solid phase carrier materials such as agarose, polystyrene, controlled pore glass, cellulose, dextrans, kieselguhr, synthetic polymers such as Sepharose™, porous amorphous silica. The carrier materials may be in any suitable format such as particles, powders, sheets, beads, filters and the like. Further specifications of suitable carrier materials are for example disclosed in EP-A-434317. Methods are available for immobilizing ligands quickly, easily and safely through a chosen functional group. The correct choice of coupling method depends on the substance to immobilized. For example the following commercially known derivatives of Sepharose™ allow the convenient immobilization of proteins thereon: CNBr-activated Sepharose™ 4B enables ligands containing primary amino groups to be rapidly immobilized by a spontaneous reaction. AH-Sepharose™ 4B and CH-Sepharose™ 4B both have a six-carbon long spacer arm and permit coupling via carboxyl and amino groups respectively. Flexible spacers are suitable for use in situations where the flexibility of the target molecules is limited or where 3-dimensional structure of the target requires some flexibility of the binding agent to allow optimal binding. Activated CH-Sepharose™ 4B provides a six-carbon spacer arm and an active ester for spontaneous coupling via amino groups. These are only a few examples of suitable immobilisation routes. Optionally the immunoadsorbent material is put into a column to facilitate easy chromatographic separations.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

Blot B: Protein-G biotin (5 μg/ml in 1% (w/v) milk powder 0.05% Tw-20 in PBS)/streptavidin-AP (1:2000)

Blot C: anti IgG-CH1 VHH, His tagged (5 μg/ml in sample buffer)/Mouse anti-His-AP (1:2000)

Blot D: anti human Fab-kappa VHH, His-tagged (5 μg/ml)/Mouse anti-His-AP (1:2000)

Figure 4:
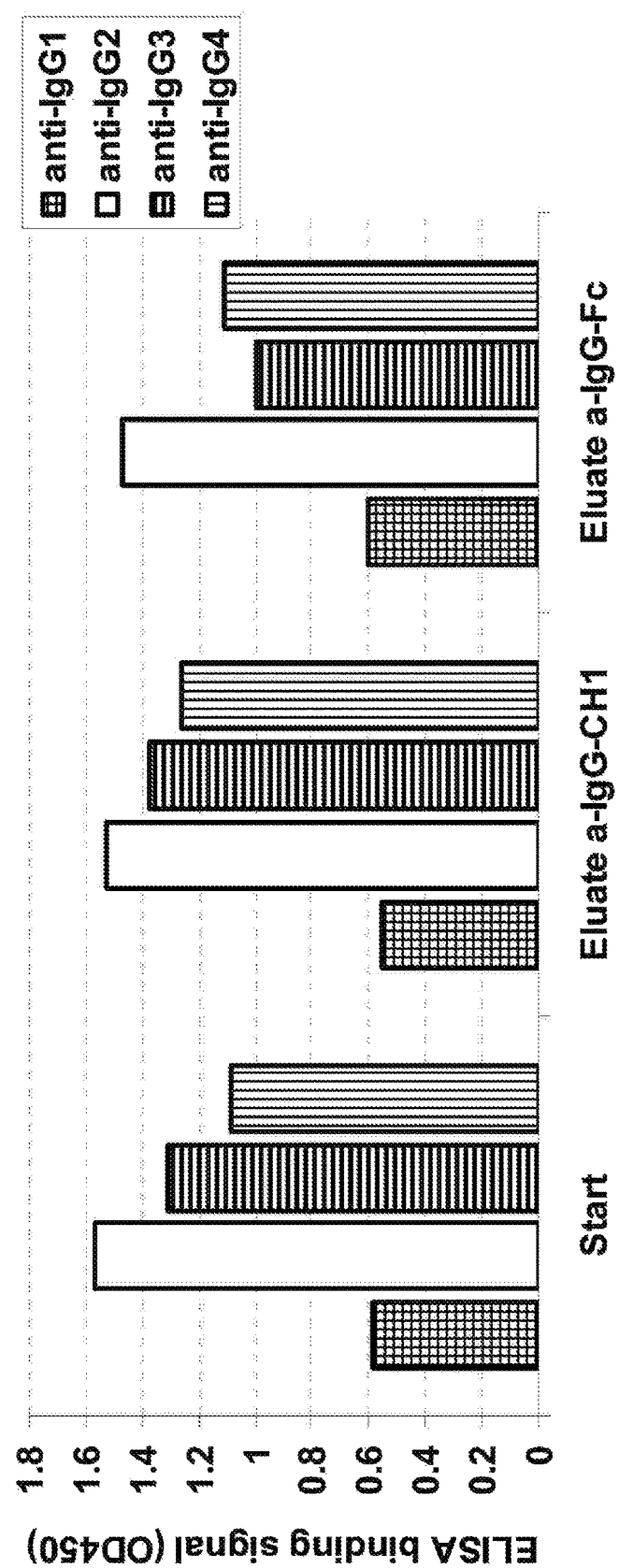
Figure 5A:
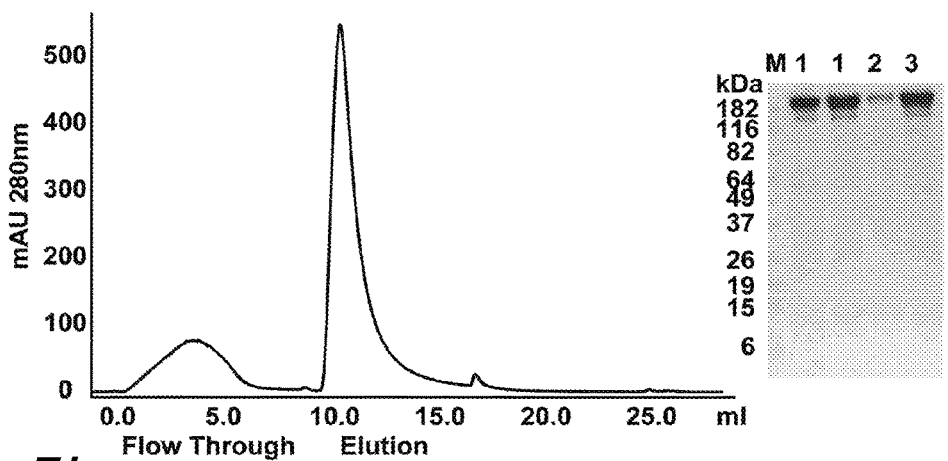

Blot E: anti human IgG-Fc VHH, His-tagged (5 μg/ml)/ Mouse anti-His-AP (1:2000) Western blots B to E were developed using BCIP/NBT as a substrate FIG. 4. Binding patterns of a set of human IgG subclass specific mouse Mabs in ELISA on polyclonal human IgG starting material and corresponding elution fractions of different antibody binding affinity resins FIG. 5. IgG domain selectivity of anti IgG-CH1 affinity resin (A) Polyclonal human IgG antibodies; (B) Polyclonal human IgG-Fc fragments; (C) Polyclonal human IgG-Fab fragments; M: molecular weight marker, lanes 1: start material, lanes 2: flow through, lanes 3: elution fraction FIG. 6. Purification of human IgG Fab fragments on different affinity resins (A) Anti IgG-CH1 affinity resin; (B) Protein G affinity resin FIG. 7. Purification of human IgG Fab fragments from an IgG/papain digestion mixture (A) CBB stained SDS page gel (non reducing); M: molecular weight marker; lane 1: Untreated polyclonal human IgG; lane 2: Starting material: papain treated human IgG in digestion buffer (0.02 M cysteine, 20 mM NaPhosphate pH 7.4, ±7 mg/ml); lane 3: Flow through fraction of anti human IgG-Fc VHH resin after loading of starting material (diluted in PBS, ±1 mg/ml); lane 4: Elution fraction of anti human IgG-Fc VHH resin (B) CBB stained SDS-page gel; Purification of Fab fragments from a human IgG-papain digestion mixture using an anti IgG-CH1 VHH resin after depletion of IgG Fc fragments, intact and/or partially digested IgG by an anti IgG-Fc VHH resin. M: molecular weight marker; lane 1: Starting material: i.e. flow through fraction of anti human IgG-Fc VHH resin after loading of human IgG/papain digestion sample (diluted in PBS, ±1 mg/ml); lane 2: Flow through of anti human IgG-CH1 VHH resin after loading of starting material; lane 3: Elution fraction of anti human IgG-CH1 VHH resin

EXAMPLES

Example 1. Identification of IgG-CH1 Binding VHH Fragments

The VHH fragments binding to the CH1 domain of IgG antibodies were identified from llamas immunized with human IgG antibodies and/or Fab fragments thereof. Screening of individual VHH fragments from the constructed expression libraries was performed by ELISA using different human antibody isotypes and subclasses and fragments thereof, which resulted in identification of a panel of VHH fragments binding to the CH1 domain of IgG from different mammalian species and human IgG1 to 4 in particular.

For screening purposes Maxisorp binding plates (Nunc) were coated with human antibody antigens and subsequently blocked with 2% (w/v) milk powder (Protifar) in PBS. Bound VHH fragments were detected by either a mouse anti-Myc mAb in combination with a polyclonal goat-anti-mouse-HRP conjugate (Bio-Rad, 172-1011) or a polyclonal rabbit anti-llama-VHH serum in combination with a polyclonal swine-anti-rabbit IgG-HPO conjugate (Dako, P217). From this screening a set of VHH fragments was identified that showed binding to polyclonal human IgG and Fab fragments thereof and to the following human IgG antibodies; human IgG1-kappa, human IgG-1-lambda, human IgG3-lambda and human IgG4-kappa. No binding was observed for polyclonal human IgG Fc fragments and human IgM. These results indicated that this panel of VHH fragments recognize an epitope present on the Fab portion of human IgG antibodies and that binding to this epitope enables binding of all 4 human IgG subclasses independent of its type of light chain (kappa or lambda). Since no binding was observed towards human IgM (also comprising a light chain and a VH domain like in IgG), said epitope is present on the CH1 domain of IgG antibodies.

The IgG binding reactivity of this panel of anti IgG-CH1 VHH fragments was further determined using surface plasmon resonance analysis (SPR) on a Biacore 3000. For this purpose the binding agents were immobilized onto the surface of a CM5 sensor chip. Subsequently, the sensor chips were incubated with purified antibodies and/or fragments thereof (20 μg/ml) in HBS-EP buffer (0.01 M HEPES, pH7.4; 0.15 M NaCl; 3 mM EDTA; 0.005% Surfactant P20). Binding was allowed for 1 minute at 5 μl/min followed by a dissociation step of 2.5 minutes at 5 Binding signals (Resonance Units, RU) were compared to background signals measured with HBS-EP buffer only. Results are summarised in Table 5.

TABLE 5

Antibody domain selectivity of IgG-CH1 binding VHH fragments in Biacore

| Antibody antigen | Estimated mol. weight (kDa) | Binding Reactivity* |
| --- | --- | --- |
| HuIgG | 150 | + |
| Human IgA | 150-300 | − |
| Human IgM | 750 | − |
| Human IgG, Fab fragments | 50 | + |
| Human IgG, Fc fragments | 50 | − |
| Human IgG1-kappa | 150 | + |
| Human IgG1-lambda | 150 | + |
| CL-VL-kappa (Bence Jones) | 25 | − |
| CL-VL-lambda (Bence Jones) | 25 | − |
| Human IgG1, CH2 (rec.) | 12.5 | − |
| Human IgG1, CH3 (rec.) | 12.5 | − |
| Human IgG1, CH2—CH3 (rec.) | 25 | − |
| Human IgG1, CH1—CL-kappa | 25 | + |
| Human IgG1, CH1—CL-lambda | 25 | + |
| Human scFv #1 | 25 | − |
| Human scFv #2 | 25 | − |
| Human scFv #3 | 25 | − |
| Buffer | − | − |

*(+) positive binding; >400 RU in Biacore (−) no binding; <5 RU in Biacore

As also demonstrated in ELISA, no binding was observed for human IgG-Fc fragments and human IgM. The IgG-CH1 binding epitope was further confirmed by a lack of binding towards human IgA, free human kappa- and lambda light chains (Bence Jones proteins) and human scFv fragments in Biacore. This demonstrates no binding reactivity towards the VH domain as present in human IgM, IgA and in human scFv, nor towards any epitope present on the light chains of IgG antibodies.

IgG-CH1 specificity was further confirmed by observed binding reactivity against antibody domain constructs only comprising a CH1—and a CL domain of a human IgG1 antibody (i.e. the constant domains of an IgG1 Fab fragment). This binding was independent of the subclass of the CL domain (i.e. kappa or lambda).

As reported by Derrick et. al. low affinity cross-binding towards some IgG Fab fragments is observed for Protein G through binding to CH1, however, unlike protein G the antigen binding proteins of the current invention show binding to all human IgG Fab fragments and do not cross-bind with the Fc region of human IgG antibodies.

Example 2. DNA Sequencing of IgG-CH1 Binding VHH Fragments

Figure 1:
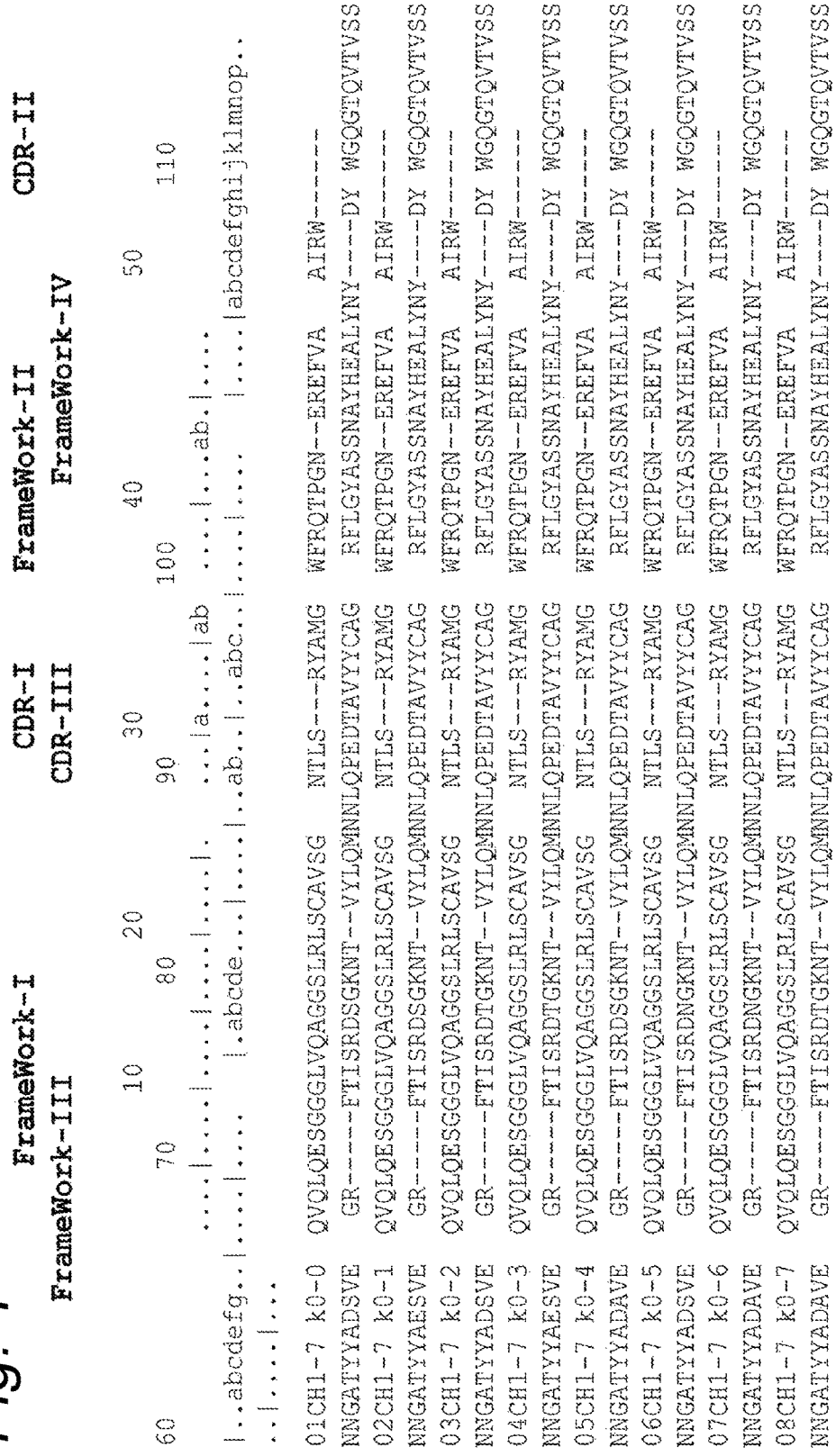
FIG. 1. Amino acid sequences of anti-IgG-CH1 VHH fragments and CDRs thereof
anti-IgG-CH1 VHH fragments: SEQ ID No's: 1-158
anti-IgG-CH1 VHH CDR's: CDR1: SEQ ID No's: 159-162, CDR2: SEQ ID No's: 163-181, CDR3: SEQ ID No's: 182-185

The amino acid sequences of the anti IgG-CH1 binding VHH fragments were determined via DNA sequencing and is presented in FIG. 1 (SEQ ID's: 1 to 158). Although the isolated VHH fragments originate from different llamas immunized with different types of antibody antigens, the CDR regions of all sequenced anti IgG-CH1 VHH fragments show remarkable similarities, thereby indicating recognition of the same epitope as present on the CH1 domain of IgG antibodies. The IgG-CH1 epitope being recognized by the antigen-binding proteins of the current invention therefore seems to be unique in its ability to generate an immune response in the llama through eliciting a significant enrichment of anti IgG-CH1 VHH antibody fragments belonging to a rather conserved sequence family.

Example 3. IgG Species Selectivity of IgG-CH1 Binding VHH Fragments in Biacore In order to further specify the epitope on IgG CH1 domains that is recognized by the antigen-binding proteins of the current invention, the binding reactivity's towards IgGs from a panel of different species were analyzed using surface plasmon resonance analysis (SPR) on a Biacore 3000 system. Based on the observed cross-species reactivity, the different CH1 amino acid sequences could then be aligned and analysed on potential unique and/or discriminating residues and/or residue combinations. For this purpose the binding agents were immobilized onto the surface of a CM5 sensor chip. Subsequently, the sensor chips were incubated with purified IgG antibodies (20 µg/ml) and/or serum (20× diluted) from different species in HBS-EP buffer (0.01 M HEPES, pH7.4; 0.15 M NaCl; 3 mM EDTA; 0.005% Surfactant P20). Binding was allowed for 1 minute at 5 µl/min followed by a dissociation step of 2.5 minutes at 5 µl/min. Binding signals (Resonance Units, RU) were compared to background signals measured with HBS-EP buffer only. Results are summarised in Table 6.

TABLE 6

Species selectivity of IgG-CH1 binding VHH fragments in Biacore

| Antibody antigen | Binding Reactivity* |
| --- | --- |
| HuIgG | + |
| Chimpanzee IgG | + |
| Rhesus IgG | + |

TABLE 6-continued

Species selectivity of IgG-CH1 binding VHH fragments in Biacore

| Antibody antigen | Binding Reactivity* |
| --- | --- |
| Rat IgG | − |
| Mouse IgG | − |
| Rabbit IgG | − |
| Syrian Hamster IgG | + |
| Guinea Pig IgG | + |
| Dog IgG | + |
| Cat IgG | + |
| Bovine IgG | − |
| Goat IgG | − |
| Sheep IgG | − |
| Swine IgG | − |
| Horse IgG | + |
| Donkey IgG | + |
| Llama IgG | − |
| Chicken IgY | − |
| Buffer | − |

*(+) positive binding; >250 RU in Biacore (−) no binding; <5 RU in Biacore

As analysed with a set of IgG samples originating from different species, a unique cross-reactivity profile was observed for the IgG-CH1 binding VHH fragments. For instance, no binding was found for IgG from "even toed ungulates" like swine, bovine, goat, sheep and llama, whereas the CH1 domain of IgG from "odd toed ungulates", like horse and donkey did show significant binding signals.

For rodent derived IgG samples, no binding was observed towards IgG of the murine subfamily (mouse and rat), whereas IgG's from guinea pig and (syrian) hamster, each belonging to a different subfamily within the order of rodentia, could be recognized. The anti IgG-CH1 VHH fragment did not recognize rabbit IgG (belonging to the order of Lagomopha).

Good binding was observed for both dog and cat IgG and as expected for chimpanzee—and rhesus IgG, both belonging to the order of primates. Although rhesus monkeys belong to a different primate family than humans and chimpanzees, comparable binding reactivity's were observed.

Based on the observed cross-species reactivity, the different CH1 sequences as available in the public domain (www.uniprot.org) were aligned and analysed on potential unique and/or discriminating residues and/or residue combinations within the different IgG-CH1 regions that could be linked with the observed CH1 binding reactivity. A schematic overview of the different CH1 sequences numbered according to Kabat (Vol 1 (1991) fifth edition, US Department of Health and Human Services, NIH publication No. 91-3242) is presented in FIG. 2.

Figure 2:
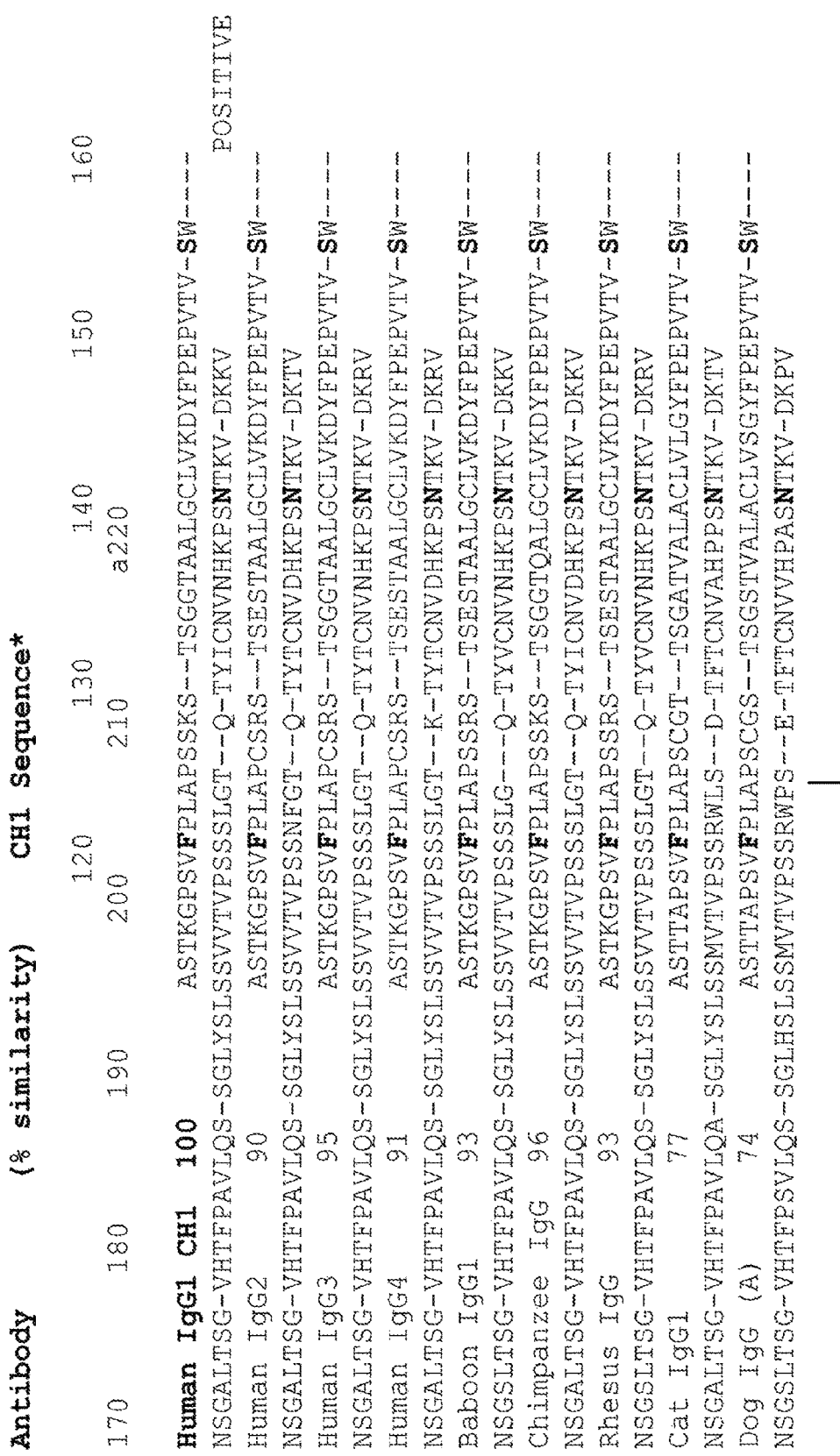
FIG. 2. CH1 sequences of different IgG species grouped on basis of observed binding reactivity with anti IgG-CH1 VHH fragments in Biacore
* according to Kabat numbering, 1991, Vol 1, fifth edition, US Department of Health and Human Services, NIH publication No. 91-3242.
Sequences correspond to SEQ ID No's: 190-217
residues in bold: present at given position in CH1 domains recognized by anti IgG-CH1 VHH fragments residues underlined: only present at given position in CH1 domains not recognized by anti IgG-CH1VHH fragments FIG. 3. Binding reactivity of antigen binding proteins towards human IgG and Fab fragments thereof in Western blot M: prestained marker; IgG: polyclonal human IgG; Fab: polyclonal human IgG-Fab fragments; NR: non-reduced; R: Reduced Gel A: CBB stained SDS page gel (4-20% Tris-Glycine) of polyclonal human IgG and human IgG-Fab fragments (Jackson Immunoresearch) denatured in SDS sample buffer with and without β-mercaptethanol; i.e. reduced (R) and non-reduced (NR).

Based on the observed species selectivity as shown in Table 6 and the amino acid sequences of the different IgG-CH1 domains as outlined in FIG. 2 one can conclude that the IgG-CH1 binding VHH fragments of the current invention bind to an epitope present on the CH1 domain of an antibody heavy chain of the IgG isotype, and said CH1 domain being characterized in having a phenylalanine residue (Phe, F) at position 122 but not a tyrosine (Tyr, Y) at position 122 and having none or at maximum one cysteine residue (Cys, C) at position 127 or 128 and having a serine (Ser, S) or a lysine residue (Lys, K) at position 156 but not a threonine (Thr, T) at position 156 and an asparagine (Asn, N) or a serine (Ser, S) at position 216, like displayed in naturally occurring IgG-CH1 domains as listed in FIG. 2. An overview of said residues and residue positions that are indicated to play a role in the binding reactivity of the antigen-binding proteins of the current invention is presented in Table 7.

Table 7 clearly demonstrates that none of the IgG-CH1 domains that possess a tyrosine (Tyr, Y) at position 122 are being recognized by the anti IgG-CH1 VHH fragments indicating this residue at this position to be discriminative with respect to epitope binding. In addition, none of the CH1 domains having a threonine (Thr, T) at position 156 are being recognized by the anti IgG-CH1 VHH fragments, as well as none of the CH1 domains having a cystein (Cys, C) at both positions 127 and 128. Except for guinea pig IgG, all IgG species being recognized by the anti IgG-CH1 VHH fragments have an asparagine residue (Asp, N) at position 216 and as such also being indicative for the binding of an IgG-CH1 domain with the anti IgG-CH1 VHH fragments.

As reported by Derrick et. al. (J. Mol. Biol. (1994) 243, 906-918) Protein G shows some binding reactivity towards the CH1 domain of IgG antibodies as well. However, Derrick et. al. shows that Protein G binds to Fab fragments of both mouse and human IgG. The antigen-binding proteins of the current invention do not show any binding towards mouse IgG-CH1 domains thereby indicating the involvement of different residues within the CH1 epitope that is recognized by Protein G.

TABLE 7

Identification of key residues in IgG-CH1 domains correlating with species selectivity of the anti-IgG-CH1 VHH fragments

| Antibody antigen | Binding reactivity anti IgG-CH1 VHH fragments* | CH1 residue at pos. 122** | 127-128 | 156 | 216 |
|---|---|---|---|---|---|
| BINDING | | | | | |
| Human IgG1 | + | F | - - | S | N |
| Human IgG2 | + | F | C - | S | N |
| Human IgG3 | + | F | C - | S | N |
| Human IgG4 | + | F | C - | S | N |
| Chimpanzee IgG | + | F | - - | S | N |
| Rhesus IgG | + | F | - - | S | N |
| Cat IgG1 | + | F | - C | S | N |
| Dog IgG | + | F | - C | S | N |
| Guinea Pig IgG2 | + | F | - C | K | S |
| Horse IgG1 | + | F | - C | S | N |
| NO BINDING | | | | | |
| Rabbit IgG | - | F | C C | T | N |
| Swine IgG1 | - | Y | C - | T | T |
| Swine IgG2 | - | Y | C - | T | T |
| Bovine IgG1 | - | Y | C C | T | S |
| Bovine IgG2 | - | Y | C C | T | S |
| Sheep IgG1 | - | Y | C C | T | S |
| Goat IgG1 | - | Y | C C | T | S |
| Llama IgG | - | Y | - C | T | S |
| Rat IgG1 | - | Y | - - | T | S |
| Rat IgG2a | - | Y | - - | T | S |
| Rat IgG2b | - | Y | - C | T | S |
| Rat IgG2c | - | Y | - C | K | K |
| Mouse IgG1 | - | Y | - - | T | S |
| Mouse IgG2a | - | Y | - C | T | S |
| Mouse IgG2b | - | Y | - C | T | S |
| Mouse IgG3 | - | Y | - C | K | K |

*Based on binding reactivity towards polyclonal and monoclonal IgG samples in Biacore and ELISA
**Numbering according to Kabat numbering, 1991, Vol 1, fifth edition, US Department of Health and Human Services, NIH publication No. 91-3242
residues in bold: present at given position in CH1 domains recognized by anti IgG-CH1 VHHs
residues underlined: only present at given position in CH1 domains not being recognized by anti IgG-CH1 VHH fragments Derrick et. al. further states that the substitution Y129F (in our scheme this corresponds to Y122F, see FIG. 2) is not seriously deleterious to the CH1 binding of Protein G. Unlike with Protein G, we clearly observed that a tyrosine (Tyr, Y), when present at this position, does have a big impact in CH1 binding on the antigen-binding proteins of the current invention (see also Table 7). In fact, none of the anti IgG-CH1 VHH fragments showed any binding towards a CH1 region having a tyrosine at that position within the set of naturally occurring IgG-CH1 domains analysed. Derrick et al further reports that most of the interactions between Protein G and the IgG-CH1 domain resides at the c-terminus of the CH1 domain and include residues that are highly conserved among the different CH1 species, like threonine (Thr, T) at position 217 and lysine (Lys, K) at position 218 (according to FIG. 2) and as such contributing to Protein G's ability to bind to both mouse and human IgG-CH1 domains. This further confirms that the antigen-binding proteins of the current invention recognize a different epitope than Protein G since no binding is observed for e.g. mouse IgG-CH1 domains and CH1 domains possessing a tyrosine (Tyr, Y) at position 122.

The identified IgG-CH1 binding VHH fragments originate from a llama immunized with human antibodies and/or fragments thereof all comprising an IgG CH1 domain. As expected none of these VHH fragments show reactivity towards the CH1 domain of "classical" tetrameric llama IgG antibodies since the immune system rules out induction of antibodies against self-antigens. The CH1 domains of said llama IgG antibodies can also be characterized in having a tyrosine residue (Tyr, Y) at position 122 and a threonine (Thr, T) at position 156 (see FIG. 2).

Based on the above findings, it becomes unlikely that antibodies with the same binding characteristics as the antigen-binding proteins of the current invention, can be generated from animal species that themselves display IgG-CH1 domains comprising a phenylalanine (Phe, F) at position 122 and a serine (Ser, S) or a lysine (Lys, K) at position 156. Remarkably, no mouse—or rat IgG antibodies (both having Y 122 and T or K at 156 in CH1) have been described in the prior art that show the same binding reactivity as the panel of anti IgG-CH1 VHH fragments. On the other hand, it has been described that clefts on protein surfaces are avoided by antigen-combining sites of conventional tetrameric antibodies, in contrast to heavy-chain antibodies. In case such or other VHH related properties in antigen binding also plays a role in the ability of binding to CH1 domains, one can at least expect that antigen-binding proteins of the current invention can also be obtained from animals possessing heavy-chain antibodies like e.g. camels, dromedary, nurse sharks and ratfish, not having a tyrosine (Tyr, Y) at position 122.

As determined, none of the binding domains of the current invention bind to a CH1 region having a tyrosine (Tyr, Y) at position 122. No other types of antigen-binding proteins, like Protein G, A, L and even monoclonal antibodies, are known or described in the prior art that bind to the same epitope on IgG-CH1 as being recognized by the antigen-binding proteins of the current invention, thereby providing binding reactivity towards CH1 domains of all four human IgG subclasses in particular and Fab fragments thereof independent of the type of light chain and showing no cross-binding towards any other domain as present on IgG molecules, such as Fc (CH2-CH3), VH and both kappa- and lambda light chains.

Example 4. Binding Reactivity of Antigen-Binding Proteins Towards Human IgG Domains in Western Blot Different antigen-binding proteins were tested in western blot analysis to determine the ability to bind to reduced- and non-reduced denatured human IgG and human IgG-Fab samples after running SDS page. For this purpose c-terminal his tagged VHH fragments (i.e. anti IgG-CH1 VHH, anti human Fab-kappa light chain VHH and anti human IgG-Fc VHH) were analysed and compared with Protein-G (biotinylated). Results are displayed in FIG. 3. Results showed that Protein G and the anti human IgG-Fc VHH fragment only bind to non-reduced denatured human IgG and not to Fab fragments thereof. Both the anti IgG-Fc VHH and Protein G did not show any binding signals towards human Fab fragments, which was expected for the anti human IgG-Fc VHH. In this respect, no binding of Protein G to human Fab is observed due to its low affinity for human CH1.

Both the anti IgG-CH1—and the anti human Fab-kappa light chain VHH (directed against the CL domain of human kappa light chains) were able to bind to both denatured (non-reduced) human IgG antibodies and Fab fragments thereof. This may therefore suggest recognition of a more linear epitope presented by the CH1 domain in contrast to a conformational epitope. However, when both IgG and Fab samples were denatured in SDS sample buffer and reduced by means of e.g. β-mercaptoethanol, no binding signals were observed with any of the tested antigen-binding proteins. For the antigen-binding proteins of the current invention (binding to CH1) this may indicate that disruption of the intra-chain cystein bridge within the CH1 domain alters the binding epitope thereby resulting in a lack of recognition.

Example 5. Chromatography Testing of Anti IgG-CH1 VHH Fragments

The anti IgG-CH1 VHH fragments were expressed by the yeast *S. cerevisiae* as described in WO 94/18330 in shake flask. After purification the anti IgG-CH1 VHH fragments were dialysed to NHS coupling buffer and coupled to NHS activated sepharose 4B Fast Flow according to the suppliers protocol (GEHC) and as described in WO2006/059904. All anti IgG-CH1 VHH fragments were immobilized at a ligand density of at least 5 mg/ml resin. Columns were made of the coupled antibody matrix using HR 5/5 columns (GEHC). A column volume of 400 µl was used. All the chromatography experiments were performed on an Akta explorer 100. Purified polyclonal human IgG samples were loaded in PBS pH 7.4 (e.g. 10 ml human IgG at 0.5 mg/ml in PBS, pH 7.4 at a flow rate of 150 cm/hr) and eluted using a primary elution step with 20 mM citric acid pH 3.0. A secondary elution step with PBS pH 2.1 (i.e. PBS with addition of 8 M HCl to yield pH 2.1) was performed to determine the elution efficiency of the primary elution buffer. Protein detection was performed on line by monitoring the signal of $OD_{214}$ and $OD_{280}$. The binding capacity was calculated by comparing the total peak areas of both the flow through and elution peaks. An overview of the binding capacities of the tested anti IgG-CH1 sepharose carriers in chromatography are given in Table 8.

TABLE 8

Dynamic binding capacities (DBC) in mg/ml of anti-IgG-CH1 resins for human IgG

| anti IgG-CH1 VHH # | DBC (mg/ml) | anti IgG-CH1 VHH # | DBC (mg/ml) |
|---|---|---|---|
| 01 | 8.74 | 82 | 6.69 |
| 10 | 12.0 | 83 | 8.46 |
| 19 | 9.4 | 84 | 8.27 |
| 28 | 12.5 | 85 | 11.88 |
| 37 | 9.8 | 86 | 4.98 |
| 46 | 11.2 | 87 | 5.64 |
| 55 | 11.3 | 88 | 7.31 |
| 64 | 10.2 | 89 | 5.61 |
| 73 | 11.7 | | |

Results demonstrated all tested anti IgG-CH1 VHH fragments to be functional in binding and elution of human IgG in chromatography after random covalent coupling to NHS-Sepharose.

Within this coupling procedure the epsilon amine groups of lysine residues are mainly involved in generating covalent links with the active groups of the resin, next to e.g. the alpha amine group of the amino terminus of the VHH domain. Within the sequence of a VHH fragment there are 4 positions that commonly display a lysine residue (i.e. position 43, 64, 75 and 83 according to the numbering as depicted FIG. 1). Although it has been shown that even without an appending C-terminal peptide or tag, VHH fragments retain their functionality after covalent coupling, influence of the number of commonly occurring lysine residues and the positions of said lysine residues within a VHH sequence on resin performance after covalent coupling to e.g. NHS sepharose can be expected. In this respect, generating variants based on these lysine residues could therefore serve as a strategy to improve functionality of the immobilized VHH fragment resulting in e.g. improvement of the dynamic binding capacity for its target antigen. To illustrate, anti IgG-CH1 VHH#28, which only differs one residue with VHH#1 (Q83K) thereby possessing one additional lysine residue, shows an improved binding capacity for human IgG compared to VHH#1. Furthermore, additional lysine residues can also alter the pI of the VHH fragment, e.g. increasing from 5.66 (VHH#1) to 7.41 (VHH#28) determined by GPMAW 7.01 software, which can also favour purification of VHH fragments by e.g. ionic exchange chromatography.

Example 6. IgG Subclass Distribution of Affinity Purified Polyclonal Human IgG Using Resins with Different Human IgG Binding Proteins In order to verify the observed comparable binding affinity of the anti IgG-CH1 VHH fragments for the different human IgG subclasses and the possible use of such antigen-binding proteins in the manufacturing of e.g. Intra Venous Immune Globulins (IVIG) from human plasma, polyclonal human IgG was loaded in excess onto sepharose resins immobilized with either an anti IgG-CH1 VHH fragment (VHH #01) or an anti human IgG-Fc VHH fragment (ligand density of ±15 mg/ml resin). The latter VHH fragment was known to display comparable binding affinities for the human IgG subclasses 1, 2 and 4 (all ±1 nM), but demonstrated a significant weaker binding affinity towards human IgG3 (±48 nM). The calculated DBC of the anti IgG-CH1— and anti human IgG-Fc resin was 28—and 24 mg human IgG/ml resin, respectively. Both resins were overloaded with polyclonal human IgG with ±2.5 times the DBC (corresponding to 50 mg human IgG/ml resin). In case the binding affinity for a certain human IgG subclass is less, the other IgG subclasses will more effectively compete for binding to the immobilized VHH ligands during overloading the resin with polyclonal human IgG. By subsequent analysis of the subclass distribution of the eluted fraction, the IgG subclass having the lowest binding affinity for the resin is expected to be under represented compared to the starting material. Applicability of the affinity resin is shown when both the starting material and the elution fraction show a comparable subclass distribution even after overloading of the resin prior to elution.

Subclass distribution of both the starting material and the elution fractions were determined by ELISA through measuring the relative binding signals of human IgG subclass specific mouse monoclonal antibodies (biotin conjugates, Sigma) towards the different samples coated onto the surface of an Maxisorp plate. Results are displayed in FIG. 4. Results showed comparable binding patterns of the different subclass specific mouse Mabs for the starting material and eluate fraction of the anti IgG-CH1 resin. The eluted human IgG's from the anti human IgG-Fc resin, however, clearly demonstrated a relatively lower response with the anti human IgG3 mouse Mab, indicating a clear decrease in the level of human IgG3 in the eluted fraction compared to the starting material. The anti IgG-CH1 resin therefore demonstrated to provide a more robust method to maintain the initial distribution of human IgG subclasses when purifying human IgG from polyclonal feed stock material, like human serum/plasma or samples obtained from the Cohn fractionation process.

Example 7. Purification of Human IgG and Fragments Thereof by an Anti IgG-CH1 Affinity Resin In order to investigate the CH1 selectivity of anti IgG-CH1 affinity resin in the purification of human IgG antibodies and fragments thereof, a resin immobilized with an anti IgG-CH1 VHH fragment (VHH#01) was tested with polyclonal human IgG, Fc- and Fab fragments. A column volume of 400 µl was used. All the chromatography experiments were performed on an Akta explorer 100. The antibody samples were loaded in PBS pH 7.4 (i.e. 4 ml human IgG at 1 mg/ml, 4 ml human IgG-Fc at ±0.25 mg/ml and 4 ml human IgG-Fab at ±0.25 mg/ml all in PBS, pH 7.4 at a flow rate of 150 cm/hr) and eluted with PBS pH 2.1. The resulting chromatograms are displayed in FIG. 5. Note that some reduction of the Fab preparation occurred during boiling of the starting material in SDS sample buffer (lane 1 FIG. 5C). Since the buffer of the Fab starting material contained residual amounts of cystein (from a papain digestion buffer) some reduction of the Fab fragments could be expected.

Figure 5B:
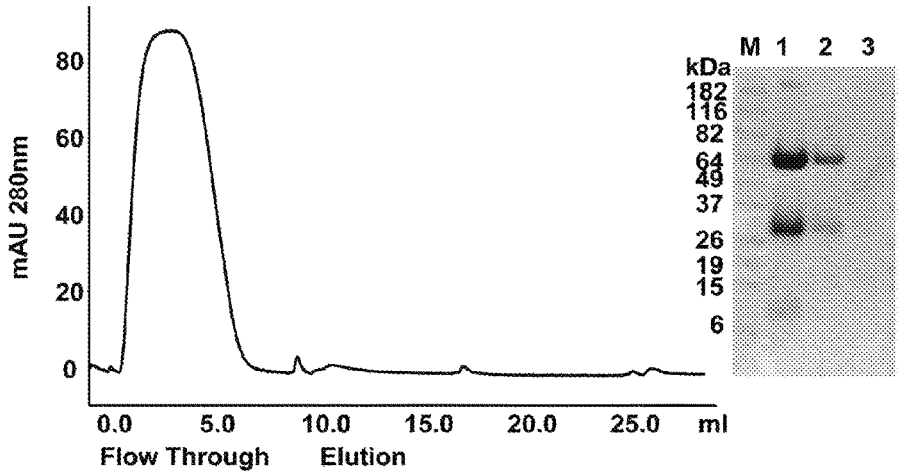
Figure 5C:
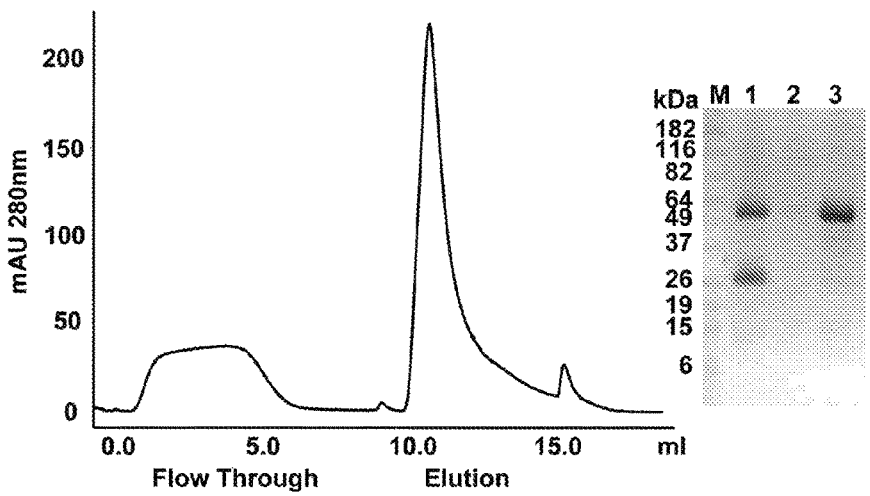

Results clearly demonstrated the ability of the anti IgG-CH1 resin to bind to both human IgG and—Fab fragments thereof (FIGS. 5A and 5C, respectively) but not to human IgG-Fc fragments (FIG. 5B).

Example 8. Purification of Human IgG Fab Fragments on Different Affinity Resins

The anti IgG-CH1 affinity resin was compared with Protein G (HiTrap, GEHC). on its ability to bind to human IgG Fab fragments (Jackson Immunoresearch). For the anti IgG-CH1 resin a column volume of 400 µl was used. Protein G HiTrap was tested at a volume of 1 ml. All chromatography experiments were performed on an Akta explorer 100. The antibody samples were loaded in PBS pH 7.4 (i.e. 4 ml human IgG Fab at ±0.25 mg/ml in PBS, pH 7.4 at a flow rate of 150 cm/hr) and eluted with PBS pH 2.1. The resulting chromatograms are displayed in FIG. 6.

Figure 6A:
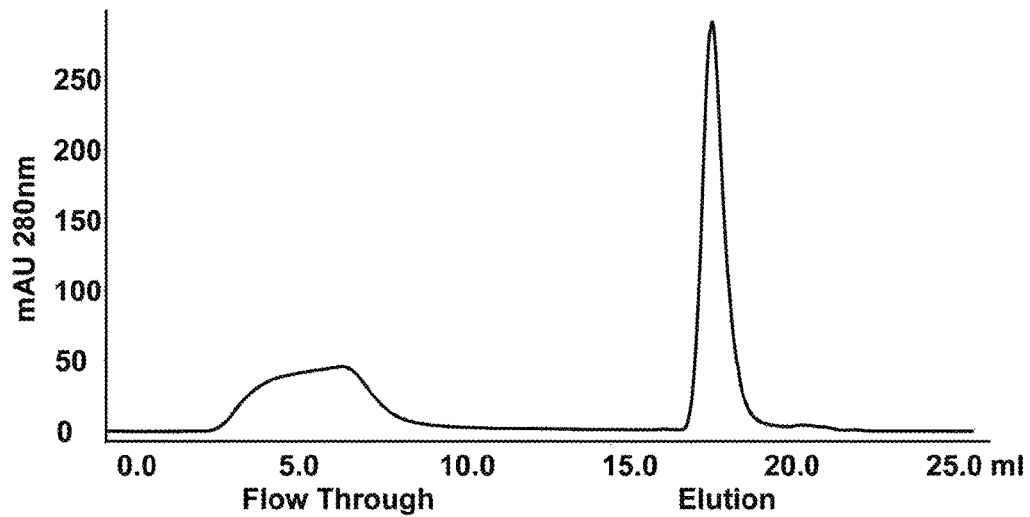
Figure 6B:
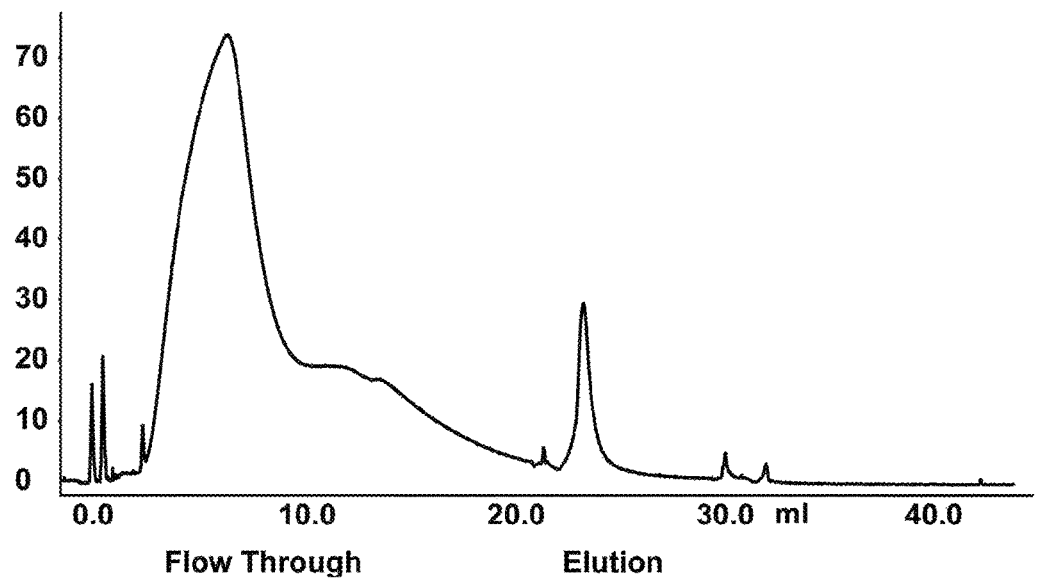

Results clearly demonstrated the ability of the anti IgG-CH1 resin to bind and elute the polyclonal human IgG Fab fragments (see FIG. 6A). As expected, poor binding was observed with the Protein G affinity matrix. Although the resin volume of Protein G was 2.5 fold more than used for the VHH based affinity resins, most of the Fab fragments were collected in the flow through fraction (see FIG. 6 B).

Since the polyclonal Fab sample did display some degradation (e.g. free light chains present), this could explain the $OD_{280}$ signal observed in the flow through fraction in the chromatogram of the anti IgG-CH1 affinity resin.

It should be noted that since the antigen-binding proteins of the current invention do not show any binding reactivity towards light chains of human antibodies, the use of affinity resins based on said antigen-binding proteins can enable the selective capturing of intact IgG or Fab fragments without co-binding of over-expressed free light chains present in e.g. the culture media of production strains expressing recombinant human IgG antibodies or human IgG Fab fragments.

In this respect, affinity ligands designed for binding to the light chain of antibodies can not discriminate between the excess of light chains and the corresponding IgG or Fab protein. As e.g. reported in a product sheet of the Fabsorbent F1P HF resin product (ProMetic Biosciences) comprising a ligand that binds to the variable domain of both kappa- and lambda light chains, the excess of light chains present in the supernatant of a CHO cell line expressing a human IgG antibody, is also captured and eluted by Fabsorbent F1P HF. This will therefore also count for other antigen binding domains targeting antibody light chains like Protein L, CaptureSelect Fab-kappa and lambda affinity ligands.

The results demonstrated good binding properties of the IgG-CH1 binding VHH fragments in chromatography thereby enabling a generic purification strategy for all human IgG subclass derived Fab fragments independent of the type of light chain. Hence, this favourable generic feature with regard to human Fab purification is being provided by the antigen-binding proteins of the current invention. Although Protein G is able to recognize an epitope present on Fab fragments of IgG antibodies, its low binding affinity for CH1 requires very low flow rates for sample loading (or through static binding only) as for instance described by Proudfoot et. al. (Prot. Expr and Purification (1992) 3, 368-373). In this case a flow rate of 1 column volume (3 ml) per hour was applied for sample loading. Proudfoot et. al. furthermore stated that the described Protein G purification method for Fab and F(ab)2 fragments may be applicable to only a subset of human antibody fragments. In this respect, Perosa et. al. (JIM (1997) 203, 153-155) indeed demonstrated that the Fab region of human IgG2 myeloma proteins did not bear the Protein G binding epitope and therefore could not be efficiently captured by Protein G sepharose after allowing a static binding procedure for 3 hrs. The results as displayed in FIG. 6B, confirm the insufficient binding reactivity of Protein G towards human IgG Fab fragments and as such can not serve as an efficient and generic tool for purification of said fragments.

Furthermore, due to the binding of Protein G to IgG Fc domains, it can not be used to selectively capture human IgG derived Fab fragments from feed stock samples consisting of a mixture of human IgG Fc—and Fab and/or F(ab)2 fragments (e.g. relating to IgG digestion procedures using papain and/or pepsin, respectively).

Example 9. Purification of Human Fab Fragments from IgG Digestion Mixtures

Papain and pepsin are commonly used proteases for the preparation of Fab and F(ab)2 fragments, respectively, from e.g. human IgG antibodies. Subsequent purification of human Fab and F(ab)2 fragments from these digestion mixtures can be obtained by e.g. a first removal of IgG-Fc fragments, intact and/or partially digested IgG from these mixtures by an anti-IgG Fc affinity resin followed by further purification of the Fab—or F(ab)2 fragments from the non-bound fraction in a second step by e.g. size exclusion chromatography. The latter step can also involve an affinity capture step, which preferably can cover all human IgG derived Fab fragments independent of IgG subclass and type of light chain. In this respect, Protein G shows low affinity for Fab and does not bind to all human IgG Fab subclasses, Protein A has some affinity for certain human VH3 domains but does not bind to all human IgG Fab fragments, Protein L only demonstrates binding to certain isotypes of the human VL-kappa family and each of the CaptureSelect ligands human Fab-kappa and lambda are only able to bind to either kappa—or lambda light chain containing Fab fragments (and not discriminating IgG from e.g. IgM). None of these antigen binding domains as such provide a generic use in covering all human IgG derived Fab or F(ab)2 fragments.

For this purpose, 1 ml of human IgG (20 mg/ml) was diluted with 2 ml digestion buffer (e.g. 0.020 M cysteine, 20 mM NaPhosphate, pH 7.4) and incubated overnight with 1 ml of papain beads (Thermo scientific, no. 20341) at 37° C. The IgG digestion mixture (supernatant) was collected and diluted to 20 ml with PBS, pH 7.4 (final IgG concentration of ±1 mg/ml). 3 ml of this sample was directly applied onto an affinity resin immobilized with an anti human IgG-Fc VHH fragment (400 µl resin, loaded at 150 cm/hr). Subsequently, the flow through fraction (non-bound fraction) was collected and directly applied onto an affinity resin immobilized with an anti IgG-CH1 VHH fragment (400 µl resin, loaded at 150 cm/hr) and after washing eluted at low pH to recover the bound Fab fragments. Results are summarized in FIG. 7.

Figure 7A:
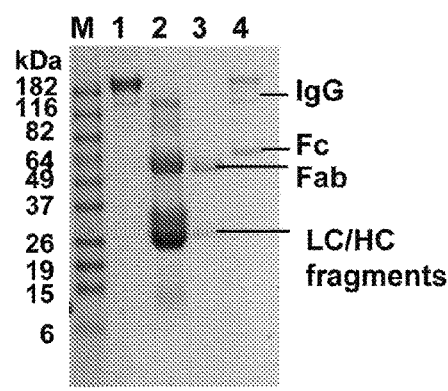

The results demonstrated very effective removal of IgG-Fc fragments and non- or partially digested IgG from the digestion mixture by the anti human IgG-Fc resin, showing a clear enrichment of Fab fragments in the non-bound fraction on the SDS page gel (lane 3 in FIG. 7A). The elution fraction of said resin (lane 4, FIG. 7A) contained Fc and non—or partially digested IgG. Note that since the non-bound fraction still contained some cysteine, partly reduction of the Fab fragment occurred during boiling of the samples in SDS sample buffer (indicated as LC/HC fragments in FIG. 7A).

Figure 7B:
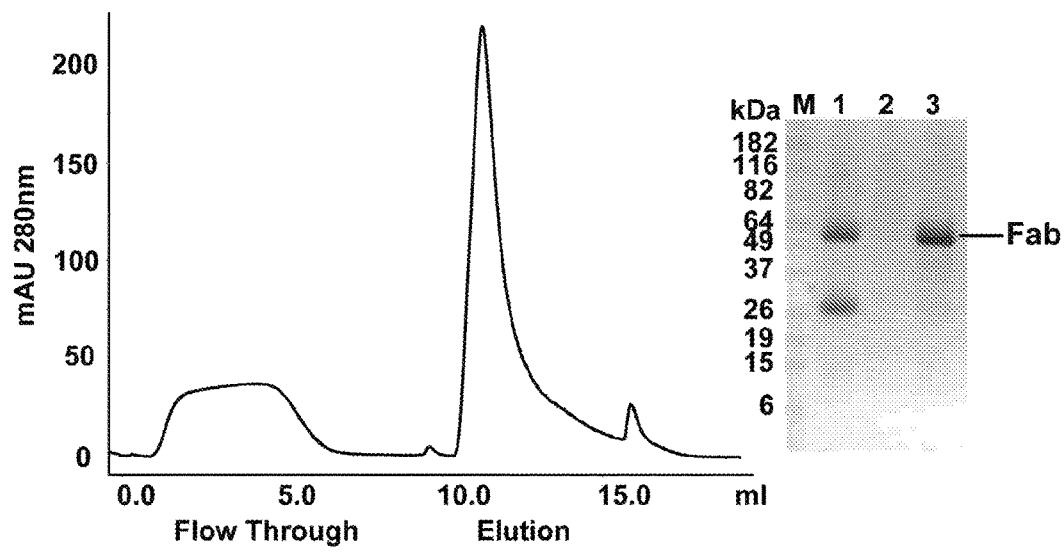

Subsequently, loading of this non-bound (and Fab enriched) fraction onto the anti IgG-CH1 resin showed effective capture of all human IgG Fab fragments since no Fab protein was visible in the flow through fraction (lane 2 FIG. 7 B). These results further confirmed the broad applicability of the antigen-binding proteins of the current invention of being able to bind any human IgG derived Fab fragment. The chromatogram did display an $OD_{280}$ signal of the flow through fraction indicating non CH1 related contaminants (e.g. buffer components like cysteine, residual papaine and/or free light chains). The bound Fab fragments were all recovered in the elution fraction as shown in lane 3 (FIG. 7B).

In combination with a resin that shows effective binding of Fc domains of human IgG antibodies, resins comprising an anti IgG-CH1 VHH fragment offer a unique method in obtaining purified human IgG Fab and/or F(ab)2 fragments from papain and/or pepsin digested IgG samples. In this respect, one can even think of "on column digestion" with papain and/or pepsin of IgG antibodies bound to an anti IgG-Fc affinity resin prior to starting the digestion, followed by applying the supernatant or digestion mixture after a certain amount of time of incubation, directly onto a resin comprising an anti IgG-CH1 VHH fragment. This can then facilitate e.g. a one step purification strategy for obtaining purified Fab and/or F(ab)2 fragments generated by papain and/or pepsin digestion of human IgG antibodies.

The invention claimed is:

1. A method for capturing a target molecule containing a human IgG-CH1 domain, the method comprising the steps of:
   (a) contacting the target molecule with an immunoadsorbent material comprising an antigen-binding protein immobilized on a support and
   (b) capturing the target molecule with the immunoadsorbent material by specific binding of the target material to the antigen-binding protein;
   wherein the antigen-binding protein:
      (i) is capable of binding to a single epitope present in the human IgG-CH1 domain,
      (ii) is cross-blocked by a VHH antigen-binding protein having the amino acid sequence of SEQ ID NO: 1,
      (iii) comprises an immunoglobulin-derived variable domain having a complete antigen-binding site for the single epitope, and
      (iv) is devoid of immunoglobin light chains.

2. The method according to claim 1, wherein the target molecule is selected from the group consisting of a human or humanized IgG, a human or humanized IgG1 molecule, a human or humanized IgG2 molecule, a human or humanized IgG3 molecule, a human or humanized IgG4 molecule, a human or humanized IgG Fab, a human or humanized IgG F(ab')$_2$, a one armed human or humanized IgG antibody, a single chain human or humanized IgG antibody, IVIG, and digests of human or humanized IgG, IgG1, IgG2, IgG3 or IgG4.

3. The method according to claim 1, wherein the antigen-binding protein is a camelid VHH or camelidized VH.

4. An isolated antigen-binding protein capable of binding to a human CH1 domain comprising the amino acid sequence of SEQ ID NO: 190,
   wherein the antigen-binding protein does not bind to a CH1 domain having the amino acid sequence of SEQ ID NO: 190, where Phe at position 9 is replaced with Tyr, Ser at position 40 is replaced with Thr, and Asn at position 91 is replaced with Ser, and
   wherein the antigen-binding protein:
      (i) is capable of binding to a single epitope present in the human IgG-CH1 domain,
      (ii) comprises an immunoglobulin-derived variable domain having a complete antigen-binding site for the single epitope, and
      (iii) is devoid of light chains.

5. The isolated antigen-binding protein of claim 4, wherein the CDR-I region contains the sequence Asn Thr Leu Ser Xaa1 Tyr Ala Xaa2 Gly (SEQ ID NO: 218), where Xaa1 is Gln, Arg or Pro and where Xaa2 is Met or Thr.

6. The isolated antigen-binding protein of claim 4, wherein the CDR-III region contains the sequence Arg Phe Leu Xaa3 Tyr Ala Ser Ser Asn Ala Tyr His Glu Xaa4 Leu Tyr Asn Tyr Asp Tyr (SEQ ID NO: 219), where Xaa3 is Gly or Pro, Xaa4 is Ala, Ser, or Thr.

7. The isolated antigen-binding protein of claim 4, wherein the antigen-binding protein is a camelid VHH or camelidized VH.

* * * * *

SEQUENCE LISTING

```
<160> NUMBER OF SEQ ID NOS: 219

<210> SEQ ID NO 1
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-0

<400> SEQUENCE: 1

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60
```

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
            85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 2
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-1

<400> SEQUENCE: 2

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Glu Ser Val
50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
            85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 3
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-2

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Asp Ser Val
50                  55                  60

-continued

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 4
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-3

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 5
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-4

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Ser Gly Lys Asn Thr Val Tyr

```
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 6
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-5

<400> SEQUENCE: 6

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 7
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-6

<400> SEQUENCE: 7

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Gly Lys Asn Thr Val Tyr
65                  70                  75                  80
```

```
Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 8
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-7

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k0-8

<400> SEQUENCE: 9

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Asn Gly Lys Asn Thr Val Tyr
65                  70                  75                  80
```

Leu Gln Met Asn Asn Leu Gln Pro Glu Asp Thr Ala Val Tyr Tyr Cys
            85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 10
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-0

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
            35                  40                  45

Ala Ala Ile Arg Trp Asn Asn Gly Ala Thr Tyr Tyr Ala Asp Ser Val
        50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
            85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 11
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-1

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
            35                  40                  45

Ala Ala Ile Arg Trp Asn Asn Gly Ala Thr Tyr Tyr Ala Glu Ser Val
        50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys

```
                    85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 12
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-2

<400> SEQUENCE: 12

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 13
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-3

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95
```

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 14
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-4

<400> SEQUENCE: 14

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-5

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

```
Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 16
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-6

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-7

<400> SEQUENCE: 17

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
```

Leu Tyr Asn Tyr Asp Tyr Trp Gly Gln Gly Thr Gln Val Thr Val Ser
            115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k1-8

<400> SEQUENCE: 18

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-0

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

```
Leu Tyr Asn Tyr Asp Tyr Trp Gly Gln Gly Thr Gln Val Thr Val Ser
        115                 120                 125
Ser
```

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-1

<400> SEQUENCE: 20

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125
Ser
```

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-2

<400> SEQUENCE: 21

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110
```

Leu Tyr Asn Tyr Asp Tyr Trp Gly Gln Gly Thr Gln Val Thr Val Ser
            115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-3

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-4

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser

```
                    115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-5

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-6

<400> SEQUENCE: 25

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125
```

Ser

<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-7

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 27
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k2-8

<400> SEQUENCE: 27

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 28
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-0

<400> SEQUENCE: 28
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 29
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-1

<400> SEQUENCE: 29
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 30
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-2

<400> SEQUENCE: 30

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 31
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-3

<400> SEQUENCE: 31

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 32
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-4

<400> SEQUENCE: 32

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 33
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-5

<400> SEQUENCE: 33

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

-continued

<210> SEQ ID NO 34
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-6

<400> SEQUENCE: 34

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 35
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-7

<400> SEQUENCE: 35

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 36

```
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k3-8

<400> SEQUENCE: 36
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 37
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-0

<400> SEQUENCE: 37
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 38
<211> LENGTH: 129
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-1

<400> SEQUENCE: 38

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 39
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-2

<400> SEQUENCE: 39

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 40
<211> LENGTH: 129
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-3

<400> SEQUENCE: 40

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 41
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-4

<400> SEQUENCE: 41

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 42
<211> LENGTH: 129
<212> TYPE: PRT
<213> ORGANISM: Artificial Sequence
```

<220> FEATURE:
<223> OTHER INFORMATION: Description of Artificial Sequence: Synthetic
      polypeptide
<220> FEATURE:
<223> OTHER INFORMATION: CH1-7 k4-5

<400> SEQUENCE: 42

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 43
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k4-6

<400> SEQUENCE: 43

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 44
<211> LENGTH: 129
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: CH1-7 k4-7

<400> SEQUENCE: 44

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 45
<211> LENGTH: 129
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CH1-7 k4-8

<400> SEQUENCE: 45

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 46
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7 k5-0

<400> SEQUENCE: 46

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 47
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-1

<400> SEQUENCE: 47

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 48
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: CH1-7 k5-2

<400> SEQUENCE: 48

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 49
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-3

<400> SEQUENCE: 49

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 50
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: CH1-7 k5-4

<400> SEQUENCE: 50

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 51
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-5

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 52
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-6

<400> SEQUENCE: 52

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 53
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-7

<400> SEQUENCE: 53

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 54
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k5-8

<400> SEQUENCE: 54

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Lys Glu Arg Glu Phe Val
        35                  40                  45
Ala Ala Ile Arg Trp Asn Asn Gly Ala Thr Tyr Tyr Ala Glu Ser Val
    50                  55                  60
Glu Gly Arg Phe Thr Ile Ser Arg Asp Asn Gly Lys Asn Thr Val Tyr
65                  70                  75                  80
Leu Gln Met Asn Asn Leu Lys Pro Glu Asp Thr Ala Val Tyr Tyr Cys
            85                  90                  95
Ala Gly Arg Phe Leu Gly Tyr Ala Ser Ser Asn Ala Tyr His Glu Ala
        100                 105                 110
Leu Tyr Asn Tyr Asp Tyr Trp Gly Gln Gly Thr Gln Val Thr Val Ser
    115                 120                 125
Ser
```

<210> SEQ ID NO 55
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7 k6-0

<400> SEQUENCE: 55

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Asn Gly Ala Thr Tyr Tyr Ala Asp Ser Val
    50                  55                  60
Lys Gly Arg Phe Thr Ile Ser Arg Asp Ser Gly Lys Asn Thr Val Tyr
65                  70                  75                  80
Leu Gln Met Asn Asn Leu Lys Pro Glu Asp Thr Ala Val Tyr Tyr Cys
            85                  90                  95
Ala Gly Arg Phe Leu Gly Tyr Ala Ser Ser Asn Ala Tyr His Glu Ala
        100                 105                 110
Leu Tyr Asn Tyr Asp Tyr Trp Gly Gln Gly Thr Gln Val Thr Val Ser
    115                 120                 125
Ser
```

<210> SEQ ID NO 56
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7 k6-1

<400> SEQUENCE: 56

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 57
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-2

<400> SEQUENCE: 57

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 58
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-3

<400> SEQUENCE: 58
```

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 59
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-4

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 60
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-5

<400> SEQUENCE: 60

Gln Val Gln Leu Gln Glu Ser Gly Gly Gly Leu Val Gln Ala Gly Gly
```

```
  1               5                  10                 15
Ser Leu Arg Leu Ser Cys Ala Val Ser Gly Asn Thr Leu Ser Arg Tyr
            20                  25                 30

Ala Met Gly Trp Phe Arg Gln Thr Pro Gly Asn Glu Arg Glu Phe Val
            35                  40                 45

Ala Ala Ile Arg Trp Asn Asn Gly Ala Thr Tyr Tyr Ala Asp Ser Val
            50                  55                 60

Lys Gly Arg Phe Thr Ile Ser Arg Asp Asn Gly Lys Asn Thr Val Tyr
 65                  70                 75                 80

Leu Gln Met Asn Asn Leu Lys Pro Glu Asp Thr Ala Val Tyr Tyr Cys
            85                  90                 95

Ala Gly Arg Phe Leu Gly Tyr Ala Ser Ser Asn Ala Tyr His Glu Ala
            100                 105                110

Leu Tyr Asn Tyr Asp Tyr Trp Gly Gln Gly Thr Gln Val Thr Val Ser
            115                 120                125

Ser
```

<210> SEQ ID NO 61
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-6

<400> SEQUENCE: 61

```
Gln Val Gln Leu Gln Glu Ser Gly Gly Gly Leu Val Gln Ala Gly Gly
 1               5                  10                 15

Ser Leu Arg Leu Ser Cys Ala Val Ser Gly Asn Thr Leu Ser Arg Tyr
            20                  25                 30

Ala Met Gly Trp Phe Arg Gln Thr Pro Gly Asn Glu Arg Glu Phe Val
            35                  40                 45

Ala Ala Ile Arg Trp Asn Asn Gly Ala Thr Tyr Tyr Ala Asp Ala Val
            50                  55                 60

Lys Gly Arg Phe Thr Ile Ser Arg Asp Asn Gly Lys Asn Thr Val Tyr
 65                  70                 75                 80

Leu Gln Met Asn Asn Leu Lys Pro Glu Asp Thr Ala Val Tyr Tyr Cys
            85                  90                 95

Ala Gly Arg Phe Leu Gly Tyr Ala Ser Ser Asn Ala Tyr His Glu Ala
            100                 105                110

Leu Tyr Asn Tyr Asp Tyr Trp Gly Gln Gly Thr Gln Val Thr Val Ser
            115                 120                125

Ser
```

<210> SEQ ID NO 62
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k6-7

<400> SEQUENCE: 62

```
Gln Val Gln Leu Gln Glu Ser Gly Gly Gly Leu Val Gln Ala Gly Gly
 1               5                  10                 15
```

```
Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Asp Ala Val
        50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 63
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7 k6-8

<400> SEQUENCE: 63

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
            35                  40                  45

Ala Ala Ile Arg Trp Asn Asn Gly Ala Thr Tyr Tyr Ala Glu Ser Val
        50                  55                  60

Lys Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 64
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7 k7-0

<400> SEQUENCE: 64

```
Gln Val Gln Leu Gln Glu Ser Gly Gly Gly Leu Val Gln Ala Gly Gly
1               5                   10                  15
```

```
Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 65
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-1

<400> SEQUENCE: 65

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 66
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-2

<400> SEQUENCE: 66

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
```

```
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 67
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-3

<400> SEQUENCE: 67

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 68
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-4

<400> SEQUENCE: 68

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30
```

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Ser Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 69
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-5

<400> SEQUENCE: 69

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
                20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Asn Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 70
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-6

<400> SEQUENCE: 70

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
                20                  25                  30

```
Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 71
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-7

<400> SEQUENCE: 71

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Lys Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 72
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k7-8

<400> SEQUENCE: 72

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
```

```
                35                  40                  45

Ala Ala Ile Arg Trp Asn Asn Gly Ala Thr Tyr Tyr Ala Glu Ser Val
    50                  55                  60

Lys Gly Arg Phe Thr Ile Ser Arg Asp Asn Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 73
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-0

<400> SEQUENCE: 73

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Gly Ala Thr Tyr Tyr Ala Asp Ser Val
    50                  55                  60

Lys Gly Arg Phe Thr Ile Ser Arg Asp Ser Gly Arg Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 74
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-1

<400> SEQUENCE: 74

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45
```

```
Ala Ala Ile Arg Trp Asn Asn Gly Ala Thr Tyr Tyr Ala Glu Ser Val
        50                  55                  60

Lys Gly Arg Phe Thr Ile Ser Arg Asp Ser Gly Arg Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 75
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-2

<400> SEQUENCE: 75

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Lys Gly Arg Phe Thr Ile Ser Arg Asp Thr Gly Arg Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 76
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-3

<400> SEQUENCE: 76

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45
```

```
Ala Ala Ile Arg Trp Asn Asn Gly Ala Thr Tyr Tyr Ala Glu Ser Val
        50                  55                  60

Lys Gly Arg Phe Thr Ile Ser Arg Asp Thr Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 77
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-4

<400> SEQUENCE: 77

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Asn Glu Arg Glu Phe Val
         35                  40                  45

Ala Ala Ile Arg Trp Asn Asn Gly Ala Thr Tyr Tyr Ala Asp Ala Val
        50                  55                  60

Lys Gly Arg Phe Thr Ile Ser Arg Asp Ser Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 78
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-5

<400> SEQUENCE: 78

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Asn Glu Arg Glu Phe Val
         35                  40                  45

Ala Ala Ile Arg Trp Asn Asn Gly Ala Thr Tyr Tyr Ala Asp Ser Val
```

-continued

```
               50                  55                  60

Lys Gly Arg Phe Thr Ile Ser Arg Asp Asn Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 79
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-6

<400> SEQUENCE: 79

Gln Val Gln Leu Gln Glu Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Asn Glu Arg Glu Phe Val
         35                  40                  45

Ala Ala Ile Arg Trp Asn Asn Gly Ala Thr Tyr Tyr Ala Asp Ala Val
     50                  55                  60

Lys Gly Arg Phe Thr Ile Ser Arg Asp Asn Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 80
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-7

<400> SEQUENCE: 80

Gln Val Gln Leu Gln Glu Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Asn Glu Arg Glu Phe Val
         35                  40                  45

Ala Ala Ile Arg Trp Asn Asn Gly Ala Thr Tyr Tyr Ala Asp Ala Val
     50                  55                  60
```

-continued

```
Lys Gly Arg Phe Thr Ile Ser Arg Asp Thr Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 81
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7 k8-8

<400> SEQUENCE: 81

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Asn Glu Arg Glu Phe Val
         35                  40                  45

Ala Ala Ile Arg Trp Asn Asn Gly Ala Thr Tyr Tyr Ala Glu Ser Val
     50                  55                  60

Lys Gly Arg Phe Thr Ile Ser Arg Asp Asn Gly Arg Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 82
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-1

<400> SEQUENCE: 82

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
             20                  25                  30

Ala Met Gly Trp Phe Arg Gln Ala Pro Gly Asn Glu Arg Glu Phe Val
         35                  40                  45

Ala Ala Ile Arg Trp Asn Asn Gly Asn Thr Tyr Tyr Ala Asp Ser Val
     50                  55                  60
```

```
Lys Gly Arg Phe Thr Ile Ser Arg Asp Ser Ala Lys Asn Thr Val Phe
 65                  70                  75                  80

Leu Gln Met Asn Ser Leu Gln Pro Glu Asp Thr Ala Val Tyr Phe Cys
                 85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 83
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-2

<400> SEQUENCE: 83

Gln Val Gln Leu Gln Asp Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Ala Pro Gly Asn Glu Arg Glu Phe Val
         35                  40                  45

Ala Ala Ile Arg Trp Asn Asn Gly Asn Thr Tyr Tyr Ala Asp Ser Val
     50                  55                  60

Glu Gly Arg Phe Thr Ile Ser Arg Asp Ser Ala Lys Asn Thr Val Tyr
 65                  70                  75                  80

Leu Gln Met Asn Ser Leu Gln Pro Glu Asp Thr Ala Val Tyr Tyr Cys
                 85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 84
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-3

<400> SEQUENCE: 84

Gln Val Gln Leu Gln Asp Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Ala Pro Gly Asn Glu Arg Glu Phe Val
         35                  40                  45

Ala Ala Ile Arg Trp Asn Asn Gly Asn Thr Tyr Tyr Ala Asp Ser Val
     50                  55                  60

Lys Gly Arg Phe Thr Ile Ser Arg Asp Ser Ala Lys Asn Thr Val Tyr
```

```
65                  70                  75                  80

Leu Gln Met Asn Ser Leu Gln Pro Glu Asp Thr Ala Val Tyr Tyr Cys
                85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 85
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-4

<400> SEQUENCE: 85

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Ser Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 86
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-5

<400> SEQUENCE: 86

Gln Val Gln Leu Gln Asp Ser Gly Gly Gly Ser Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Lys Gly Arg Phe Thr Ile Ser Arg Asp Ser Ala Lys Asn Thr Val Tyr
65                  70                  75                  80
```

-continued

Leu Gln Met Asn Ser Leu Gln Pro Glu Asp Thr Ala Val Tyr Phe Cys
                85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 87
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-6

<400> SEQUENCE: 87

Gln Val Gln Leu Gln Glu Ser Gly Gly Gly Leu Val Gln Ala Gly Ala
1               5                   10                  15

Ser Leu Arg Leu Ser Cys Glu Val Ser Gly Asn Thr Leu Ser Gln Tyr
            20                  25                  30

Ala Met Gly Trp Phe Arg Gln Val Pro Gly His Lys Arg Glu Phe Val
        35                  40                  45

Ala Ala Ile Arg Trp Thr Asn Gly Asn Thr Tyr Tyr Ala Asp Ser Val
    50                  55                  60

Glu Gly Arg Phe Thr Ile Ser Arg Asp Ser Ala Lys Lys Thr Val Tyr
65                  70                  75                  80

Leu Gln Met Asn Ser Leu Gln Pro Asp Asp Thr Ala Ile Tyr Tyr Cys
                85                  90                  95

Ala Ala Arg Phe Leu Pro Tyr Ala Ser Ser Asn Ala Tyr His Glu Ser
            100                 105                 110

Leu Tyr Asn Tyr Asp Tyr Trp Gly Gln Gly Thr Gln Val Thr Val Ser
        115                 120                 125

Ser

<210> SEQ ID NO 88
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-8

<400> SEQUENCE: 88

Gln Val Gln Leu Gln Glu Ser Gly Gly Gly Ser Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Glu Gly Arg Phe Thr Ile Ser Arg Tyr Ser Ala Lys Asn Leu Val Tyr
65                  70                  75                  80

Leu Gln Met Asn Ser Leu Gln Ala Glu Asp Thr Ala Ile Tyr Tyr Cys
                85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 89
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-9

<400> SEQUENCE: 89

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Gln Pro Glu Asp Thr Ala Val Tyr Tyr Cys
                85                  90                  95

Ala Ser Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 90
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 13_A12

<400> SEQUENCE: 90

Gln Val Gln Leu Gln Asp Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Thr Gly Trp Phe Arg Gln Ala Pro Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Glu Gly Arg Phe Thr Ile Ala Arg Asp Ser Ala Arg Asp Thr Val Tyr
65                  70                  75                  80

Leu Gln Met Asn Asn Leu Gln Pro Glu Asp Thr Ala Val Tyr Tyr Cys

```
                     85                  90                  95

Ala Ala Arg Phe Leu Pro Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 91
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 12_A9

<400> SEQUENCE: 91

Gln Val Gln Leu Gln Glu Ser Gly Gly Gly Ser Val Gln Ala Glu Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Asn Ser Gly His Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Asp Met Leu Gln Pro Glu Asp Thr Ala Val Tyr Tyr Cys
                85                  90                  95

Ala Ala Arg Phe Leu Pro Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 92
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 07_E8

<400> SEQUENCE: 92

Gln Val Gln Leu Gln Asp Ser Gly Gly Gly Leu Val Gln Ala Gly Gly
1               5                   10                  15

Ser Leu Thr Leu Ser Cys Val Val Ser Gly Asn Thr Leu Ser Arg Tyr
            20                  25                  30

Ala Met Gly Trp Phe Arg Gln Ala Pro Gly Asn Glu Arg Glu Phe Val
        35                  40                  45

Ala Ala Ile Arg Trp Glu Asn Gly Asn Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Asn Ser Leu Gln Pro Glu Asp Thr Ala Val Tyr Tyr Cys
                85                  90                  95
```

Ala Ala Arg Phe Leu Pro Tyr Ala Ser Ser Asn Ala Tyr His Glu Thr
            100                 105                 110

Leu Tyr Asn Tyr Asp Tyr Trp Gly Gln Gly Thr Gln Val Thr Val Ser
        115                 120                 125

Ser

<210> SEQ ID NO 93
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10_F1

<400> SEQUENCE: 93

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Gln Tyr
            20                  25                  30

Ala Met Gly Trp Phe Arg Gln Ala Pro Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Asn Ser Leu Gln Pro Glu Asp Thr Ala Val Tyr Tyr Cys
                85                  90                  95

Ala Ala Arg Phe Leu Pro Tyr Ala Ser Ser Asn Ala Tyr His Glu Thr
            100                 105                 110

Leu Tyr Asn Tyr Asp Tyr Trp Gly Gln Gly Thr Gln Val Thr Val Ser
        115                 120                 125

Ser

<210> SEQ ID NO 94
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10_F9

<400> SEQUENCE: 94

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Val Leu Gly Asn Glu Arg Glu Phe Val
        35                  40                  45

Ala Ala Ile Arg Trp Asn Asn Gly Asn Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Asn Ser Leu Gln Pro Glu Asp Thr Ala Val Tyr Tyr Cys
                85                  90                  95

```
Ala Ala Arg Phe Leu Pro Tyr Ala Ser Ser Asn Ala Tyr His Glu Ser
            100                 105                 110

Leu Tyr Asn Tyr Asp Tyr Trp Gly Gln Gly Thr Gln Val Thr Val Ser
        115                 120                 125

Ser

<210> SEQ ID NO 95
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 07_F7

<400> SEQUENCE: 95

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Pro Tyr
            20                  25                  30

Ala Met Gly Trp Phe Arg Gln Thr Pro Arg Asn Glu Arg Glu Phe Val
        35                  40                  45

Ala Pro Ile Arg Trp Asn Asn Gly Asn Thr Tyr Tyr Ala Asp Ser Val
    50                  55                  60

Glu Gly Arg Phe Thr Ile Ser Arg Asp Ser Ala Lys Asn Thr Val Tyr
65                  70                  75                  80

Leu Gln Met Asn Ser Leu Gln Pro Glu Asp Thr Ala Val Tyr Tyr Cys
                85                  90                  95

Ala Ala Arg Phe Leu Pro Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 96
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-9

<400> SEQUENCE: 96

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
```

```
                        100                 105                 110

Leu Tyr Asn Tyr Asp Tyr Trp Gly Gln Gly Thr Gln Val Thr Val Ser
            115                 120                 125

Ser
```

<210> SEQ ID NO 97
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-10

<400> SEQUENCE: 97

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser
```

<210> SEQ ID NO 98
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-11

<400> SEQUENCE: 98

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110
```

```
Leu Tyr Asn Tyr Asp Tyr Trp Gly Gln Gly Thr Gln Val Thr Val Ser
        115                 120                 125
Ser

<210> SEQ ID NO 99
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-12

<400> SEQUENCE: 99

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125
Ser

<210> SEQ ID NO 100
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-13

<400> SEQUENCE: 100

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110
```

Leu Tyr Asn Tyr Asp Tyr Trp Gly Gln Gly Thr Gln Val Thr Val Ser
            115                 120                 125

Ser

<210> SEQ ID NO 101
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-14

<400> SEQUENCE: 101

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 102
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-15

<400> SEQUENCE: 102

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser

<210> SEQ ID NO 103
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k1-16

<400> SEQUENCE: 103

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 104
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k1-17

<400> SEQUENCE: 104

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125
```

Ser

<210> SEQ ID NO 105
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-18

<400> SEQUENCE: 105

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 106
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-19

<400> SEQUENCE: 106

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 107
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k1-20

<400> SEQUENCE: 107

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 108
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k1-21

<400> SEQUENCE: 108

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

```
<210> SEQ ID NO 109
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-22

<400> SEQUENCE: 109

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 110
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-23

<400> SEQUENCE: 110

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

```
<210> SEQ ID NO 111
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-24

<400> SEQUENCE: 111

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 112
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-25

<400> SEQUENCE: 112

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

-continued

```
<210> SEQ ID NO 113
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-26

<400> SEQUENCE: 113

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 114
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-27

<400> SEQUENCE: 114

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 115
```

```
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-28

<400> SEQUENCE: 115
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 116
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k1-29

<400> SEQUENCE: 116
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

```
<210> SEQ ID NO 117
<211> LENGTH: 129
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-9

<400> SEQUENCE: 117

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 118
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-10

<400> SEQUENCE: 118

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 119
<211> LENGTH: 129
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k3-11

<400> SEQUENCE: 119

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Gly Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 120
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k3-12

<400> SEQUENCE: 120

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 121
<211> LENGTH: 129
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: CH1-7k3-13

<400> SEQUENCE: 121

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 122
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-14

<400> SEQUENCE: 122

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 123
<211> LENGTH: 129
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: CH1-7k3-15

<400> SEQUENCE: 123

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 124
<211> LENGTH: 129
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CH1-7k3-16

<400> SEQUENCE: 124

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 125
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CH1-7k3-17

<400> SEQUENCE: 125

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 126
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-18

<400> SEQUENCE: 126

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 127
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: CH1-7k3-19

<400> SEQUENCE: 127

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 128
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-20

<400> SEQUENCE: 128

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 129
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: CH1-7k3-21

<400> SEQUENCE: 129

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Asp Ser Val
    50                  55                  60
Glu Gly Arg Phe Thr Ile Ser Arg Asp Ser Gly Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 130
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-22

<400> SEQUENCE: 130

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Glu Ser Val
    50                  55                  60
Glu Gly Arg Phe Thr Ile Ser Arg Asp Ser Gly Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 131
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-23

<400> SEQUENCE: 131

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Asp Ser Val
    50                  55                  60
Glu Gly Arg Phe Thr Ile Ser Arg Asp Thr Gly Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 132
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-24

<400> SEQUENCE: 132

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Glu Ser Val
    50                  55                  60
Glu Gly Arg Phe Thr Ile Ser Arg Asp Thr Gly Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 133
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-25

<400> SEQUENCE: 133

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Asp Ala Val
50                  55                  60
Glu Gly Arg Phe Thr Ile Ser Arg Asp Ser Gly Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 134
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-26

<400> SEQUENCE: 134

```
Gln Val Gln Leu Gln Glu Ser Gly Gly Gly Leu Val Gln Ala Gly Gly
1               5                   10                  15
Ser Leu Arg Leu Ser Cys Ala Val Ser Gly Asn Thr Leu Ser Arg Tyr
            20                  25                  30
Ala Met Gly Trp Phe Arg Gln Thr Pro Gly Asn Glu Arg Glu Phe Val
        35                  40                  45
Ala Ala Ile Arg Trp Asn Glu Gly Ala Thr Tyr Tyr Ala Asp Ser Val
50                  55                  60
Glu Gly Arg Phe Thr Ile Ser Arg Asp Asn Ala Lys Asn Thr Val Tyr
65                  70                  75                  80
Leu Gln Met Asn Asn Leu Lys Pro Glu Asp Thr Ala Val Tyr Tyr Cys
                85                  90                  95
Ala Gly Arg Phe Leu Gly Tyr Ala Ser Ser Asn Ala Tyr His Glu Ala
            100                 105                 110
Leu Tyr Asn Tyr Asp Tyr Trp Gly Gln Gly Thr Gln Val Thr Val Ser
        115                 120                 125
Ser
```

<210> SEQ ID NO 135
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-27

<400> SEQUENCE: 135

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 136
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-28

<400> SEQUENCE: 136

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 137
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k3-29

<400> SEQUENCE: 137
```

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Asn Glu Arg Glu Phe Val
        35                  40                  45

Ala Ala Ile Arg Trp Asn Glu Gly Ala Thr Tyr Tyr Ala Glu Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 138
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-9

<400> SEQUENCE: 138

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Gly Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 139
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-10

<400> SEQUENCE: 139

Gln Val Gln Leu Gln Glu Ser Gly Gly Gly Leu Val Gln Ala Gly Gly

```
                1               5                  10                  15
Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
            35                  40              45

Ala Ala Ile Arg Trp Asn Asn Gly Ala Thr Tyr Tyr Ala Asp Ala Val
        50                  55                  60

Glu Gly Arg Phe Thr Ile Ser Arg Asp Asn Ala Lys Asn Thr Val Tyr
65                      70                  75                  80

Leu Gln Met Asn Asn Leu Lys Pro Glu Asp Thr Ala Val Tyr Tyr Cys
                    85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser
```

<210> SEQ ID NO 140
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-11

<400> SEQUENCE: 140

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
            35                  40              45

Ala Ala Ile Arg Trp Asn Asn Gly Ala Thr Tyr Tyr Ala Glu Ser Val
        50                  55                  60

Glu Gly Arg Phe Thr Ile Ser Arg Asp Asn Ala Lys Asn Thr Val Tyr
65                      70                  75                  80

Leu Gln Met Asn Asn Leu Lys Pro Glu Asp Thr Ala Val Tyr Tyr Cys
                    85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser
```

<210> SEQ ID NO 141
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-12

<400> SEQUENCE: 141

```
Gln Val Gln Leu Gln Glu Ser Gly Gly Gly Leu Val Gln Ala Gly Gly
1               5                   10                  15
```

-continued

```
Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 142
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-13

<400> SEQUENCE: 142

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser
```

<210> SEQ ID NO 143
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-14

<400> SEQUENCE: 143

```
Gln Val Gln Leu Gln Glu Ser Gly Gly Gly Leu Val Gln Ala Gly Gly
1               5                   10                  15
```

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 144
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-15

<400> SEQUENCE: 144

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Glu Ser Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 145
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-16

<400> SEQUENCE: 145

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr

```
                    20                  25                  30

Ala Met Gly Trp Phe Arg Gln Thr Pro Gly Lys Glu Arg Glu Phe Val
            35                  40                  45

Ala Ala Ile Arg Trp Asn Asn Ala Ala Thr Tyr Tyr Ala Asp Ala Val
        50                  55                  60

Glu Gly Arg Phe Thr Ile Ser Arg Asp Ser Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 146
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-17

<400> SEQUENCE: 146

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
            35                  40                  45

Ala Ala Ile Arg Trp Asn Asn Ala Ala Thr Tyr Tyr Ala Asp Ser Val
        50                  55                  60

Glu Gly Arg Phe Thr Ile Ser Arg Asp Asn Ala Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 147
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-18

<400> SEQUENCE: 147

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
            20                  25                  30
```

-continued

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 148
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-19

<400> SEQUENCE: 148

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Asn Ala Ala Thr Tyr Tyr Ala Asp Ala Val
    50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 149
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-20

<400> SEQUENCE: 149

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

```
Ala Met Gly Trp Phe Arg Gln Thr Pro Gly Lys Glu Arg Glu Phe Val
            35                  40                  45

Ala Ala Ile Arg Trp Asn Asn Ala Ala Thr Tyr Tyr Ala Glu Ser Val
        50                  55                  60

Glu Gly Arg Phe Thr Ile Ser Arg Asp Asn Ala Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 150
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-21

<400> SEQUENCE: 150

Gln Val Gln Leu Gln Glu Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Lys Glu Arg Glu Phe Val
            35                  40                  45

Ala Ala Ile Arg Trp Asn Gly Ala Thr Tyr Tyr Ala Asp Ser Val
        50                  55                  60

Glu Gly Arg Phe Thr Ile Ser Arg Asp Ser Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 151
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-22

<400> SEQUENCE: 151

Gln Val Gln Leu Gln Glu Ser Gly Gly Gly Leu Val Gln Ala Gly Gly
  1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Lys Glu Arg Glu Phe Val
```

```
                35                   40                  45

Ala Ala Ile Arg Trp Asn Glu Gly Ala Thr Tyr Tyr Ala Glu Ser Val
        50                   55                  60

Glu Gly Arg Phe Thr Ile Ser Arg Asp Ser Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 152
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-23

<400> SEQUENCE: 152

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ser Val
    50                  55                  60

Glu Gly Arg Phe Thr Ile Ser Arg Asp Thr Gly Lys Asn Thr Val Tyr
 65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
            115                 120                 125

Ser

<210> SEQ ID NO 153
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-24

<400> SEQUENCE: 153

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45
```

```
Ala Ala Ile Arg Trp Asn Glu Gly Ala Thr Tyr Tyr Ala Glu Ser Val
        50                  55                  60

Glu Gly Arg Phe Thr Ile Ser Arg Asp Thr Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 154
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-25

<400> SEQUENCE: 154

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
        50                  55                  60

Glu Gly Arg Phe Thr Ile Ser Arg Asp Ser Gly Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 155
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-26

<400> SEQUENCE: 155

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45
```

```
Ala Ala Ile Arg Trp Asn Glu Gly Ala Thr Tyr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 156
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-27

<400> SEQUENCE: 156

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
    50                  55                  60

Glu Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Gly Arg Phe Leu Gly Tyr Ala Ser Ser Asn Ala Tyr His Glu Ala
            100                 105                 110

Leu Tyr Asn Tyr Asp Tyr Trp Gly Gln Gly Thr Gln Val Thr Val Ser
        115                 120                 125

Ser

<210> SEQ ID NO 157
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-28

<400> SEQUENCE: 157

Gln Val Gln Leu Gln Glu Ser Gly Gly Gly Leu Val Gln Ala Gly Gly
1               5                   10                  15

Ser Leu Arg Leu Ser Cys Ala Val Ser Gly Asn Thr Leu Ser Arg Tyr
            20                  25                  30

Ala Met Gly Trp Phe Arg Gln Thr Pro Gly Lys Glu Arg Glu Phe Val
        35                  40                  45

Ala Ala Ile Arg Trp Asn Glu Gly Ala Thr Tyr Tyr Ala Asp Ala Val
    50                  55                  60
```

```
                50                  55                  60
Glu Gly Arg Phe Thr Ile Ser Arg Asp Thr Gly Lys Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 158
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1-7k5-29

<400> SEQUENCE: 158

Gln Val Gln Leu Gln Glu Ser Gly Gly Gly Leu Val Gln Ala Gly Gly
 1               5                  10                  15

Ser Leu Arg Leu Ser Cys Ala Val Ser Gly Asn Thr Leu Ser Arg Tyr
             20                  25                  30

Ala Met Gly Trp Phe Arg Gln Thr Pro Gly Lys Glu Arg Glu Phe Val
         35                  40                  45

Ala Ala Ile Arg Trp Asn Glu Gly Ala Thr Tyr Tyr Ala Glu Ser Val
     50                  55                  60

Glu Gly Arg Phe Thr Ile Ser Arg Asp Asn Ala Lys Asn Thr Val Tyr
 65                  70                  75                  80

Leu Gln Met Asn Asn Leu Lys Pro Glu Asp Thr Ala Val Tyr Tyr Cys
                 85                  90                  95

Ala Gly Arg Phe Leu Gly Tyr Ala Ser Ser Asn Ala Tyr His Glu Ala
                100                 105                 110

Leu Tyr Asn Tyr Asp Tyr Trp Gly Gln Gly Thr Gln Val Thr Val Ser
            115                 120                 125

Ser

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-I

<400> SEQUENCE: 159

Asn Thr Leu Ser Arg Tyr Ala Met Gly
 1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: CDR-I

<400> SEQUENCE: 160

Asn Thr Leu Ser Gln Tyr Ala Met Gly
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-I

<400> SEQUENCE: 161

Asn Thr Leu Ser Arg Tyr Ala Thr Gly
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-I

<400> SEQUENCE: 162

Asn Thr Leu Ser Pro Tyr Ala Met Gly
1               5

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 163

Ala Ile Arg Trp Asn Asn Gly Ala Thr Tyr Tyr Ala Asp Ser Val Glu
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 164

Ala Ile Arg Trp Asn Asn Gly Ala Thr Tyr Tyr Ala Glu Ser Val Glu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: CDR-II

<400> SEQUENCE: 165

Ala Ile Arg Trp Asn Asn Gly Ala Thr Tyr Tyr Ala Asp Ala Val Glu
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 166

Ala Ile Arg Trp Asn Asn Gly Ala Thr Tyr Tyr Ala Asp Ser Val Lys
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 167

Ala Ile Arg Trp Asn Asn Gly Ala Thr Tyr Tyr Ala Glu Ser Val Lys
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 168

Ala Ile Arg Trp Asn Asn Gly Ala Thr Tyr Tyr Ala Asp Ala Val Lys
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 169

Ala Ile Arg Trp Asn Asn Gly Asn Thr Tyr Tyr Ala Asp Ser Val Lys
1               5                   10                  15

<210> SEQ ID NO 170
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: CDR-II

<400> SEQUENCE: 170

Ala Ile Arg Trp Asn Asn Gly Asn Thr Tyr Tyr Ala Asp Ser Val Glu
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 171

Ala Ile Arg Trp Asn Asn Gly Ala Thr Tyr Tyr Ala Asp Ser Val Glu
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 172

Ala Ile Arg Trp Thr Asn Gly Asn Thr Tyr Tyr Ala Asp Ser Val Glu
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 173

Ala Ile Arg Trp Asn Ser Gly His Thr Tyr Tyr Ala Asp Ser Val Glu
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 174

Ala Ile Arg Trp Glu Asn Gly Asn Thr Tyr Tyr Ala Asp Ser Val Glu
1               5                   10                  15

<210> SEQ ID NO 175
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: CDR-II

<400> SEQUENCE: 175

Pro Ile Arg Trp Asn Asn Gly Asn Thr Tyr Tyr Ala Asp Ser Val Glu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 176

<400> SEQUENCE: 176

Ala Ile Arg Trp Asn Asn Ala Ala Thr Tyr Tyr Ala Asp Ser Val Glu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 177

<400> SEQUENCE: 177

Ala Ile Arg Trp Asn Asn Ala Ala Thr Tyr Tyr Ala Glu Ser Val Glu
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 178

<400> SEQUENCE: 178

Ala Ile Arg Trp Asn Asn Ala Ala Thr Tyr Tyr Ala Asp Ala Val Glu
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 179

<400> SEQUENCE: 179

Ala Ile Arg Trp Asn Glu Gly Ala Thr Tyr Tyr Ala Asp Ser Val Glu
1               5                   10                  15

<210> SEQ ID NO 180
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 180

<400> SEQUENCE: 180

Ala Ile Arg Trp Asn Glu Gly Ala Thr Tyr Tyr Ala Glu Ser Val Glu
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-II 181

<400> SEQUENCE: 181

Ala Ile Arg Trp Asn Glu Gly Ala Thr Tyr Tyr Ala Asp Ala Val Glu
1               5                   10                  15

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-III

<400> SEQUENCE: 182

Arg Phe Leu Gly Tyr Ala Ser Ser Asn Ala Tyr His Glu Ala Leu Tyr
1               5                   10                  15

Asn Tyr Asp Tyr
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-III

<400> SEQUENCE: 183

Arg Phe Leu Pro Tyr Ala Ser Ser Asn Ala Tyr His Glu Ala Leu Tyr
1               5                   10                  15

Asn Tyr Asp Tyr
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-III

<400> SEQUENCE: 184
```

```
Arg Phe Leu Pro Tyr Ala Ser Ser Asn Ala Tyr His Glu Ser Leu Tyr
1               5                   10                  15

Asn Tyr Asp Tyr
            20
```

<210> SEQ ID NO 185
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-III

<400> SEQUENCE: 185

```
Arg Phe Leu Pro Tyr Ala Ser Ser Asn Ala Tyr His Glu Thr Leu Tyr
1               5                   10                  15

Asn Tyr Asp Tyr
            20
```

<210> SEQ ID NO 186
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FR1

<400> SEQUENCE: 186

```
Gln Val Gln Leu Gln Glu Ser Gly Gly Gly Leu Val Gln Ala Gly Gly
1               5                   10                  15

Ser Leu Arg Leu Ser Cys Ala Val Ser Gly
            20                  25
```

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FR2

<400> SEQUENCE: 187

```
Trp Phe Arg Gln Thr Pro Gly Asn Glu Arg Glu Phe Val Ala
1               5                   10
```

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FR3

<400> SEQUENCE: 188

```
Gly Arg Phe Thr Ile Ser Arg Asp Ser Gly Lys Asn Thr Val Tyr Leu
1               5                   10                  15

Gln Met Asn Asn Leu Lys Pro Glu Asp Thr Ala Val Tyr Tyr Cys Ala
            20                  25                  30
```

Gly

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FR4

<400> SEQUENCE: 189

Trp Gly Gln Gly Thr Gln Val Thr Val Ser Ser
1               5                   10

<210> SEQ ID NO 190
<211> LENGTH: 98
<212> TYPE: PRT
<213> ORGANISM: Homo sapiens
<220> FEATURE:
<223> OTHER INFORMATION: Human IgG1 CH1

<400> SEQUENCE: 190

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 191
<211> LENGTH: 98
<212> TYPE: PRT
<213> ORGANISM: Homo sapiens
<220> FEATURE:
<223> OTHER INFORMATION: Human IgG2 CH1

<400> SEQUENCE: 191

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 192
<211> LENGTH: 98
<212> TYPE: PRT
<213> ORGANISM: Homo sapiens
<220> FEATURE:
<223> OTHER INFORMATION: Human IgG3 CH1

<400> SEQUENCE: 192

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 193
<211> LENGTH: 98
<212> TYPE: PRT
<213> ORGANISM: Homo sapiens
<220> FEATURE:
<223> OTHER INFORMATION: Human IgG4 CH1

<400> SEQUENCE: 193

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 194
<211> LENGTH: 97
<212> TYPE: PRT
<213> ORGANISM: Papio sp.
<220> FEATURE:
<223> OTHER INFORMATION: Baboon IgG1 CH1

<400> SEQUENCE: 194

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ser Leu Thr Ser
        35                  40                  45

Gly Val His Thr Phe Pro Ala Val Leu Gln Ser Ser Gly Leu Tyr Ser

-continued

```
                 50                  55                  60
Leu Ser Ser Val Val Thr Val Pro Ser Ser Leu Gly Gln Thr Tyr
 65                  70                  75                  80

Val Cys Asn Val Asn His Lys Pro Ser Asn Thr Lys Val Asp Lys Lys
                 85                  90                  95

Val
```

<210> SEQ ID NO 195
<211> LENGTH: 98
<212> TYPE: PRT
<213> ORGANISM: Pan troglodytes
<220> FEATURE:
<223> OTHER INFORMATION: Chimpanzee IgG CH1

<400> SEQUENCE: 195

```
Ala Ser Thr Lys Gly Pro Ser Val Phe Pro Leu Ala Pro Ser Ser Lys
  1               5                  10                  15

Ser Thr Ser Gly Gly Thr Gln Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asp His Lys Pro Ser Asn Thr Lys Val Asp Lys
                 85                  90                  95

Lys Val
```

<210> SEQ ID NO 196
<211> LENGTH: 98
<212> TYPE: PRT
<213> ORGANISM: Macaca mulatta
<220> FEATURE:
<223> OTHER INFORMATION: Rhesus IgG CH1

<400> SEQUENCE: 196

```
Ala Ser Thr Lys Gly Pro Ser Val Phe Pro Leu Ala Pro Ser Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ser Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Val Cys Asn Val Asn His Lys Pro Ser Asn Thr Lys Val Asp Lys
                 85                  90                  95

Arg Val
```

<210> SEQ ID NO 197
<211> LENGTH: 98
<212> TYPE: PRT
<213> ORGANISM: Felis catus
<220> FEATURE:
<223> OTHER INFORMATION: Cat IgG1 CH1

<400> SEQUENCE: 197

```
Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val
```

<210> SEQ ID NO 198
<211> LENGTH: 98
<212> TYPE: PRT
<213> ORGANISM: Canis familiaris
<220> FEATURE:
<223> OTHER INFORMATION: Dog IgG (A) CH1

<400> SEQUENCE: 198

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val
```

<210> SEQ ID NO 199
<211> LENGTH: 94
<212> TYPE: PRT
<213> ORGANISM: Cavia porcellus
<220> FEATURE:
<223> OTHER INFORMATION: Guinea Pig IgG2 CH1

<400> SEQUENCE: 199

```
Ala Arg Thr Thr Ala Pro Ser Val Phe Pro Leu Ala Ala Ser Cys Val
1               5                   10                  15

Asp Thr Ser Gly Ser Met Met Thr Leu Gly Cys Leu Val Lys Gly Tyr
            20                  25                  30

Phe Pro Glu Pro Val Thr Val Lys Trp Asn Ser Gly Ala Leu Thr Ser
        35                  40                  45

Gly Val His Thr Phe Pro Ala Val Leu Gln Ser Gly Leu Tyr Ser Leu
    50                  55                  60

Thr Ser Met Val Thr Val Pro Ser Ser Gln Lys Lys Ala Thr Cys Asn
65                  70                  75                  80

Val Ala His Pro Ala Ser Ser Thr Lys Val Asp Lys Thr Val
                85                  90
```

-continued

```
<210> SEQ ID NO 200
<211> LENGTH: 98
<212> TYPE: PRT
<213> ORGANISM: Equus caballus
<220> FEATURE:
<223> OTHER INFORMATION: Horse IgG1 CH1

<400> SEQUENCE: 200

Ala Ser Thr Thr Ala Pro Lys Val Phe Ala Leu Ala Pro Gly Cys Gly
1               5                   10                  15

Thr Thr Ser Asp Ser Thr Val Ala Leu Gly Cys Leu Val Ser Gly Tyr
            20                  25                  30

Phe Pro Glu Pro Val Lys Val Ser Trp Asn Ser Gly Ser Leu Thr Ser
        35                  40                  45

Gly Val His Thr Phe Pro Ser Val Leu Gln Ser Ser Gly Phe Tyr Ser
    50                  55                  60

Leu Ser Ser Met Val Thr Val Pro Ala Ser Thr Trp Thr Ser Glu Thr
65                  70                  75                  80

Tyr Ile Cys Asn Val Val His Ala Ala Ser Asn Phe Lys Val Asp Lys
                85                  90                  95

Arg Ile

<210> SEQ ID NO 201
<211> LENGTH: 95
<212> TYPE: PRT
<213> ORGANISM: Oryctolagus cuniculus
<220> FEATURE:
<223> OTHER INFORMATION: Rabbit IgG CH1

<400> SEQUENCE: 201

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val
                85                  90                  95

<210> SEQ ID NO 202
<211> LENGTH: 98
<212> TYPE: PRT
<213> ORGANISM: Sus sp.
<220> FEATURE:
<223> OTHER INFORMATION: Swine IgG1 CH1

<400> SEQUENCE: 202

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60
```

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Lys Val Asp Lys
                85                  90                  95

Arg Val

<210> SEQ ID NO 203
<211> LENGTH: 98
<212> TYPE: PRT
<213> ORGANISM: Sus sp.
<220> FEATURE:
<223> OTHER INFORMATION: Swine IgG2 CH1

<400> SEQUENCE: 203

Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
                20                  25                  30

Phe Pro Glu Pro Val Thr Val Thr Trp Asn Ser Gly Ala Leu Thr Ser
            35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Lys Val Asp Lys
                85                  90                  95

Arg Val

<210> SEQ ID NO 204
<211> LENGTH: 96
<212> TYPE: PRT
<213> ORGANISM: Bos sp.
<220> FEATURE:
<223> OTHER INFORMATION: Bovine IgG1 CH1

<400> SEQUENCE: 204

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Thr Gln Thr
65                  70                  75                  80

Phe Thr Cys Asn Val Ala His Pro Ala Ser Ser Thr Lys Val Asp Lys
                85                  90                  95

<210> SEQ ID NO 205
<211> LENGTH: 96
<212> TYPE: PRT
<213> ORGANISM: Bos sp.
<220> FEATURE:
<223> OTHER INFORMATION: Bovine IgG2 CH1

<400> SEQUENCE: 205

Ala Ser Thr Thr Ala Pro Lys Val Tyr Pro Leu Ser Ser Cys Cys Gly
1               5                   10                  15

-continued

```
Asp Lys Ser Ser Gly Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Gly Thr Gln Thr
65                  70                  75                  80

Phe Thr Cys Asn Val Ala His Pro Ala Ser Ser Thr Lys Val Asp Lys
                85                  90                  95

<210> SEQ ID NO 206
<211> LENGTH: 98
<212> TYPE: PRT
<213> ORGANISM: Ovis aries
<220> FEATURE:
<223> OTHER INFORMATION: Sheep IgG1 CH1

<400> SEQUENCE: 206

Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30

Met Pro Glu Pro Val Thr Val Thr Trp Asn Ser Gly Ala Leu Thr Ser
        35                  40                  45

Gly Val His Thr Phe Pro Ala Ile Leu Gln Ser Ser Gly Leu Tyr Ser
    50                  55                  60

Leu Ser Ser Val Val Thr Val Pro Ala Ser Thr Ser Gly Ala Gln Thr
65                  70                  75                  80

Phe Ile Cys Asn Val Ala His Pro Ala Ser Ser Thr Lys Val Asp Lys
                85                  90                  95

Arg Val

<210> SEQ ID NO 207
<211> LENGTH: 98
<212> TYPE: PRT
<213> ORGANISM: Capra hircus
<220> FEATURE:
<223> OTHER INFORMATION: Goat IgG1 CH1

<400> SEQUENCE: 207

Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30

Met Pro Glu Pro Val Thr Val Thr Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Thr Ser Gly Ala Gln Thr
65                  70                  75                  80

Phe Ile Cys Asn Val Ala His Pro Ala Ser Ser Thr Lys Val Asp Lys
                85                  90                  95

Arg Val

<210> SEQ ID NO 208
<211> LENGTH: 98
```

-continued

```
<212> TYPE: PRT
<213> ORGANISM: Lama glama
<220> FEATURE:
<223> OTHER INFORMATION: Llama IgG1a CH1

<400> SEQUENCE: 208

Ala Ser Thr Lys Ala Pro Ser Val Tyr Pro Leu Thr Ala Arg Cys Gly
1               5                   10                  15

Asp Thr Pro Gly Ser Thr Val Ala Phe Gly Cys Leu Val Trp Gly Tyr
            20                  25                  30

Ile Pro Glu Pro Val Thr Val Thr Trp Asn Ser Gly Ala Leu Ser Ser
        35                  40                  45

Gly Val His Thr Phe Pro Ser Val Phe Met Ser Ser Gly Leu Tyr Thr
    50                  55                  60

Leu Ser Ser Leu Val Thr Met Pro Ala Ser Ser Thr Gly Lys Thr
65                  70                  75                  80

Phe Ile Cys Asn Val Ala His Pro Ala Ser Ser Thr Lys Val Asp Lys
                85                  90                  95

Arg Val

<210> SEQ ID NO 209
<211> LENGTH: 98
<212> TYPE: PRT
<213> ORGANISM: Lama glama
<220> FEATURE:
<223> OTHER INFORMATION: Llama IgG1b CH1

<400> SEQUENCE: 209

Ala Ser Thr Lys Ala Pro Ser Val Tyr Pro Leu Thr Ala Arg Cys Gly
1               5                   10                  15

Asp Thr Pro Gly Ser Thr Val Ala Phe Gly Cys Leu Val Trp Gly Tyr
            20                  25                  30

Ile Pro Glu Pro Val Thr Val Thr Trp Asn Ser Gly Ala Leu Ser Ser
        35                  40                  45

Gly Val His Thr Phe Pro Ser Val Phe Met Ser Ser Gly Leu Tyr Ser
    50                  55                  60

Leu Ser Ser Leu Val Thr Leu Pro Thr Ser Ser Thr Gly Lys Thr
65                  70                  75                  80

Phe Ile Cys Asn Val Ala His Pro Ala Ser Ser Thr Lys Val Asp Lys
                85                  90                  95

Arg Val

<210> SEQ ID NO 210
<211> LENGTH: 97
<212> TYPE: PRT
<213> ORGANISM: Rattus sp.
<220> FEATURE:
<223> OTHER INFORMATION: Rat IgG1 CH1

<400> SEQUENCE: 210

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60
```

```
Thr Ser Ser Val Thr Val Pro Ser Ser Thr Trp Pro Ser Gln Thr Val
 65                  70                  75                  80

Thr Cys Asn Val Ala His Pro Ala Ser Ser Thr Lys Val Asp Lys Lys
                 85                  90                  95

Ile

<210> SEQ ID NO 211
<211> LENGTH: 97
<212> TYPE: PRT
<213> ORGANISM: Rattus sp.
<220> FEATURE:
<223> OTHER INFORMATION: Rat IgG2a CH1

<400> SEQUENCE: 211

Ala Glu Thr Thr Ala Pro Ser Val Tyr Pro Leu Ala Pro Gly Thr Ala
 1               5                  10                  15

Leu Lys Ser Asn Ser Met Val Thr Leu Gly Cys Leu Val Lys Gly Tyr
                20                  25                  30

Phe Pro Glu Pro Val Thr Val Trp Asn Ser Gly Ala Leu Ser Ser
             35                  40                  45

Gly Val His Thr Phe Pro Ala Val Leu Gln Ser Gly Leu Tyr Thr Leu
 50                  55                  60

Thr Ser Ser Val Thr Val Pro Ser Ser Thr Trp Ser Ser Gln Ala Val
 65                  70                  75                  80

Thr Cys Asn Val Ala His Pro Ala Ser Ser Thr Lys Val Asp Lys Lys
                 85                  90                  95

Ile

<210> SEQ ID NO 212
<211> LENGTH: 95
<212> TYPE: PRT
<213> ORGANISM: Rattus sp.
<220> FEATURE:
<223> OTHER INFORMATION: Rat IgG2b CH1

<400> SEQUENCE: 212

Ala Gln Thr Thr Ala Pro Ser Val Tyr Pro Leu Ala Pro Gly Cys Gly
 1               5                  10                  15

Asp Thr Thr Ser Ser Thr Val Thr Leu Gly Cys Leu Val Lys Gly Tyr
                20                  25                  30

Phe Pro Glu Pro Val Thr Val Thr Trp Asn Ser Gly Ala Leu Ser Ser
             35                  40                  45

Asp Val His Thr Phe Pro Ala Val Leu Gln Ser Gly Leu Tyr Thr Leu
 50                  55                  60

Thr Ser Ser Val Thr Ser Ser Thr Trp Pro Ser Gln Thr Val Thr Cys
 65                  70                  75                  80

Asn Val Ala His Pro Ala Ser Ser Thr Lys Val Asp Lys Lys Val
                 85                  90                  95

<210> SEQ ID NO 213
<211> LENGTH: 97
<212> TYPE: PRT
<213> ORGANISM: Rattus sp.
<220> FEATURE:
<223> OTHER INFORMATION: Rat IgG2c CH1

<400> SEQUENCE: 213

Ala Arg Thr Thr Ala Pro Ser Val Tyr Pro Leu Val Pro Gly Cys Ser
 1               5                  10                  15
```

-continued

Gly Thr Ser Gly Ser Leu Val Thr Leu Gly Cys Leu Val Lys Gly Tyr
        20                  25                  30

Phe Pro Glu Pro Val Thr Val Lys Trp Asn Ser Gly Ala Leu Ser Ser
            35                  40                  45

Gly Val His Thr Phe Pro Ala Val Leu Gln Ser Gly Leu Tyr Thr Leu
    50                  55                  60

Ser Ser Val Thr Val Pro Ser Ser Thr Trp Ser Gln Thr Val
65                  70                  75                  80

Thr Cys Ser Val Ala His Pro Ala Thr Lys Ser Asn Leu Ile Lys Arg
                85                  90                  95

Ile

<210> SEQ ID NO 214
<211> LENGTH: 97
<212> TYPE: PRT
<213> ORGANISM: Mus sp.
<220> FEATURE:
<223> OTHER INFORMATION: Mouse IgG1 CH1

<400> SEQUENCE: 214

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile

<210> SEQ ID NO 215
<211> LENGTH: 97
<212> TYPE: PRT
<213> ORGANISM: Mus sp.
<220> FEATURE:
<223> OTHER INFORMATION: Mouse IgG2a CH1

<400> SEQUENCE: 215

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile

<210> SEQ ID NO 216

```
<211> LENGTH: 97
<212> TYPE: PRT
<213> ORGANISM: Mus sp.
<220> FEATURE:
<223> OTHER INFORMATION: Mouse IgG2b CH1

<400> SEQUENCE: 216

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu

<210> SEQ ID NO 217
<211> LENGTH: 97
<212> TYPE: PRT
<213> ORGANISM: Mus sp.
<220> FEATURE:
<223> OTHER INFORMATION: Mouse IgG3 CH1

<400> SEQUENCE: 217

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
            20                  25                  30

Phe Pro Glu Pro Val Thr Val Lys Trp Asn Tyr Gly Ala Leu Ser Ser
        35                  40                  45

Gly Val Arg Thr Val Ser Ser Val Leu Gln Ser Gly Phe Tyr Ser Leu
    50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Gln, Arg or Pro
<220> FEATURE:
<221> NAME/KEY: MOD_RES
<222> LOCATION: (8)..(8)
<223> OTHER INFORMATION: Met or Thr

<400> SEQUENCE: 218

Asn Thr Leu Ser Xaa Tyr Ala Xaa Gly
1               5
```

```
<210> SEQ ID NO 219
<211> LENGTH: 20
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Gly or Pro
<220> FEATURE:
<221> NAME/KEY: MOD_RES
<222> LOCATION: (14)..(14)
<223> OTHER INFORMATION: Ala, Ser or Thr

<400> SEQUENCE: 219

Arg Phe Leu Xaa Tyr Ala Ser Ser Asn Ala Tyr His Glu Xaa Leu Tyr
1               5                   10                  15

Asn Tyr Asp Tyr
            20
```